(12) United States Patent
Moreadith et al.

(10) Patent No.: US 11,065,340 B2
(45) Date of Patent: *Jul. 20, 2021

(54) POLYOXAZOLINE ANTIBODY DRUG CONJUGATES

(71) Applicant: Serina Therapeutics, Inc., Huntsville, AL (US)

(72) Inventors: Randall W. Moreadith, Huntsville, AL (US); Michael D. Bentley, Huntsville, AL (US); Zhihao Fang, Madison, AL (US); Tacey Viegas, Madison, AL (US)

(73) Assignee: Serina Therapeutics, Inc., Huntsville, AL (US)

( * ) Notice: Subject to any disclaimer, the term of this patent is extended or adjusted under 35 U.S.C. 154(b) by 29 days.

This patent is subject to a terminal disclaimer.

(21) Appl. No.: 16/126,798

(22) Filed: Sep. 10, 2018

(65) Prior Publication Data

US 2019/0000985 A1   Jan. 3, 2019

Related U.S. Application Data

(63) Continuation of application No. 14/815,718, filed on Jul. 31, 2015, now Pat. No. 10,071,168.

(60) Provisional application No. 62/031,382, filed on Jul. 31, 2014.

(51) Int. Cl.
| | | |
|---|---|---|
| A61K 47/60 | (2017.01) | |
| A61K 47/68 | (2017.01) | |
| A61K 47/54 | (2017.01) | |
| A61K 47/59 | (2017.01) | |

(52) U.S. Cl.
CPC ........ *A61K 47/6803* (2017.08); *A61K 47/557* (2017.08); *A61K 47/59* (2017.08); *A61K 47/60* (2017.08); *A61K 47/6849* (2017.08); *A61K 47/6883* (2017.08); *A61K 47/6889* (2017.08)

(58) Field of Classification Search
CPC ............ A61K 47/6803; A61K 47/6889; A61K 47/6883; A61K 47/60
USPC .................................................... 424/138.1
See application file for complete search history.

(56) References Cited

U.S. PATENT DOCUMENTS

| | | |
|---|---|---|
| 8,101,706 B2 | 1/2012 | Yoon |
| 8,383,093 B1 | 2/2013 | Moreadith |
| 8,501,899 B2 | 8/2013 | Yoon |
| 9,169,354 B2 | 1/2015 | Harris |
| 2009/0111756 A1 | 4/2009 | Doronina |
| 2011/0009594 A1 | 1/2011 | Yoon |
| 2011/0166063 A1 | 7/2011 | Bossard |
| 2013/0177521 A1 | 7/2013 | Moreadith |
| 2014/0011964 A1 | 1/2014 | Harris |

FOREIGN PATENT DOCUMENTS

| | | |
|---|---|---|
| WO | WO 2013/020005 A2 | 2/2013 |
| WO | WO2013/020005 A2 | 2/2013 |

OTHER PUBLICATIONS

Young, Lee W. "International Preliminary Report on Patentability and Written Opinion—International Application No. PCT/US2015/043297" dated Nov. 2, 2015; The International Searching Authority; pp. 1-10.

Li, Xiuling, et al. "Antibody conjugation via one and two C-terminal selenocysteines" Methods 65, 2014, pp. 133-138.

Langer, Miren, European Search Report (EP 15826412.7); dated Mar. 1, 2018.

Jaunarajs, Karen L. Eskow, "Rotigotine Polyoxazoline Conjugates SER-214 Provides Robust and Sustained Antiparkinsonian Benefits," Movement Disorders, vol. 28, No. 12, pp. 1675-1682.

*Primary Examiner* — Yan Xiao

(74) *Attorney, Agent, or Firm* — Bradley Arant Boult Cummings LLP

(57) ABSTRACT

In the present disclosure, polymer conjugates, including polymer-antibody-drug conjugates (polymer ADCs) are described, as well as the use of such conjugates to treat human disease. The polymer conjugates can contain a large number of polymer-bound agents, thus effectively increasing the drug antibody ration (DAR) of the antibody significantly beyond the currently available technology. This may be of particular importance when antibodies to low density antigens are used as target antibodies. The described polymer-ADCs have improved pharmacokinetics and solubility relative to traditional ADCs. The linker between agent and the polymer can be tailored to provide release of toxin at the desired site and under the desired conditions within the tumor. An additional feature of the polymer-ADCs of the current disclosure is that a purification moiety can be attached to the polymer backbone to provide ease of purification of the polymer-ADCs.

10 Claims, 4 Drawing Sheets

- CD79b-vc-MMAE
- CD79b-POZ-(vc-PAB-MMAE)$_1$
- CD79b-POZ-(vc-PAB-MMAE)$_5$
- CD79b-POZ-(vc-PAB-DC)$_6$
- CD79b-POZ-(pl-PAB-DC)$_5$

- CD79b-vc-MMAE
- CD79b-POZ-(vc-PAB-MMAE)1
- CD79b-POZ-(vc-PAB-MMAE)$_5$
- CD79b-POZ-(vc-PAB-DC)$_6$
- CD79b-POZ-(pl-PAB-DC)$_5$

POLYOXAZOLINE ANTIBODY DRUG CONJUGATES

CROSS-REFERENCE TO RELATED APPLICATIONS

This application is a continuation of U.S. application Ser. No. 14/815,718 (filed Jul. 31, 2015, now U.S. Pat. No. 10,071,168 (issued Sep. 11, 2018). U.S. application Ser. No. 14/815,718 cites the priority of U.S. Provisional Application No. 62/031,382 (filed Jul. 31, 2014).

BACKGROUND

Small molecule pharmaceuticals have long been the standard in treatment for a variety of diseases, including, but not limited to, cancer. Such small molecule pharmaceuticals are normally administered orally in the form of liquids, pills, capsule and the like or parenterally in the form of injectable or intravenous formulations. While effective in treating a great many conditions, many challenges remain. These include, but are not limited to, controlling the rate of drug delivery, targeting the delivery of the compounds to the desired site of action and maximizing the half-life of the compounds in the circulation. For example, many compounds exhibit decreased efficacy and therapeutic benefit due to metabolism prior to reaching the site of action. In addition, many compounds are relatively insoluble in aqueous solvents, requiring the use of complicated formulations for administration. In some instances, this may limit their usefulness clinically even though they are effective in pre-clinical studies.

One objective in the field of drug delivery is to preferentially deliver a compound to a desired site of action. Furthermore, an additional objective is control, at least partially, the delivery of the compound once the compound reaches the site of action. Still further, an additional objective is to accomplish one or more of the foregoing objectives with a delivery system that stabilizes the compound when delivered in vivo, extends the half-life of the compound in vivo and aids in solubilizing compounds, particularly those compounds that are insoluble in aqueous solvents.

In order to address the shortcomings in the art, antibody-drug conjugates (ADCs) have been explored. A great deal of research and development has shown that ADCs are effective at providing targeted destruction of cancer cells in animal models as well as in humans (P. D. Senter and E. L. Sievers, Nature Biotechnology, 30, 631-637 (2012); C&EN, Antibody Drug Conjugates, Jun. 18, 2012, pages 12-18; J. D. Thomas, et al., Bioconjugate Chem., 23, 2007-2013 (2012); and references therein). Although this concept had been discussed for many years, the realization of the concept took several decades to fulfill. The first "armed antibody" was not approved until 2011 (P. D. Senter and E. L. Sievers, Nature Biotechnology, 30, 631-637 (2012)). In its most common form one to four molecules of a drug or other compound (referred to here as an "agent") are coupled to an antibody using linker chemistry designed to release the agent into the tumor mass or into a tumor cell. One limitation of this approach is that insufficient toxin may be attached to the antibody to kill certain tumors, especially when less powerful toxins are used or when there is reduced antigen density present on the tumor cell surface. Also, increasing the number of points of toxin attachment on the antibody may compromise antibody binding capacity and decrease its ability to kill cancer cells. Additionally, this approach can be problematic with compounds that are difficult to solubilize. Finally, some toxins, when attached to antibodies, are so hydrophobic that they are taken up by off-target tissues independent of the binding region of the antibody—thus limiting their effective therapeutic potential.

Another approach is to use a biodegradable polymer such as the polyacetal derived from oxidized dextran (Yurokovetskiy et al, U.S. Pat. No. 8,685,383). In such an approach, the polymer-ADC may contain multiple copies of the agent linked to the polymer backbone with the polymer itself being linked to the antibody. A drug-antibody ratio (DAR) of greater than 1 allows for improved cytotoxicity results when compared to non-targeted polymer drug conjugates alone. Biodegradable polymers, such as the polyacetal above, have the advantage of degrading and thus avoiding accumulation in the body. However, they also have the disadvantage of degrading more quickly than desired, either during preparation or in the body after injection. This approach may lead to premature release of the cytotoxic agent during circulation, thus limiting its effectiveness before it reaches the antigen on the target cell. Secondly, many such polymers, including the polyacetal above, have a biological origin and this can lead to manufacturing challenges related to removing dangerous impurities, and it can increase the risk of adverse reactions when administered to a subject.

An additional approach has been to attach an antibody to a biocompatible polymer (referred to as a polymer-ADC). A simple approach is to attach a linear polymer such as polyethylene glycol (PEG) between the antibody and the drug. This was demonstrated by Riggs-Sauthier et al (US 2014/0088021), where one linear heterobifunctional PEG of either 2 kDa or 20 kDa is first attached to one thiol on the HER2 antibody by maleimide chemistry. The PEG antibody complex is then coupled with one cytotoxic small molecule through an ester linkage. This approach may have significant disadvantages because the ester link is not stable in-vivo and will hydrolyze to release the cytotoxic agent in blood before it reaches the antigen on the target cell. The in vivo efficacy study in this work was not able to demonstrate active targeting of the polymer-ADC when either a 2 kDa or a 20 kDa polymer was used. The efficacy that was demonstrated was likely due to a pharmacokinetic half-life extension of the cytotoxic agent due to the PEG moiety. In addition, the PEG polymer-ADCs lost bioactivity in the cytotoxicity assay when compared to the drug alone. The drug to antibody ratio (DAR) in this scenario is only one, offering no advantage over the non-polymer-ADC approach. The arming of multiple copies of either the drug or the antibody on the linear PEG polymer cannot be achieved with this approach.

In consideration of the foregoing, the field is in need of an ADC, in particular a polymer-ADC, which addresses the limitations described above. The present application provides a solution to these issues by providing a polymer-ADC that is of synthetic manufacture, provides for increased loading (higher DAR values) of the agent onto the targeting antibody, provides for increased half-life of the conjugate in vivo, and does not interfere substantially with the binding activity of the targeting agent (i.e., an antibody). Furthermore, the polymer-ADC conjugates of the present disclosure are readily constructed, and they can provide enhanced solubility of the compound to be delivered. Finally, the polymer-ADC conjugates of the present disclosure do not release drug until they reach the antigen on the target cell and are internalized, where the agent is released following cleavage from the polymer. In this application, HBL-2, MEC-1 and Ramos cells lines (human B-cell lymphoma-derived cell lines) are used as examples.

SUMMARY OF THE CURRENT INVENTION

Figure 1A:
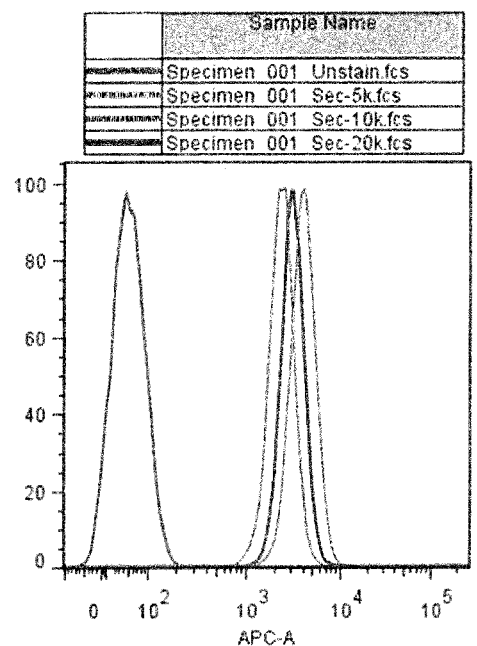
FIG. 1A shows flow cytometry plots of R11 POZ Biotin with HBL-2 cells.

In the present disclosure, polymer conjugates are described, as well as the use of such polymers to treat human disease. In one embodiment, the polymer conjugates are polymer-ADC's. In one embodiment, the polymer conjugates are biostable. In another embodiment, all or certain linkers are biostable. The polymer-ADCs are designed to contain a large number of polymer-bound agents (high DAR). These polymer-ADCs also can have a single point of attachment or multiple points of attachment between the recognition moiety (such as but not limited to an antibody) and the polymer, where the point or points of attachment can be remote from the binding site of the recognition moiety. In certain embodiments, a single recognition moiety may bind more than 1 polymer-ADC described herein. The described polymer-ADCs have improved pharmacokinetics and solubility relative to traditional ADCs. In addition these polymer-ADCs have the advantage of not degrading during preparation or during delivery. Furthermore, the polymer portion of the polymer ADCs is synthetic and is free of biological impurities. The linker between agent and the polymer can be tailored to provide release of toxin at the desired site and under the desired conditions at a site of action, such as a tumor cell. An additional feature of the polymer-ADCs of the current invention is that a purification moiety, such as but not limited to, biotin can be attached on the polymer backbone to provide ease of purification of the complex conjugates.

Definitions

As used herein, the term "agent" refers to any molecule having a therapeutic or diagnostic application, wherein the agent is capable of forming a linkage with a functional group on a polymer or a linking group attached to a polymer, the agent including, but not limited to, a therapeutic agent (such as but not limited to a drug), a diagnostic agent or an organic small molecule. In a specific embodiment, agent is useful in the treatment of cancer.

As used herein, the term "link", "linked" "linkage" or "linker" when used with respect to a polymer or agent described herein, or components thereof, refers to groups or bonds that normally are formed as the result of a chemical reaction. In certain embodiments, specific linkages are covalent linkages. In certain embodiments, specific linkages are hydrolyzable.

As used herein, the term "hydrolyzable linker" or "releasable, hydrolyzable linker" refers to a chemical linkage that is cleavable in a subject in vivo under specific physiological conditions in the subject after a conjugate of the present disclosure containing the hydrolyzable linker has been administered to the subject. In a further embodiment, the hydrolyzable linker may be biostable. A hydrolyzable linker may contain a hydrolyzable moiety as discussed herein; in certain circumstances a hydrolyzable linker may contain more than one hydrolyzable linker. In one embodiment, the hydrolyzable linker is cleavable on delivery to the site of action, such as, but not limited to, a tumor cell. In one embodiment, the hydrolyzable linker is cleavable only when taken up (for example by endocytosis) by a cell, such as, but not limited to, a tumor cell. In one embodiment, the hydrolyzable linker is cleavable in a lysosome or endosome. In one embodiment, the hydrolyzable linker is cleaved by a chemical reaction. In aspect of this embodiment, the cleavage is by reduction of an easily reduced group, such as, but not limited to, a disulfide or a self-emolative reaction. In one embodiment, the hydrolyzable linker is cleaved by a substance that is naturally present or induced to be present in the subject. In an aspect of this embodiment, such a substance is an enzyme or polypeptide. Therefore, in one embodiment, the hydrolyzable linker is cleaved by an enzymatic reaction. In one embodiment, the hydrolyzable linker is cleaved by a combination of the foregoing. In one embodiment, the hydrolyzable moiety contained within the hydrolyzable linker is cleaved under the same conditions and by the same mechanisms.

As used herein the term "biostable" refers to a polymer or polymer conjugate (including any linkers or linkages, such as but not limited to a hydrolyzable linker, contained therein) that is resistant to cleavage when administered to a subject, including a human subject, until the polymer or polymer conjugate reaches the site of action (such as, but not limited to, a tumor cell). By "resistant to cleavage" it is meant that at least 80%, 90%, 95%, 98% or 99% or more of the polymer or polymer conjugate is not cleaved until the polymer reaches the site of action. In one embodiment, a biostable polymer or polymer conjugate is resistant to cleavage in the bloodstream of the subject, such that over 80%, 90%, 95%, 98%, 99% or more of the polymer or polymer conjugate is not cleaved in the bloodstream. The term biostable" may also refers to a linker or linkage, such as but not limited to a hydrolyzable linker, such that the linker or linkage is resistant to cleavage when administered to a subject, including a human subject, until the linker of linkage is placed at the site of action (such as, but not limited to, a tumor cell). Therefore, in one embodiment, a biostable linker or linkage is resistant to cleavage in the bloodstream of the subject, such that over 80%, 90%, 95%, 98%, 99% or more of the linker or linkage is not cleaved in the bloodstream.

As used herein, the term "alkyl", whether used alone or as part of a substituent group, includes straight hydrocarbon groups comprising from one to twenty carbon atoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$) (CH$_2$CH$_3$), —CH(CH$_2$CH$_3$)$_2$, —C(CH$_3$)$_3$, C(CH$_2$CH$_3$)$_3$, —CH$_2$CH(CH$_3$)$_2$, —CH$_2$CH(CH$_3$)(CH$_2$CH$_3$), —CH$_2$CH (CH₂CH₃)₂, —CH₂C(CH₃)₃, —CH₂C(CH₂CH₃)₃, —CH(CH₃)CH(CH₃)(CH₂CH₃), —CH₂CH₂CH(CH₃)₂, —CH₂CH₂CH(CH₃)(CH₂CH₃), —CH₂CH₂CH(CH₂CH₃)₂, —CH₂CH₂C(CH₃)₃, —CH₂CH₂C(CH₂CH₃)₃, —CH(CH₃)CH₂CH(CH₃)₂, —CH(CH₃)CH(CH₃)CH(CH₃)CH(CH₃)₂, —CH(CH₂CH₃)CH(CH₃)CH(CH₃)(CH₂CH₃), and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo[2.2.2]octyl and such rings substituted with straight and branched chain alkyl groups as defined above.

As used herein, the term "alkenyl", whether used alone or as part of a substituent group, includes an alkyl group having at least one double bond between any two adjacent carbon atoms.

As used herein, the term "alkynyl", whether used alone or as part of a substituent group, includes an alkyl group having at least one triple bond between any two adjacent carbon atoms.

As used herein, the term "unsubstituted alkyl", "unsubstituted alkenyl" and "unsubstituted alkynyl" refers to alkyl, alkenyl and alkynyl groups that do not contain heteroatoms.

As used herein, the term "substituted alkyl", "substituted alkenyl" and "unsubstituted alkynyl" refers to alkyl alkenyl and alkynyl groups as defined above in which one or more bonds to a carbon(s) or hydrogen(s) are replaced by a bond to non-hydrogen or non-carbon atoms such as, but not limited to, an oxygen atom in groups such as alkoxy groups and aryloxy groups; a sulfur atom in groups such as, alkyl and aryl sulfide groups, sulfone groups, sulfonyl groups, and sulfoxide groups; a silicon atom in groups such as in trialkylsilyl groups, dialkylarylsilyl groups, alkyldiarylsilyl groups, and triarylsilyl groups; and other heteroatoms in various other groups.

As used herein, the term "unsubstituted aralkyl" refers to unsubstituted alkyl or alkenyl groups as defined above in which a hydrogen or carbon bond of the unsubstituted or substituted alkyl or alkenyl group is replaced with a bond to a substituted or unsubstituted aryl group as defined above. For example, methyl (CH₃) is an unsubstituted alkyl group. If a hydrogen atom of the methyl group is replaced by a bond to a phenyl group, such as if the carbon of the methyl were bonded to a carbon of benzene, then the compound is an unsubstituted aralkyl group (i.e., a benzyl group).

As used herein, the term "substituted aralkyl" has the same meaning with respect to unsubstituted aralkyl groups that substituted aryl groups had with respect to unsubstituted aryl groups. However, a substituted aralkyl group also includes groups in which a carbon or hydrogen bond of the alkyl part of the group is replaced by a bond to a non-carbon or a non-hydrogen atom.

As used herein, the term "unsubstituted aryl" refers to monocyclic or bicyclic aromatic hydrocarbon groups having 6 to 12 carbon atoms in the ring portion, such as, but not limited to, phenyl, naphthyl, anthracenyl, biphenyl and diphenyl groups, that do not contain heteroatoms. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. Unsubstituted aryl groups may be bonded to one or more carbon atom(s), oxygen atom(s), nitrogen atom(s), and/or sulfur atom(s) in the parent compound, however.

As used herein, the term "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms, such as, but not limited to, those atoms described above with respect to a substituted alkyl, and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl or alkenyl, group to define a fused ring system (e.g. dihydronaphthyl or tetrahydronaphthyl). Thus, the phrase "substituted aryl" includes, but is not limited to tolyl, and hydroxyphenyl among others.

As used herein, the term "unsubstituted heterocyclyl" refers to both aromatic and nonaromatic ring compounds including monocyclic, bicyclic, and polycyclic ring compounds containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members, as compounds such as 2-methylbenzimidazolyl are "substituted heterocyclyl" groups as defined below. Examples of heterocyclyl groups include, but are not limited to: unsaturated 3 to 8 membered rings containing 1 to 4 nitrogen atoms, condensed unsaturated heterocyclic groups containing 1 to 4 nitrogen atoms, unsaturated 3 to 8 membered rings containing 1 to 2 oxygen atoms and 1 to 3 nitrogen atoms, saturated 3 to 8 membered rings containing 1 to 2 oxygen atoms and 1 to 3 nitrogen atoms such, unsaturated condensed heterocyclic groups containing 1 to 2 oxygen atoms and 1 to 3 nitrogen atoms, unsaturated 3 to 8 membered rings containing 1 to 3 sulfur atoms and 1 to 3 nitrogen atoms, saturated 3 to 8 membered rings containing 1 to 2 sulfur atoms and 1 to 3 nitrogen atoms, saturated and unsaturated 3 to 8 membered rings containing 1 to 2 sulfur atoms, unsaturated condensed heterocyclic rings containing 1 to 2 sulfur atoms and 1 to 3 nitrogen atoms, unsaturated 3 to 8 membered rings containing oxygen atoms, unsaturated condensed heterocyclic rings containing 1 to 2 oxygen atoms, unsaturated 3 to 8 membered rings containing an oxygen atom and 1 to 2 sulfur atoms, saturated 3 to 8 membered rings containing 1 to 2 oxygen atoms and 1 to 2 sulfur atoms, unsaturated condensed rings containing 1 to 2 sulfur atoms, and unsaturated condensed heterocyclic rings containing an oxygen atom and 1 to 2 oxygen atoms. Heterocyclyl group also include those described above in which one or more S atoms in the ring is double-bonded to one or two oxygen atoms (sulfoxides and sulfones).

As used herein, the term "substituted heterocyclyl" has the same meaning with respect to unsubstituted heterocyclyl groups that substituted alkyl groups had with respect to unsubstituted alkyl groups. However, a substituted heterocyclyl group also includes heterocyclyl groups in which one of the carbons is bonded to one of the non-carbon or non-hydrogen atom, such as, but not limited to, those atoms described above with respect to a substituted alky and substituted aryl groups and also includes heterocyclyl groups in which one or more carbons of the heterocyclyl group is bonded to a substituted and/or unsubstituted alkyl, alkenyl or aryl group as defined herein. This includes bonding arrangements in which two carbon atoms of an heterocyclyl group are bonded to two atoms of an alkyl, alkenyl, or alkynyl group to define a fused ring system. Examples, include, but are not limited to, 2-methylbenzimidazolyl, 5-methylbenzimidazolyl, 5-chlorobenzthiazolyl, 1-methyl piperazinyl, and 2-chloropyridyl among others.

As used herein, the term "unsubstituted heterocylalkyl" refers to unsubstituted alkyl or alkenyl groups as defined above in which a hydrogen or carbon bond of the unsubstituted alkyl or alkenyl group is replaced with a bond to a substituted or unsubstituted heterocyclyl group as defined above. For example, methyl ($CH_3$) is an unsubstituted alkyl group. If a hydrogen atom of the methyl group is replaced by a bond to a heterocyclyl group, such as if the carbon of the methyl were bonded to carbon 2 of pyridine (one of the carbons bonded to the N of the pyridine) or carbons 3 or 4 of the pyridine, then the compound is an unsubstituted heterocyclylalkyl group.

As used herein, the term "substituted heterocylalkyl" has the same meaning with respect to unsubstituted heterocyclylalkyl groups that substituted aryl groups had with respect to unsubstituted aryl groups. However, a substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group.

For simplicity, chemical moieties are defined and referred to throughout can be monovalent chemical moieties (e.g., alkyl, aryl, etc.). Such monovalent chemical moieties under the appropriate structural circumstances clear to those skilled in the art encompass divalent moieties. For example, an "alkyl" moiety is defined herein as a monovalent radical (e.g., $CH_3-CH_2-$), however under the appropriate structural circumstances clear to those skilled in the art, "alkyl," can a divalent radical (e.g., $-CH_2-CH_2-$), which is equivalent to the term "alkylene." Similarly, in circumstances in which divalent moieties are required and are defined as being monovalent (for example "alkoxy", "alkylamino", "aryloxy", "alkylthio", "aryl", "heteroary", "heterocyclic", "alkenyl", "alkynyl", "aliphatic", or "cycloalkyl"), those skilled in the art will understand that the terms refer to the corresponding divalent moiety.

As used herein, the terms "treatment", "treat" and "treating" refers a course of action (such as administering a conjugate or pharmaceutical composition) initiated after the onset of a symptom, aspect, or characteristics of a disease or condition so as to eliminate or reduce such symptom, aspect, or characteristics. Such treating need not be absolute to be useful.

As used herein, the term "in need of treatment" refers to a judgment made by a caregiver that a patient requires or will benefit from treatment. This judgment is made based on a variety of factors that are in the realm of a caregiver's expertise, but that includes the knowledge that the patient is ill, or will be ill, as the result of a disease or condition that is treatable by a method or compound of the disclosure.

As used herein, the term "in need of prevention" refers to a judgment made by a caregiver that a patient requires or will benefit from prevention. This judgment is made based on a variety of factors that are in the realm of a caregiver's expertise, but that includes the knowledge that the patient will be ill or may become ill, as the result of a disease or condition that is preventable by a method or compound of the disclosure.

As used herein, the term "individual", "subject" or "patient" refers to any animal, including mammals, such as mice, rats, other rodents, rabbits, dogs, cats, swine, cattle, sheep, horses, or primates, and humans. The term may specify male or female or both, or exclude male or female.

As used herein, the term "therapeutically effective amount" refers to an amount of a conjugate, either alone or as a part of a pharmaceutical composition, that is capable of having any detectable, positive effect on any symptom, aspect, or characteristics of a disease or condition. Such effect need not be absolute to be beneficial.

Polyoxazoline Polymer

Polyoxazolines (POZ) are polymers prepared from 2-substituted-2-oxazoline monomers. These polymers are water soluble and have been reported to be nontoxic in mammalian model systems. POZ is generally prepared by reaction of the appropriate stoichiometric amount of 2-alkyl-2-oxazoline with an electrophilic initiator, such as methyl triflate ($CH_3-OSO_2-CF_3$) or a strong acid such as triflic acid or p-toluenesulfonic acid, followed by termination with a nucleophile such as, but not limited to, hydroxide, a thiol or an amine. The polymer produced is conveniently described in shorthand with the initiating group designated by the leftmost group and the terminating group designated by the rightmost group, with the 2-alkyl-2-oxazoline component in the middle. Therefore, when this shorthand description is used in the current specification, it is intended that the left side of the designation presents the "initiator end" and the right side of the designation presents the "termination end", unless designated otherwise.

For example, when the 2-alkyl-2-oxazoline is 2-methyl-2-oxazoline, methyl triflate is used as the initiator and hydroxide is used as the terminator, the following POZ is produced:

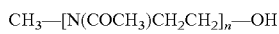

$CH_3-[N(COCH_3)CH_2CH_2]_n-OH$

The polymer above is conveniently described in shorthand notation as M-PMOZ—OH, in which the methyl initiator is designated by the leftmost M, PMOZ represents polymethyloxazoline with the methyl of the repeating unit designated by the M of PMOZ, and the terminating hydroxyl is designated by the —OH.

Another commonly used monomer is 2-ethyl-2-oxazoline, which with methyl triflate initiation and hydroxide termination would provide the following POZ polymer:

$CH_3-[N(COCH_2CH_3)CH_2CH_2]_n-OH$

The polymer above is conveniently described in shorthand notation as M-PEOZ—OH, in which the methyl initiator is designated by the leftmost M, PEOZ represents polymethyloxazoline with the ethyl of the repeating unit designated by the E of PEOZ, and the terminating hydroxyl is designated by the —OH.

The degree of polymerization, n, for well characterized polymers can range from approximately 3 to over 1000.

The polymerization process is referred to as a living, cationic polymerization since initiation with an electrophile produces an oxazolinium cation that then reacts in a chain reaction with additional monomer units to produce a growing, "living" cation.

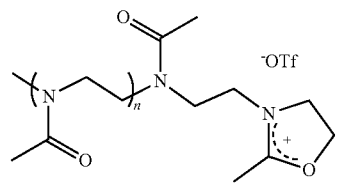

One can predict the products of termination by assuming that the living cation can be represented in the following non-cyclic form (for polymerization of 2-methyl-2-oxazoline initiated with methyl triflate), although in reality the cyclic form is certainly the most important:

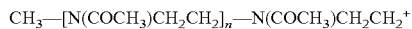

In the current discussion we will represent this cation as M-PMOZ⁺. As noted above, this POZ cation can be "terminated" by reacting with nucleophiles such as hydroxide, thiols or amines.

Oxazoline polymerization can also be initiated with functional electrophiles. For example the electrophilic initiator ethyl 3-bromopropionate has been used to initiate 2-ethyl-2-oxazoline polymerization. Termination with hydroxide gives the following polymer:

Yet another route to preparing polyoxazolines with functional groups is to copolymerize a monomer such as 2-ethyl-2-oxazoline with an oxazoline monomer having a functional group in the 2-position (F. C. Gaertner, R. Luxenhofer, B. Blechert, R. Jordan and M. Essler, J. Controlled Release, 2007, 119, 291-300). For example, Jordan and colleagues have prepared oxazolines with acetylenes and protected aldehydes, carboxylic acids and amines in the 2-position. Copolymerization of these functional monomers with 2-ethyl-2-oxazoline gives random copolymers with multiple pendent or side-chain functional groups. For example, initiation with methyl triflate of polymerization of 2-ethyl-2-oxazoline and 2-pentynyl-2-oxazoline, followed by termination with piperazine (NHC₄H₈NH) gives the following random copolymer:

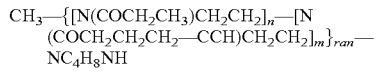

The subscript "ran" indicates that the polymer is a random copolymer. Values of n are typically around 20-30 while m is around 2-5.

These copolymers with pendent functional groups and a terminal functional group are useful in that the pendent and terminal functional groups can be "chemically orthogonal" functional groups. Chemically orthogonal functional groups are those functional groups that will not react with each other but will react selectively with other functional groups. For example, the molecule above has two functional groups, a terminal secondary amine and pendent acetylenes. The acetylene will not react with the amine but will, for example, react with an azide group (—N₃). Similarly, the amine will not react with acetylene or azide but will react with, for example, an isothiocyanate group (—NCS). Jordan has used this copolymer to couple an azide-functionalized RGD peptide to the acetylene group, and an isothiocyanate-functionalized metal chelator to the amine. The RGD peptide is known to target tumors, and a diagnostic or therapeutic radionuclide can bind to the chelating group. The final conjugate can be used to image or treat tumors (R. Luxenhofer, M. Lopez-Garcia, A. Frannk, H. Kessler and R. Jordan, Proceedings of the American Chemical Society, PMSE Prepr. 2006, 95, 283-284).

One problem hindering use of the polyoxazoline polymers of the prior art, including the above-mentioned piperazine- or piperidine-terminated polyoxazolines, is that they are difficult to purify. This difficulty arises because contaminating water present during termination leads to nucleophilic attack by water and consequent formation of secondary amine impurity (O. Nuyken, G. Maier, A. Gross, Macromol. Chem. Phys. 197, 83-95, 1996). Since the products from piperazine and piperidine termination always contain a tertiary amine, ion-exchange chromatography cannot be used to remove the contaminating secondary amine.

Still another limitation of the pendent polyoxazolines illustrated above is that these compounds possess a single terminal functional group. Consequently, this structural configuration limits the number of drug or targeting moieties that can be attached to the terminus, whereas effective use of such compounds for therapeutic diagnostic and targeting applications may require multiple loading of these moieties. The polymers of the current disclosure avoid this limitation by providing for multiple copies of each of two chemically reactive and orthogonal functional groups.

Polyoxazoline Polymer-Antibody Conjugates

A number of polyoxazoline polymers may be used in the present invention. Such polymers are described in U.S. Pat. Nos. 8,110,651; 8101,706 and 8,383,093 and PCT Application No. PCT/US2012/063088 (each of which are hereby incorporated by reference for such teachings). In one embodiment, the polyoxazoline polymer for use in the ADCs described carries 2 or more agents, such as, but not limited to, a cytotoxic agent. In one embodiment, the polyoxazoline polymer for use in the ADCs described carries 5 or more agents, such as, but not limited to, a cytotoxic agent. In another embodiment, the polyoxazoline polymer for use in the ADCs described carries 8 or more agents, such as, but not limited to, a cytotoxic agent. In one embodiment, the polyoxazoline polymer for use in the ADCs described carries 10 or more agents, such as, but not limited to, a cytotoxic agent. In each of the foregoing embodiments, the agent may be the same or the agent(s) may be different (for example, two cytotoxic compounds that act sequentially in a pathway to inhibit the growth of cancer). In one embodiment, the agent is the same. Representative agents are described herein. In one embodiment, the polyoxazoline polymer may be a heterofunctional polymer that carries 3 or more, 5 or more, 8 or more, 20 or more or 40 or more agents, such as, but not limited to, a cytotoxic agent, as described.

In one embodiment, the polyoxazoline-antibody conjugate comprises a polyoxazoline linked to a recognition moiety, wherein the recognition moiety comprises a binding residue, the polyoxazoline comprises a plurality of agents and the polyoxazoline is linked to the recognition agent at the binding residue. A composition comprising the polyoxazoline-antibody conjugate and a pharmaceutically acceptable carrier is also provided.

In one embodiment, the recognition moiety is an antibody or an antibody fragment, such as, but not limited to, a single chain antibody. In a further embodiment, the recognition moiety is an antibody or an antibody fragment, such as, but not limited to, a single chain antibody, and the binding residue is a stoichiometric biding residue wherein the polyoxazoline polymer and the antibody are bound at the stoichiometric biding residue in a 1:1 ratio. In a further embodiment, the recognition moiety is an antibody or an antibody fragment, such as, but not limited to, a single chain antibody, and the binding residue is a selenocysteine residue wherein the polyoxazoline polymer and the antibody are bound at the selenocysteine residue in a 1:1 ratio. In a further embodiment, the recognition moiety is a single chain antibody, and the binding residue is a selenocysteine residue wherein the polyoxazoline polymer and the single chain antibody are bound at the selenocysteine residue in a 1:1 ratio. In certain embodiment, multiple polyoxazoline polymers may be bound to a single recognition moiety as described. In certain embodiments, 2, 4, 6, 8 or 10 polyoxazoline polymers are bound to a single recognition moiety at distinct location. In certain embodiments, 2, 3, 4 or 5 polyoxazoline polymers are bound to a single recognition moiety at distinct location.

In one embodiment, the polyoxazoline conjugate is represented by the general structure:

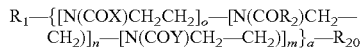

$$R_1—\{[N(COX)CH_2CH_2]_o—[N(COR_2)CH_2—CH_2)]_n—[N(COY)CH_2—CH_2)]_m\}_a—R_{20}$$

wherein:

$R_1$ is an initiating group;

$R_2$ is a non-reactive pendant moiety.

X for each repeating unit is a first pendent moiety, wherein at least one first pendent moiety contains an agent or a purification moiety and links the agent or the purification moiety to the polymer backbone;

Y for each repeating unit is a second pendent moiety, wherein each second pendent moiety optionally contains the agent or the purification moiety and links the agent or the purification moiety to the polymer backbone;

$R_{20}$ is a recognition agent linking moiety containing the recognition moiety and linking the recognition moiety to the polymer backbone;

a is ran which indicates a random copolymer or block which indicates a block copolymer;

n is an integer from 0 to 1000; and o and m are each an integer independently selected from 0-50, provided that both o and m are not each 0 and the total of n, o and m is at least 30 and that at least one agent is present.

In the polymer conjugate described, the agent may be independently selected for each repeating unit such that more than 1 type of agent is present in the polymer conjugate. Likewise, the purification moiety may be independently selected for each repeating unit such that more than 1 type of purification moiety is present in the polymer conjugate. In certain embodiments, only 1 type of agent and 1 type of purification moiety are present. In certain embodiments, 2 types of agent and 1 type of purification moiety are present. As discussed herein, in certain embodiments the agent and/or purification moiety (which may include a portion of the first and second pendent moieties) can be synthesized independently and linked to the polymer conjugate, wherein the number of such pendent moieties linked can be controlled by the molar ratio of the pendent moieties thereby allowing addition of multiple types of agents and/or purification moieties in a single reaction. Other combinations are also within the scope of the present disclosure.

In one embodiment, one of o and m are 0 and the other of o or m is 3, 5, 8, 10, 15, 20, 30, 40 or more up to 50 and the total of o, m and n is from 20 to 1000, 30 to 500, from 30 to 250 or from 30 to 100. In one embodiment, one of o and m are 0 and the other of o or m is greater than or equal to 5 and less than or equal to 20 and the total of o, m and n is from 20 to 1000, 30 to 500, from 30 to 250 or from 30 to 100. In one embodiment, one of o and m are 0 and the other of o or m is greater than or equal to 5 and less than or equal to 15 and the total of o, m and n is from 20 to 1000, 30 to 500, from 30 to 250 or from 30 to 100. In one embodiment, one of o and m are 0 and the other of o or m is greater than or equal to 5 and less than or equal to 10 and the total of o, m and n is from 20 to 1000, 30 to 500, from 30 to 250 or from 30 to 100. In one embodiment, of any of the foregoing, m rather than being 0 can be from 1 to 50, 1 to 30, 1 to 20, 1 to 15, 1 to 10 or 1 to 5. In one embodiment, of any of the foregoing, m rather than being 0 can be from 1 to 50, 1 to 30, 1 to 20, 1 to 15, 1 to 10 or 1 to 5 and all or a portion of the second pendant moieties lack an agent or purification moiety.

In one embodiment, 1 to 10, 1 to 4 or 1-2 purification moieties are present. As discussed herein, such purification moieties may be contained in X and/or Y. The purification moieties may be the same or they may be different. In one embodiment, 2 to 20, 2 to 15, 2 to 10 or 2 to 7 agents are present. In one embodiment, 2, 3, 4, 5, 6, 7, 8, 9, or 10 agents are present. In one embodiment, up to 40 agents are present. As discussed herein, such agents may be contained in X and/or Y. The agents may be the same or they may be different. In certain structures disclosed herein, the number of purification moieties present in the conjugate is indicated by the of designation and the number of agents present in the conjugate is indicated by the o2 designation.

The number of agents and/or purification moieties linked the conjugate is less than or equal to the sum of o and m. For example, if the sum of o and m is fifteen, the maximum number of agents and/or purification moieties linked to the polymer is 15. In certain embodiments, the number of agents and/purification moieties linked to the conjugate is less than the sum of o and m, meaning that in certain embodiments a free first and/or second pendent moiety is present. Therefore, not every pendent moiety is required to contain an agent and/or purification moiety. In certain embodiments, conjugate has a DAR of 2 to 40, 2 to 20, 5 to 20, 10 to 20 or 20 to 40. In certain embodiments, the conjugate has a DAR of 2, 3, 4, 5, 6, 7, 8, 9 or 10.

The nature of the first and second pendent moieties can vary provided groups have the structure for linkage with an agent and/or purification moiety and the polymer. Representative structures for the first and second pendent moieties are described herein. In one embodiment, the first and second pendent moieties each contain a functional group (i.e., a first and second functional group). The functional group is involved in the linkage to the agent and/or purification moiety to the polymer as described herein. In one embodiment, the first and second functional groups are chemically orthogonal to one another allowing the use of distinct reaction chemistry to agents and/or purification moieties to the polymer. The first and second functional groups include, but are not limited to, alkyne, amine, oxyamine, aldehyde, ketone, acetal, ketal, maleimide, ester, carboxylic acid, activated carboxylic acid (such as, but not limited to, N-hydroxysuccinimidyl (NHS) and 1-benzotriazineyl active ester), an active carbonate, a chloroformate, alcohol, azide, vinyl sulfone, or orthopyridyl disulfide (OPSS). In addition, the first and second pendent moieties may contain additional groups linking the functional groups to the polymer backbone such as, but not limited to, an unsubstituted or substituted alkyl, an unsubstituted or substituted alkenyl, an unsubstituted or substituted aralkyl or an unsubstituted or substituted heterocyclylalkyl group. In certain embodiments, the first and/or second functional group is an alkyne. In certain embodiments, at least one of the first and or second pendent moieties is not linked to an agent or a purification moiety.

In certain embodiments, the polymer conjugate is a biostable polymer conjugate. In certain embodiments, the first and/or second pendent moieties are biostable. In certain embodiments, the first and/or second pendent moieties comprise a hydrolyzable linker containing a hydrolyzable moiety and the hydrolyzable linker and hydrolyzable moiety are biostable.

$R_2$ is a non-reactive pendant moiety. As such, $R_2$ lacks a functional group; in one embodiment, $R_2$ is independently selected for each repeating unit from an unsubstituted or substituted alkyl, an unsubstituted or substituted alkenyl, an unsubstituted or substituted aralkyl or an unsubstituted or substituted heterocyclylalkyl group. In another embodiment, R2 is an unsubstituted or substituted alkyl for 1 to 10 or 1 to 5 carbons in length.

Exemplary initiating groups include, but are not limited to, hydrogen, alkyl, substituted alkyl, aralkyl, or substituted aralkyl groups. In a particular embodiment, the initiating group is a methyl group. In one embodiment, the $R_1$ group is selected to lack a functional group. Additional exemplary initiating groups are disclosed in PCT Application No. PCT/US2008/078159, which is hereby incorporated by reference for such teaching.

In one embodiment, the polymer-conjugate may be represented by the general structure:

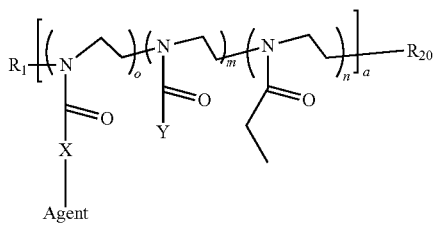

wherein the agent is any agent described herein, X represents the first pendent moiety and Y represents the second pendent moiety. In one embodiment of the foregoing, o is from 3-15, m is from 1 to 45 and the total of n, m and o is from 30 to 500 (or any sub-range therein or described herein). In this embodiment, the second pendent moiety Y is shown as lacking attachment to an agent or purification moiety. Furthermore, the non-reactive pendent group in this embodiment is shown as ethyl for simplicity, it being understood any groups described for $R_2$ may be present. When a pendent moiety is not linked to an agent or purification moiety, such as Y above, the pendent moiety may be an alkyne (as well as other groups described herein). For example, when Y is an alkyne, the polymer conjugate may have the structure:

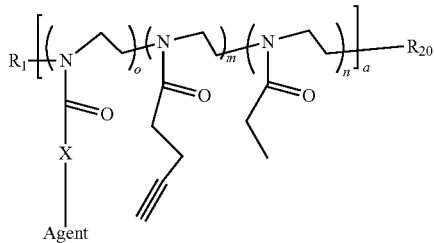

In one embodiment, the polymer conjugate may be represented by the general structure:

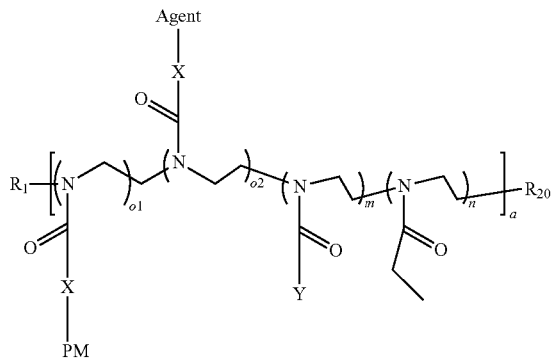

wherein the agent is any agent described herein, PM represents a purification moiety, X represents the first pendent moiety and Y represents the second pendent moiety. In one embodiment of the foregoing, of is from 1 to 4, is from 3-15, m is from 1 to 45 and the total of n, m and o is from 30 to 500 (or any sub-range therein or described herein). In this embodiment, the second pendent moiety Y is shown as lacking attachment to an agent or purification moiety. Furthermore, the non-reactive pendent group in this embodiment is shown as ethyl for simplicity, it being understood any groups described for $R_2$ may be present. When a pendent moiety is not linked to an agent or purification moiety, such as Y above, the pendent moiety may be an alkyne (as well as other groups described herein). For example, when Y is an alkyne, the polymer conjugate may have the structure:

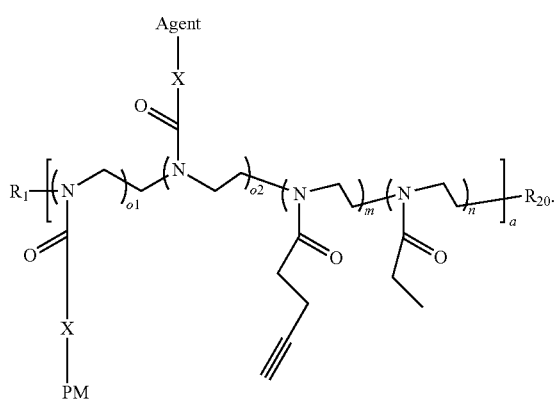

The number of agents and purification moieties may be controlled during synthesis of the conjugate through regulation of the intermediates as described in the examples. In one embodiment, the reaction chemistry for the addition of the agent and purification moiety (if present) is the same. In another embodiment, the reaction chemistry is different. For example, if the reaction chemistry is the same and 2 purification moieties and 6 agents are desired in the final conjugate, during the conjugation reactions 2 molar equivalents of the pendent moiety containing the purification moiety and 6 molar equivalents of the pendent moiety containing the agent are added to the reaction mixture, resulting in the desired structure. When an agent and a purification moiety are present, the nature of the pendent linking moiety may be the same or may be different. In other words, the nature of the first pendent linker may be the same or different as described herein. Furthermore, as described herein, the nature of the X and Y pendent linking moieties may be such that the reactive groups present provide for orthogonal functional groups, allowing the attachment of the agent and the purification moiety via different reaction chemistries.

Any purification moiety known in the art may be used in the polymer conjugates described herein. In one embodiment the purification moiety is biotin. In one embodiment from 1 to three biotin molecules are present in the conjugate. In one embodiment, 2 biotin molecules are present.

In one embodiment, the agent is linked to the poly (oxazoline) polymer by a releasable, hydrolyzable linkage (i.e., the first and/or second pendent moiety is a hydrolyzable linker). In such a case, the first and/or second pendent moiety contains at least one hydrolyzable moiety allowing the linkage to be cleaved after administration of the poly (oxazoline) polymer conjugate to a subject. The first and/or second pendent moiety may contain a single hydrolyzable moiety or more than one hydrolyzable moiety. The hydrolyzable moiety may be cleavable by an enzyme or through chemical reaction. In examples, where more than one hydrolyzable moiety is present, one hydrolyzable moiety may be cleavable by an enzyme and one hydrolyzable moiety may be cleavable through chemical reaction or all may be cleaved by the same mechanisms. In one embodiment, the first and/or second pendent moiety contains 1 hydrolyzable moiety. In another embodiment, the first and/or second pendent moiety contains 2 hydrolyzable moieties. In another embodiment, the first and/or second pendent moiety contains 2 hydrolyzable moieties wherein 1 such moiety is cleavable by an enzyme.

In one embodiment, the purification moiety is linked to the poly(oxazoline) polymer by a stable (the linkage is not cleaved even at the site of action) or hydrolyzable linker. As such, when agent and the purification moiety are each linked to the polymer by the same reaction chemistry (i.e., the first pendent moiety is used to link both the agent and the purification moiety using the same reaction chemistry), a portion of the first pendent moieties may contain a hydrolyzable moiety and a portion of the first pendent moieties may contain a stable linkage. In another embodiment, the purification moiety is linked to the polyoxazoline polymer by a releasable, hydrolyzable linkage as described herein. The hydrolyzable linker may be biostable in certain embodiment. As such, when agent and the purification moiety are each linked to the polymer by the same reaction chemistry (i.e., the first pendent moiety is used to link both the agent and the purification moiety using the same reaction chemistry), all linkages of the agent and purification moiety contain a hydrolyzable moiety. However, the nature of the hydrolyzable moiety may vary between the agent and the purification moiety if desired.

A number of enzymes may be used to cleave a hydrolyzable moiety. In one embodiment, the enzyme responsible for cleavage is absent in the blood or plasma. In one embodiment, the enzyme responsible for cleavage is present in a cellular compartment, such as, but not limited to, the lysosome or the endosome. In a particular embodiment, the enzyme is a peptidase, such as, but not limited to a cathepsin. A representative cathepsin is cathepsin B. In a particular embodiment, the hydrolyzable linkage and the hydrolyzable moiety are biostable in blood or plasma such that the agent and/or purification moiety is not released to a significant amount in the bloodstream. In one embodiment, the hydrolyzable moiety cleaved by an enzyme is an amide bond and such amide bond may be contained in an amino acid sequence.

Exemplary hydrolyzable moieties include, but are not limited to, carboxylate esters (—C(O)—O—), carbonate esters (—O—C(O)—O—), carbamates (—O—C(O)—NH—), disulfides (—S—S—), sulfides (—S—), acetals (—CH(OR')(OR")), hemiacetals (—CH(OR')(OH)), phosphates (—O—P(O)(OH)—(O)—), phosphonates (—O—P(O)(OR')—(O)—) and amides (—C(O)—NH—); other hydrolyzable moieties are discussed herein, wherein R' and R" are H or substituted or unsubstituted alkyl. In a particular embodiment, the hydrolyzable moiety is an ester. In another particular embodiment, the hydrolyzable moiety is an amide. In addition, the releasable, hydrolyzable linkage may be contained in a naturally occurring amino acid, a non-naturally occurring amino acid or a polymer linked to one or more naturally occurring and/or non-naturally occurring amino acids.

In one embodiment, the releasable, hydrolyzable linkage is a di-substituted triazole that contains a hydrolyzable moiety in one of the $R_3$ or $R_4$ groups. In one embodiment, the hydrolyzable moiety is in the $R_4$ group. In a specific embodiment, the di-substituted triazole has the structure:

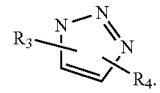

In another embodiment, the di-substituted triazole has the structure:

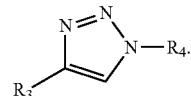

In each of the foregoing structures:

$R_3$ is a linker linking the triazole moiety to the polymer chain. In one embodiment, $R_3$ is defined (at least in part) by the functional group on the polymer chain. In one embodiment, $R_3$ is —$R_5$— or —C(O)—$R_5$—, where $R_5$ is absent or is a substituted or unsubstituted alkyl from 1 to 10 carbons in length. In one embodiment, $R_5$ is an unsubstituted alkyl of 1 to 10 carbons in length. In one embodiment, $R_5$ is an unsubstituted alkyl of 1 to 5 carbons in length.

$R_4$ forms a linkage between the triazole moiety and the agent. The nature of the R group may vary provided the linking function is accomplished in a releasable manner (i.e., the linkage contains a hydrolyzable moiety). In one embodiment, $R_4$ contains an alkyl portion. In another embodiment, $R_4$ contains a polymer portion. In another embodiment, $R_4$ contains one or more amino acids. In another embodiment, $R_4$ contains a polymer portion and one or more amino acids, wherein the hydrolyzable moiety is an amide bond in the amino acid portion. Suitable polymers include any water soluble polymers known in the art or described herein. In one embodiment, the water soluble polymer is a polyethylene glycol (PEG) polymer represented by —(O—$CH_2$—$CH_2$)$_s$—, wherein s is an integer from 1 to 15, from 1 to 10 or from 1 to 5. Specific values for s include, but are not limited to 2, 3, 4 and 5.

In one embodiment, $R_4$ is is —$R_6$-$R_7$-$R_8$—, wherein $R_6$ is a substituted or unsubstituted alkyl, a substituted or unsubstituted aralkyl, a polymer or U1-(pol)$_b$-U2-([$NR_{16}$—C($R_{13}$)($R_{14}$)—C(O)]$_c$)—$NR_{17}$—Ar—($CH_2$)$_s$ (as defined below) and optionally contains a hydrolyzable moiety;

$R_7$ is a linking group, optionally containing a hydrolyzable moiety or a portion of the hydrolyzable moiety; and $R_8$ is absent or is O, S, $CR_c$, or $NR_c$, where $R_c$ is H or substituted or unsubstituted alkyl, provided that at least one of $R_6$ and $R_7$ contains a hydrolyzable moiety.

In one embodiment, more than one hydrolyzable moiety is present in $R_4$. In one embodiment, a single hydrolyzable moiety is present in $R_4$. In one embodiment, $R_7$ and $R_8$ combined form the hydrolyzable moiety. In one embodiment, $R_7$ contains the hydrolyzable moiety. In one embodiment, $R_6$ contains the hydrolyzable moiety. In one embodiment, a hydrolyzable moiety is present in both $R_6$ and $R_7$. Such hydrolyzable moieties may be cleavable by the same mechanism or through distinct mechanisms.

In one embodiment of the foregoing, $R_6$ is a straight chain substituted or unsubstituted C1-C16 alkyl or a branched substituted or unsubstituted C1-C16 alkyl. In one embodiment of the foregoing, $R_6$ is a straight chain substituted or unsubstituted C1-C5 alkyl or a branched substituted or unsubstituted C1-C5 alkyl. In one embodiment, $R_6$ is —$(CH_2)_p$—, where p is from 1 to 16, from 1 to 10 or from 1 to 5.

In another embodiment, $R_6$ is a polymer. Suitable polymers include any water soluble polymers known in the art or described herein. In one embodiment, the water soluble polymer is a polyethylene glycol (PEG) polymer represented by —$(O-CH_2-CH_2)_b$—, wherein b is an integer from 1 to 30, 1 to 15, from 1 to 10 or from 1 to 5. Specific values for b include, but are not limited to 2, 3, 4 and 5. In another embodiment, the polymer is an amino acid polymer. Suitable amino acid polymers include but are not limited to poly-glycine polymers and poly-alanine polymers from 1 to 10 amino acids in length. Such polymer, including a PEG or amino acid polymer, may contain addition terminal groups resulting from a linkage.

In another embodiment, $R_6$ contains a straight chain substituted or unsubstituted, a branched substituted or unsubstituted alkyl or a polymer (each as described above) linked to an amino acid portion (in the instance when the polymer is an amino acid polymer, two amino acid portions will be joined). The amino acid portion may contain from 1 to 6 amino acids, from 1 to 4 amino acids or from 1-2 amino acids. Suitable amino acids include naturally occurring amino acids, non-naturally occurring amino acids or a combination of the foregoing. In certain specific embodiments, the amino acids may be valine, citrulline, lysine and phenylalanine. In certain embodiment, the amino acid portion is valine and citrulline or lysine and phenylalanine.

In one embodiment, $R_7$ is —$R_a$—O—C(O)—$R_b$—, —$R_a$—O—C(O)—O—$R_b$—, —$R_a$—O—C(O)—NH—$R_b$—, —$R_a$—CH(OH)—$R_b$—, —$R_a$—S—S—$R_b$—, —$R_a$—S—$R_b$—, —$R_a$—O—P(O)(OR$_{11}$)—$R_b$— (where $R_{11}$ is H or a substituted or unsubstituted C1-C5 alkyl), or —$R_a$—C(O)—NH—$R_b$—, where $R_a$ and $R_b$ are each independently absent or substituted or unsubstituted alkyl. In another embodiment, $R_a$ and $R_b$ are each independently absent or a C1-C16 substituted or unsubstituted alkyl. In another embodiment, $R_a$ and $R_b$ are each independently absent or a C1-C5 substituted or unsubstituted alkyl. In another embodiment, $R_a$ and $R_b$ are each absent.

In certain embodiments, $R_7$ is —$R_a$—C(O)—$R_b$—, —$R_a$—O—C(O)—$R_b$—, $R_a$ and $R_b$ are each absent and $R_8$ is O, $R_7$ is —$R_a$—O—C(O)—$R_b$— or —$R_a$—C(O)—$R_b$, $R_a$ and $R_b$ are each absent and $R_8$ is NH, and $R_7$ is —$R_a$—S—S—$R_b$—, —$R_a$—S—$R_b$—, $R_a$ and $R_b$ are each absent and $R_8$ is absent.

In certain specific embodiments, $R_7$ is —$R_a$—O—C(O)—$R_b$—, $R_a$ and $R_b$ are each absent and $R_8$ is absent.

In one embodiment, $R_6$ is represented by U1-(pol)$_b$-U2-([NR$_{16}$—C(R$_{13}$)(R$_{14}$)—C(O)]$_c$)—NR$_{17}$—Ar—(CH$_2$)$_s$, wherein U1 represents an optional linking group;
pol represent a polymer portion;
U2 represents an optional linking group;
$R_{17}$, $R_{16}$ and $R_{13}$ are each independently H or a substituted or unsubstituted C1-C5 alkyl;
$R_{14}$ is a side chain group on a naturally occurring or non-naturally occurring amino acid;
Ar represents an aryl group;
b is an integer from 1 to 15;
c is an integer from 1-10; and
s is an integer from 0 to 4;
Suitable polymers include any water soluble polymers known in the art or described herein. In one embodiment, the water soluble polymer is a polyethylene glycol (PEG) polymer represented by —$(O-CH_2-CH_2)_b$—, wherein s is an integer from 1 to 15, from 1 to 10 or from 1 to 5. Specific values for s include, but are not limited to 2, 3, 4 and 5. In another embodiment, the polymer is an amino acid polymer. Suitable amino acid polymers include but are not limited to poly-glycine polymers and poly-alanine polymers from 1 to 10 amino acids in length.

In certain embodiments, U1 is a substituted or unsubstituted alkyl from 1-10, 1-8, 1-5 or 1-3 carbons in length. In one embodiment, U1 is an unsubstituted alkyl of 1-5 carbons in length. In certain embodiments, U1 is absent.

In certain embodiments, U2 is represented by —$(CH_2)_t$—C(O)—, —C(O)— or —NH—. In certain embodiments, U2 is absent. In the foregoing, t is from 1-10, 1-8, 1-5 or 1-3.

In certain embodiments, $R_{16}$ and $R_{13}$ are each H.

In certain embodiments, $R_{14}$ represents a side chain from valine, citrulline, lysine or phenylalanine. In certain embodiments, c is equal to 2 and $R_{14}$ is a side chain from valine and citrulline or lysine and phenylalanine. In certain embodiment, the hydrolyzable moeity is an amide bond within the group —([NR$_{16}$—C(R$_{13}$)(R$_{14}$)—C(O)]$_c$)—.

The Ar group may contain a single ring or may be polycyclic. In certain embodiments, the Ar group is selected from the group consisting of benzene, pyridine, pyrazine, imidazole, pyrazole, oxazole, thiophene, naphthalene, anthracene, and phenanthrene. In certain embodiment, the Ar group is benzene.

In certain embodiments, s is 1.

In one embodiment, $R_6$ is U1-(pol)$_b$-U2-([NR$_{16}$—C(R$_{13}$)(R$_{14}$)—C(O)]$_c$)—NR$_{17}$—Ar—(CH$_2$)$_s$, $R_7$ is —O—C(O)—, $R_8$ is absent. In one embodiment, $R_6$ is U1-(pol)$_b$-U2-([NR$_{16}$—C(R$_{13}$)(R$_{14}$)—C(O)]$_c$)—NR$_{17}$—Ar—(CH$_2$)$_s$, $R_7$ is —O—C(O)—, $R_8$ is absent, U1 is a substituted or unsubstituted C1-C10 alkyl or absent, U2 is —(CH$_2$)$_t$—C(O)—, —C(O)— or —NH— or absent, pol is a polyethylene glycol polymer, and Ar is a benzene. In one embodiment, $R_6$ is U1-(pol)$_b$-U2-([NR$_{16}$—C(R$_{13}$)(R$_{14}$)—C(O)]$_c$)—NR$_{17}$—Ar—(CH$_2$)$_s$, $R_7$ is —O—C(O)—, $R_8$ is absent, U1 is a substituted or unsubstituted C1-C10 alkyl or absent, U2 is —(CH$_2$)$_t$—C(O)—, —C(O)— or —NH— or absent, pol is a polyethylene glycol polymer, Ar is a benzene, b is 4, c is 2 and s is 1.

In addition, when a purification moiety is present on the conjugate, the $R_3$ and $R_4$ portions lack a hydrolyzable moiety.

In one embodiment the $R_3$ and $R_4$ portions lack a hydrolyzable moiety, $R_4$ is represented by U3-(pol)$_b$-U4, wherein
U3 represents an optional linking group;
pol represent a polymer portion;
U4 represents an optional linking group; and
b is an integer from 1 to 15.

Suitable polymers include any water soluble polymers known in the art or described herein. In one embodiment, the water soluble polymer is a polyethylene glycol (PEG) polymer represented by —$(O-CH_2-CH_2)_b$—, wherein s is an integer from 1 to 15, from 1 to 10 or from 1 to 5. Specific values for s include, but are not limited to 2, 3, 4 and 5. In another embodiment, the polymer is an amino acid polymer. Suitable amino acid polymers include but are not limited to poly-glycine polymers and poly-alanine polymers from 1 to 10 amino acids in length.

In certain embodiments, U3 is a substituted or unsubstituted alkyl from 1-10, 1-8, 1-5 or 1 3 carbons in length. In one embodiment, U3 is an unsubstituted alkyl of 1-5 carbons in length. In certain embodiments, U3 is absent.

In certain embodiments, U4 is represented by —C(O)— or —NH—. In certain embodiments, U4 is absent.

In certain embodiments, $R_8$ is absent.

In certain embodiments, $R_3$ is —(CH$_2$)$_3$— or —C(O)—(CH$_2$)$_3$— and $R_4$ is —CH$_2$—C(O)—O—, —CH$_2$—CH$_2$—C(O)—O— or —CH$_2$(CH$_2$)—C(O)—O—.

In a particular embodiment, $R_3$ is —(CH$_2$)$_3$— or —C(O)—(CH$_2$)$_3$ and $R_4$ is

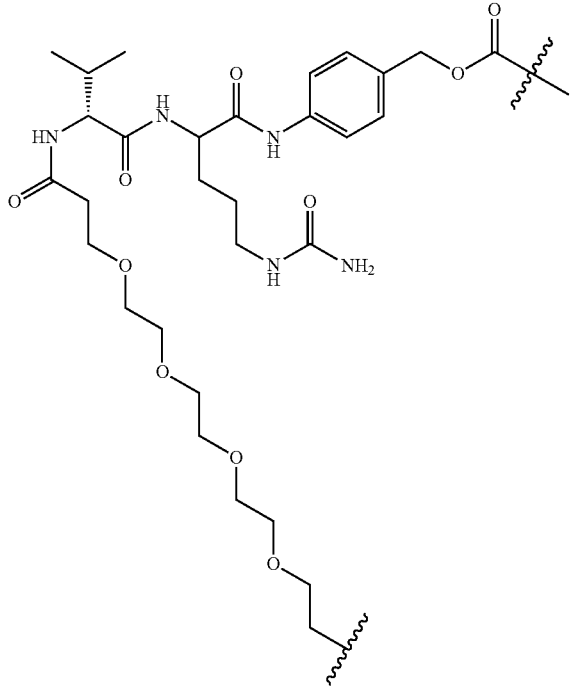 [SMILES: *CCOCCOCCOCCOCCC(=O)N[C@@H](C(=O)NC(CCCNC(N)=O)C(=O)Nc1ccc(COC(*)=O)cc1)C(C)C]

In a particular embodiment, $R_3$ is —(CH$_2$)$_3$— or —C(O)—(CH$_2$)$_3$ and $R_4$ is

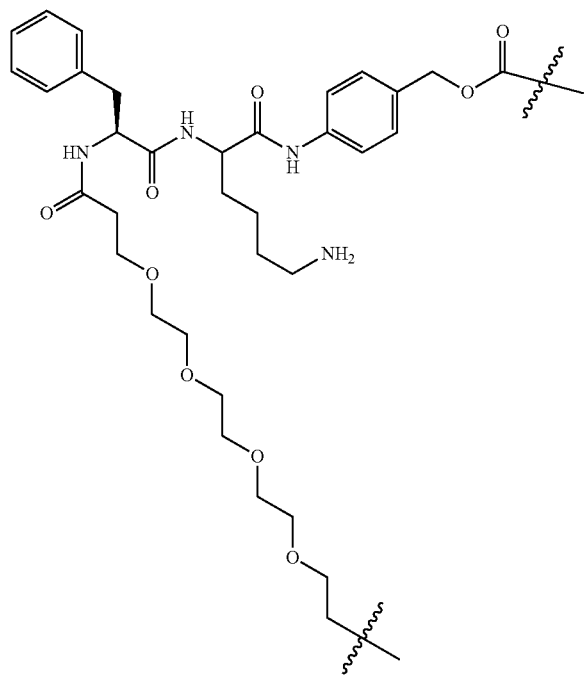 [SMILES: *CCOCCOCCOCCOCCC(=O)N[C@@H](Cc1ccccc1)C(=O)NC(CCCCN)C(=O)Nc1ccc(COC(*)=O)cc1]

In a particular embodiment, $R_3$ is —(CH$_2$)$_3$— or —C(O)—(CH$_2$)$_3$ and $R_4$ is

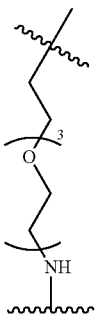

In another embodiment, the releasable, hydrolyzable linkage has the structure $R_9$—Y—$R_{10}$, where Y is a hydrolyzable moiety and $R_9$ and $R_{10}$ are each groups linking Y to the polymer conjugate and the agent, respectively. $R_9$ and $R_{10}$ may be the same of different. In one embodiment, $R_9$ and $R_{10}$ are each independently absent or substituted or unsubstituted alkyl. In another embodiment, $R_9$ and $R_{10}$ are each independently absent or a C1-C16 substituted or unsubstituted alkyl. In one embodiment, $R_9$ and $R_{10}$ are each absent.

In one embodiment of the foregoing, the linking group is —$R_9$—C(O)—O—$R_{10}$—, —$R_9$—O—C(O)—O—$R_{10}$—, —$R_9$—O—C(O)—NR$_{18}$—$R_{10}$— (where $R_{18}$ is a is H or a substituted or unsubstituted C1-C5 alkyl), —$R_9$—CH(OH)—O—$R_{10}$—, $R_9$—CH(OR$_{12}$)—O—$R_{10}$— (where $R_{12}$ is H or a substituted or unsubstituted C1-C5 alkyl), —$R_9$—S—S—$R_{10}$—, —$R_9$—S—$R_{10}$—, —$R_9$—O—P(O)(OR$_{12}$)—O—$R_{10}$— (where $R_{12}$ is H or a substituted or unsubstituted C1-C5 alkyl), —$R_9$—C(O)—NR$_{18}$—$R_{10}$— (where $R_{18}$ is a is H or a substituted or unsubstituted C1-C5 alkyl) or —$R_9$—[NR$_{18}$—C(R$_{13}$)(R$_{14}$)—C(O)]$_c$—$R_{10}$— (where $R_{18}$ is a is H or a substituted or unsubstituted C1-C5 alkyl, $R_{13}$ is H or a C1-C5 alkyl, $R_{14}$ is a side chain group on a naturally occurring or non-naturally occurring amino acid and c is 1-10).

In one embodiment, the rate of cleavage of the hydrolyzable moiety is controlled by the nature of the releasable, hydrolyzable linkage. In each of the foregoing, the hydrolyzable moiety of the releasable, hydrolyzable linkage may be cleaved to release the agent. In one embodiment, the hydrolyzable moiety of the releasable, hydrolyzable linkage is cleaved chemically after administration to the subject under physiological conditions in the subject. In one embodiment, the hydrolyzable moiety of the releasable, hydrolyzable linkage is cleaved by a substance that is naturally present or induced to be present in the subject after administration to the subject under physiological conditions in the subject. In one embodiment, such substance is an enzyme or polypeptide. In one embodiment, the hydrolyzable moiety of the releasable, hydrolyzable linkage is cleaved by a combination of the foregoing.

In one embodiment, the polymer-ADC may be represented by the general structures:
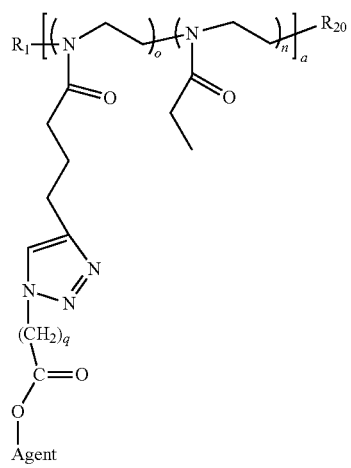
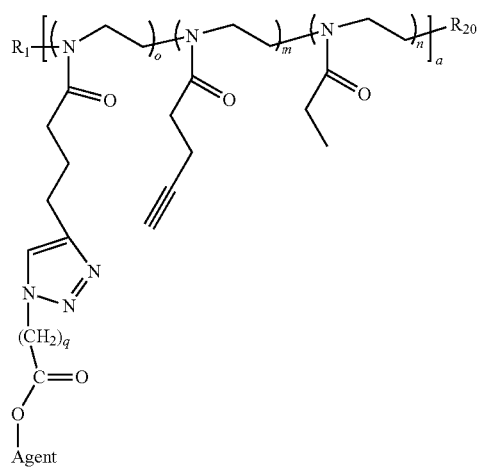
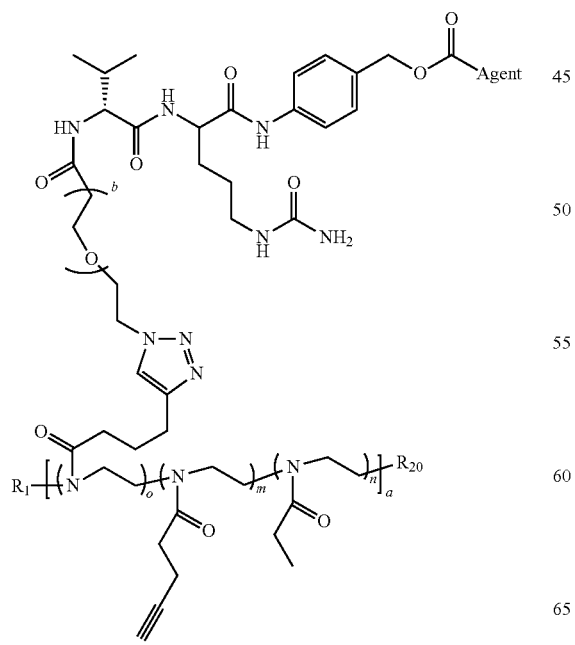
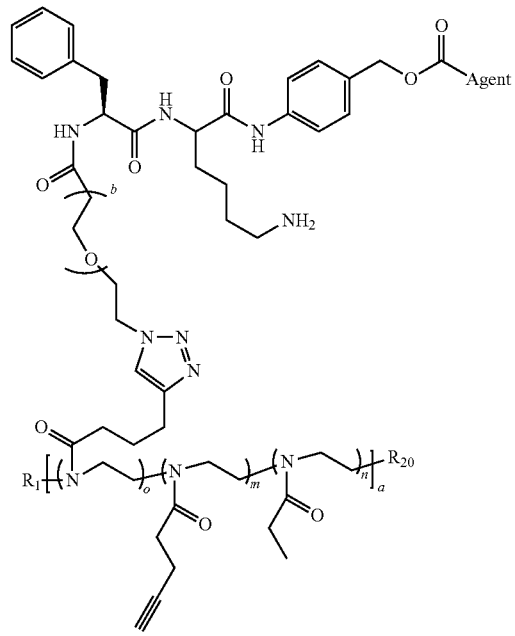
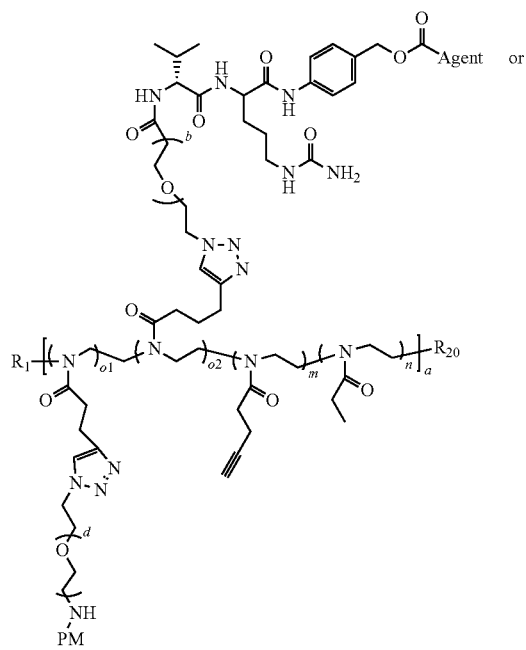

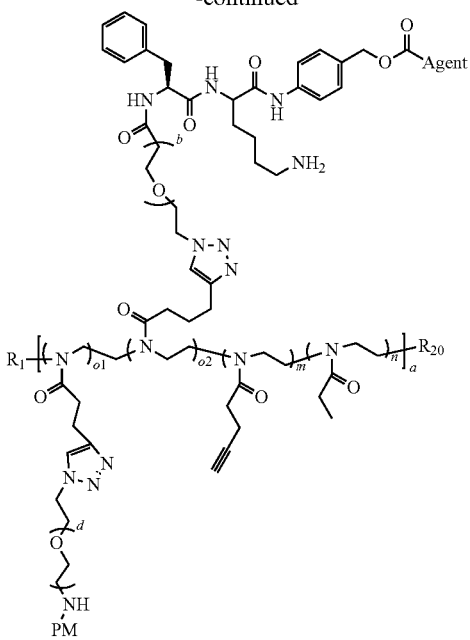

wherein the agent is any agent described herein or known in the art, PM is any purification moiety described herein or known in the art, q is an integer from 1 to 10, b and d are independently an integer from 1 to 30 and the remaining variables are as defined in the current specification.

In one embodiment of the foregoing, o is from 3-15 and the total of m and o is from 1 to 50 and n is from 1 to 1000 or 1 to 500. In certain embodiments, m is 0. In another embodiment, the sum of o1, o2 and m are less than or equal to 50, o1 is an integer from 1 to 5, o2 is an integer from 3 to 45, m is an integer from 1 to 50, and n is from 1 to 1000 or 1 to 500.

In one embodiment, $R_{20}$ is a linking group that serves to link the recognition moiety to the polymer. In one embodiment, $R_{20}$ contains a reactive group that reacts with a binding residue on the recognition moiety. In one embodiment, the reactive group reacts with a stoichiometry binding residue on the recognition moiety specifically and in a 1:1 ratio. In a particular aspect, the recognition moiety is an antibody, such as but not limited to, a single-chain antibody, the stoichiometry binding residue is a selenocysteine moiety as described herein and reactive group is a maleimide group. In a particular aspect, the recognition moiety is an antibody, such as but not limited to, a single-chain antibody, the stoichiometry binding residue is a selenocysteine moiety as described herein and reactive group is an iodoacetimide group. In one aspect, $R_{20}$ incorporates a spacer to provide separation of the recognition moiety and the polyoxazoline polymer. In one aspect, $R_{20}$ may be formed by reacting the polyoxazoline polymer of the present disclosure with a terminating nucleophile and optionally subjecting the structure to further chemical reactions.

In a particular embodiment, $R_{20}$ may be represented by the structure:

$R_{21}$—Z—$R_{22}$, wherein
$R_{21}$ is selected from the group consisting of S, O or N;
Z is a linking group; and
$R_{22}$ is a moiety containing the recognition moiety.
In one embodiment, Z is represented by —$(CH_2)_r$—, wherein r is 1 to 10.

In another embodiment, Z is represented by —$(CH_2)_{r1}$—$R_{23}$-$R_{24}$—$(CH_2)_{r2}$—, wherein $R_{23}$ is absent, —C(O)—, or —N—$R_{25}$—, where $R_{25}$ is H or a substituted or unsubstituted alkyl group, $R_{24}$ is absent, —O—, or —N—$R_{26}$—, where $R_{26}$ is H or a substituted or unsubstituted alkyl group, r1 and r2 are each independently an integer from 0 to 10.

In one aspect of the foregoing, $R_{23}$ is —C(O)—. In one aspect, $R_{24}$ is —O— or —NH—. In one aspect, r1 is an integer from 1 to 4 and r2 is an integer from 0 to 4. In one aspect, $R_{23}$ is —C(O)—, $R_{24}$ is —O—, r1 is 2 and r2 is 0. In one aspect, $R_{23}$ is —C(O)—, $R_{24}$ is —NH—, r1 is 2 and r2 is 2.

In one aspect of the foregoing where Z is represented by —$(CH_2)_{r1}$—$R_{23}$-$R_{24}$—$(CH_2)_{r2}$—, $R_{22}$ is —NH—C(O)—$CH_2$—S-Ab, —NH—C(O)—$CH_2$—Se-Ab,

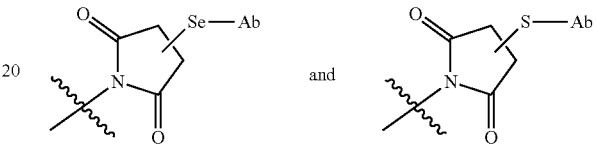

and where Ab represents and antibody

In another embodiment, Z is represented by —$(CH_2)_{r1}$—$R_{23}$-$R_{24}$—$(CH_2)_{r2}$—$R_{27}$-$R_{28}$—$(CH_2)_{r3}$—, wherein $R_{23}$ is absent, C=O, or N—$R_{25}$, where $R_{25}$ is H or a substituted or unsubstituted alkyl group, $R_{24}$ is absent, O, or N—$R_{26}$, where $R_{26}$ is H or a substituted or unsubstituted alkyl group, $R_{27}$ is absent, N—$R_{29}$, where $R_{29}$ is H or a substituted or unsubstituted alkyl group, or —C(O)—, $R_{28}$ is absent, —C(O)— or N—$R_{30}$, where $R_{30}$ is H or a substituted or unsubstituted alkyl group, and r1, r2 and r3 are each independently an integer from 0 to 10.

In one aspect of the foregoing, $R_{23}$ is —C(O)—. In one aspect, $R_{24}$ is —O— or —NH—. In one aspect, r1 is an integer from 1 to 4, r2 is an integer from 0 to 4 and r3 is an integer from 0 to 4. In one aspect, $R_{23}$ is —C(O)—, $R_{24}$ is —NH—, $R_{27}$ is —NH— and $R_{28}$ is —C(O)—, r1 is 2, r2 is 2 and r3 is 1.

In one aspect of the foregoing where Z is represented by —$(CH_2)_{r1}$—$R_{23}$-$R_{24}$—$(CH_2)_{r2}$—$R_{27}$-$R_{28}$—$(CH_2)_{r3}$—, $R_{22}$ is S-Ab or Se-Ab, where Ab represents and antibody.

In one aspect, $R_{22}$ is contains all or a portion of reactive groups used in linking the recognition moiety to the polymer. Representative linking groups include, but are not limited to, an iodoacetamide, bromoacetamide, chloroacetamide, maleimide, or acrylamide group, which is linked to the recognition moiety. In one aspect, $R_{22}$ is a maleimide group or an iodoacetamide group linked to the recognition moiety. In another embodiment, $R_{22}$ lacks such portions of the In a further aspect, the recognition moiety is an antibody, and the binding residue is a cysteine residue. In a further aspect, the recognition moiety is an sc-antibody, and the binding residue is a cysteine residue.

In a further aspect, the recognition moiety is an antibody, and the binding residue is a selenocysteine residue wherein the polyoxazoline polymer and the antibody are bound at the selenocysteine residue in a 1:1 ratio.

In a further aspect, the recognition moiety is a sc-antibody, and the binding residue is a selenocysteine residue wherein the polyoxazoline polymer and the sc-antibody are bound at the selenocysteine residue in a 1:1 ratio.

In such aspect, the $R_{22}$ group may be represented by the following structures. While the structures for representative reactive groups and binding residues are shown, the disclosure of the present application should not be limited to the disclosed examples. When maleimide is a reactive group used to join the antibody to the polymer $R_{22}$ may have the following structure:

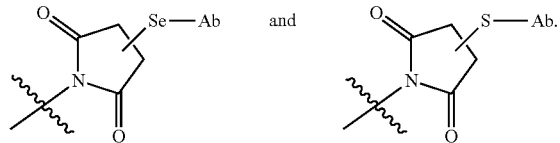

When iodoacetamide is a reactive group used to join the antibody to the polymer $R_{22}$ may have the following structure:

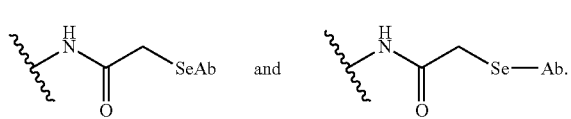

As such, representative $R_{20}$ groups include, but are not limited to (with the understanding that selenium, Se, in the structures below may be replaced with sulfur, S or other binding residues):

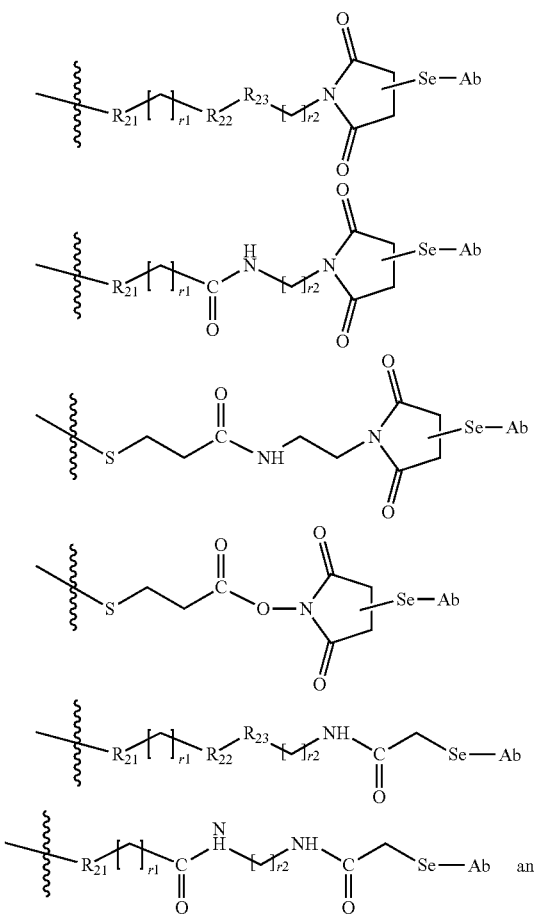

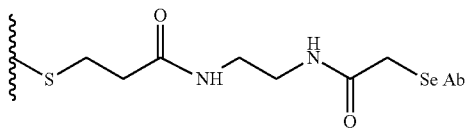

In one embodiment, the present disclosure provides for the following conjugates, wherein the sum of o1, o2 are less than or equal to 50, o1 is an integer from 1 to 5, o2 is an integer from 1 to 45, m is an integer from 1 to 50, a represents a random or block copolymer, Agent represents the agent, BR represents the biding residue on the antibody, Ab represents the antibody, and PM represents the purification moiety:

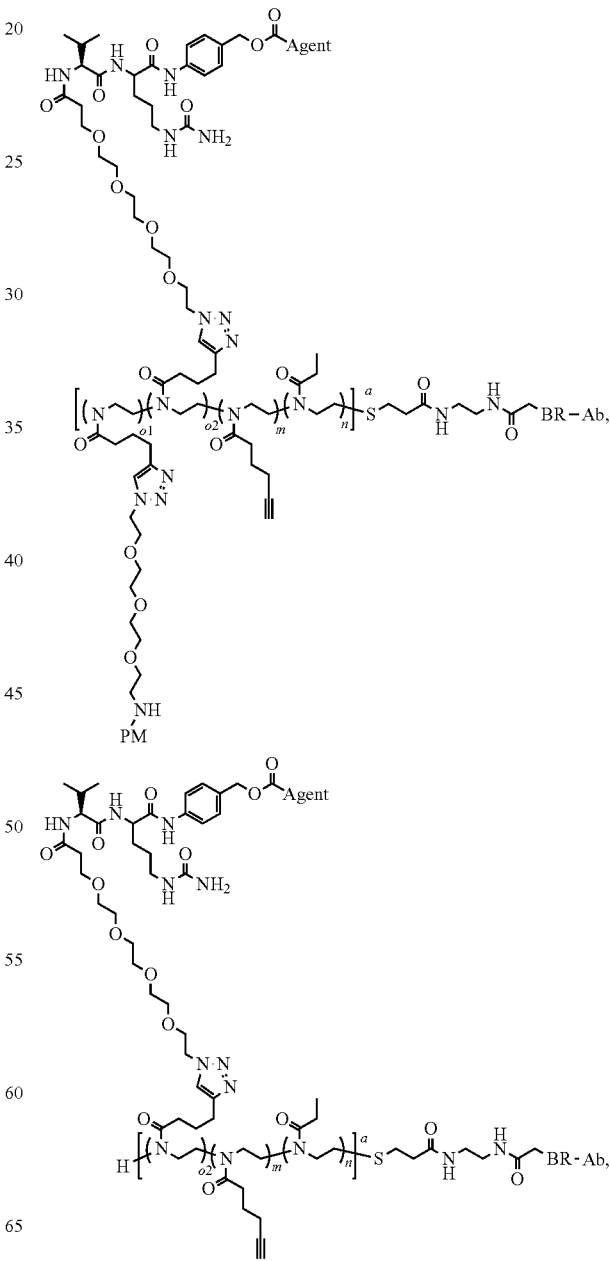

-continued

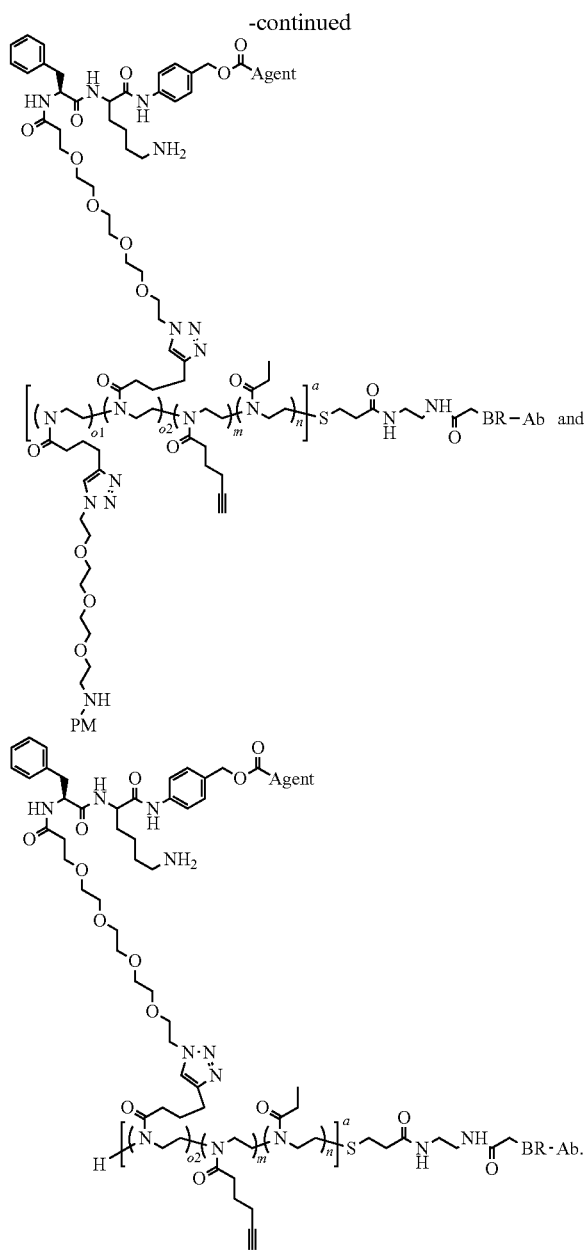

In one embodiment, Ab represents a sc-antibody. In one embodiment, Ab represents a IgG, IgM, IgA, IgE or IgD antibody. The Ab term may represent any of the antibodies described herein or known in the art. In one embodiment, BR represents selenocysteine. In one embodiment, BR represents sulfur. The BR term may represent any binding residue that may be present on the antibodies described. In one embodiment, the agent is colchicine (such as but not limited to deacetylcholchicine) or an auristatin (such as but not limited to monomethyl auristatin E, monomethyl auristatin F or desmethyl-auristatin F). The agent may be any agent described herein or known in the art.

Methods of Synthesis of Polyoxazoline Polymers

In one embodiment, the polymers of the present disclosure are prepared by co-polymerization of appropriate 2-substituted-2-oxazolines containing functional groups. For example, preparation of a water-soluble co-polymer bearing alkyne groups and acetal groups, in addition to a simple 2-alkyl-2-oxazoline can be synthesized using the following oxazoline monomers:

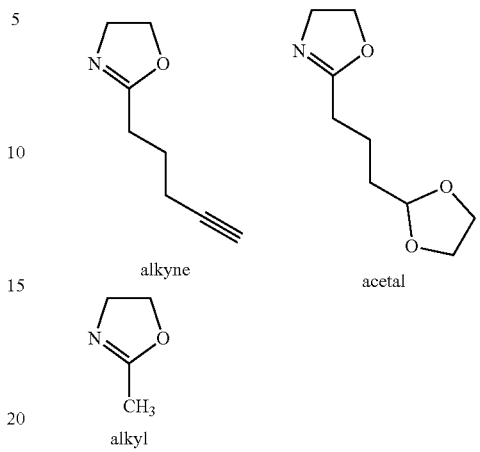

alkyne
acetal
alkyl

The polymerization is initiated by an electrophile such as, but not limited to, methyl triflate, methyl tosylate, p-toluenesulfonic acid, or triflic acid. The co-polymerization can be terminated by a nucleophilic reagent as discussed herein. If terminal functionality is desired, a functionalized terminating agent, such as but not limited to, methyl thiolacetate can be used. For a non-reactive termination terminus, a nucleophile such as an alkyl mercaptan can be used. Similarly a terminating hydroxyl group is also unreactive to many reagents and can therefore be useful in this application. Preferred solvents for the polymerization are chlorobenzene or acetonitrile. The preferred temperature range is from about 40° C. to about 120° C. The time required for the polymerization is dependent on the temperature, the desired molecular weight, and the solvent and can range from about 1 h to about 100 h. In certain embodiments, it is desirable to limit the polymerization reaction to the time required to substantially complete the polymerization reaction. In one embodiment, the progress of the polymerization reaction is monitored using MALDI and/or GPC.

The polymerization can be conducted in several ways. In one embodiment, a mixture of the appropriate oxazoline components can be reacted with the initiator in a preferred solvent with stirring. This reaction yields a random copolymer when the oxazoline components are equally reactive with one another or a block copolymer when one or more of the oxazoline components are less reactive towards one another. In an alternate embodiment, the polymer may also be synthesized in blocks by initiating polymerization with an appropriate initiator in a preferred solvent using only one oxazoline component. The reaction may be monitored with MALDI or GPC to determine when the reaction is substantially complete. When polymerization of the first block is complete, a second oxazoline component is added to reinitiate the polymerization with the incipient living cation at the terminus of the polymer chain; monitoring of the polymerization reaction may be carried out as described. The solvent may be the same as in the first polymerization reaction or different; the reaction temperature and other variables may also be adjusted as desired. Upon completion of the polymerization of the second block, a third oxazoline component is added to reinitiate the polymerization with the living cation at the terminus of the polymer chain; monitoring of the polymerization reaction may be carried out as described. The solvent may be the same as in the first or second polymerization reactions or different; the reaction temperature and other variables may also be adjusted as desired. When the third polymerization step is completed, the polymerization may be terminated by the addition of a terminating agent. The oxazoline components may contain functional groups, or may lack a functional group. The sequential polymerizations can be done in any order. In another embodiment, random copolymerization of two of the oxazoline monomers, followed by continued polymerization of a third block can also be done to produce a polymer having both random and block configurations. In one embodiment, one of the oxazoline monomers lacks a functional group.

Once the desired polymerization process is completed, the polymer is precipitated, such as in ethyl ether, several times and dried under vacuum. The polymer may be further characterized by standard techniques such as but not limited to MALDI, NMR, and GPC.

Work with polyethylene glycol has shown that it is frequently necessary in modification of target molecules to utilize polymers of molecular weights (MWs) of 20,000 Da or higher and molecular weight distributions, or polydispersities (PDs), of less than 1.1. There has been a great deal of work showing that MWs and PDs in the above range cannot be achieved for POZ chains with conventional techniques. As is known in the art PD values will vary with MW; in general, as the molecular weight increases the PD value also increases. It is generally seen that as the molecular weight of growing POZ chains reaches approximately 5,000 Da, the polydispersity increases appreciably. Side reactions, including, but not limited to, chain transfer, begin to grow in importance. The prior art techniques described above when used to generate POZ chains of high MW produce POZ derivatives with unacceptable PD values. The polyoxazoline derivatives of the present disclosure may be produced using polyoxazoline chains that are manufactured using novel methods that result in polyoxazoline derivatives with low PD values and a decreased amount of impurities produced by unwanted side reactions, such as, but not limited to, chain transfer. In one embodiment, the polyoxazoline chains are manufactured to minimize unwanted side reactions, such as, but not limited to, chain transfer, allowing the production of POZ derivatives of increased purity with low PD values. Therefore, the POZ derivatives of the present disclosure may be produced with increased purity and with low PD values suitable for use in pharmaceutical applications. Such methods are described in PCT Application No. PCT/US2008/078159, which is hereby incorporated by reference for such teaching.

In one embodiment, the agent is linked to the polyoxazoline polymer using click chemistry. The click chemistry approach involves the reaction between an alkyne group and an azido group. In one aspect, the click chemistry reaction involves the reaction of an azidoester on the agent and an alkyne on the polyoxazoline polymer. In a particular embodiment of this aspect, the azidoester group is formed by suitable chemical reactions with a chemical group on the agent, such as, but not limited to, a hydroxyl group. An exemplary reaction would be the preparation of an azidoester by displacing a halide from a halo acid with sodium azide to form the azidoacid followed by esterification of the azidoacid with a hydroxyl group on the agent (exemplified here as rotigotine).

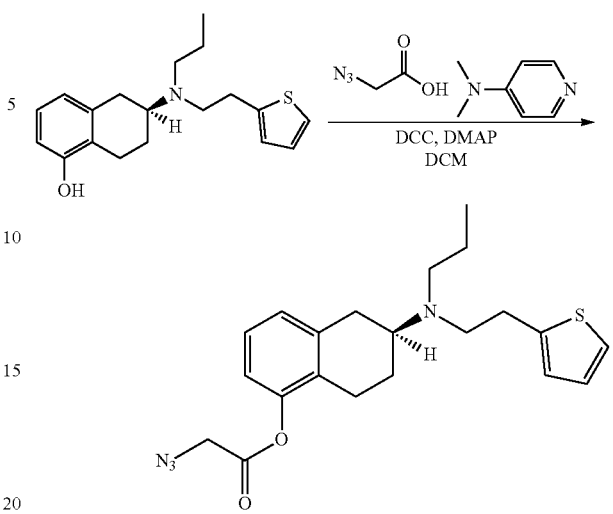

The azido ester is then linked to an alkyne functionality present on the polyoxazoline polymer. In a particular embodiment, the alkyne functionality is an acetylene functionality present at a pendent position on the polyoxazoline polymer.

While the above method may be used, other approaches to the formation of hydrolyzable moieties may be used. For example, a linkage containing an ester hydrolyzable moiety may also be formed by creating an azide functional group on the polyoxazoline polymer, such as a pendent group on the polyoxazoline polymer, creating an alkyne group on the agent, such as an acetylene ester, and reacting the azide group and the alkyne group to form a releasable, hydrolyzable linkage containing a hydrolyzable moiety (in this case an ester bond).

In another approach, a carboxylic acid group can be created on the polyoxazoline polymer, such as a pendent group on the polyoxazoline polymer, and reacting the carboxylic acid group by directly esterifying an alcohol or phenolic group on the agent to form a releasable, hydrolyzable linkage containing a hydrolyzable moiety (in this case an ester bond). In one embodiment, a carboxylic acid group on the polyoxazoline polymer is generated at a pendent position on the polyoxazoline polymer by including a carboxylated monomer in the polymerization reaction.

In the preparation of the polyoxazoline polymer conjugates of the present disclosure, the number of agents on the polyoxazoline polymer is controlled by the number of reactive groups present on the polyoxazoline polymer; in one embodiment, the reactive groups are present in a pendent position on the polyoxazoline polymer. For reactive groups at the pendent position, the number of reactive groups present on the polymer is controlled by the ratio of monomer units (for example, monomer oxazolines) having functionalized side chains (for example, acetylenes) capable of forming linkages with the agent or linking group relative to monomer units having inactive side-chains (for example, alkyls) used in the polymerization. In addition, for a given ratio of monomer units having functionalized side chains, the polymer length can be controlled providing further control of the number of agents loaded onto a given polymer conjugate. Therefore, the number of agents attached to a particular polymer conjugate can be controlled. As described above, the nature of the linking group, the size of the polymer and the route of administration allow control over the release kinetics of the agent from the polymer.

Recognition Moiety

The ADC of the present disclosure comprises a recognition moiety. As used in the present disclosure, the twit "recognition moiety" refers to a molecule that recognizes and binds to a specific epitope/antigen/cell surface marker, including but not limited to, a protein that undergoes internalization into the cellular cytoplasm where it may fuse with endosomes that catalyze the release of the attached agent. Exemplary recognition moieties include, but are not limited to, antibodies, fragments of antibodies, single chain antibodies, polypeptides or peptide mimics, and the like. The recognition moiety, in addition to targeting the ADC to a specific cell, tissue or location, may also have certain therapeutic effect (for example anti-proliferative (i.e., cytostatic and/or cytotoxic) activity against a target cell or pathway). The recognition moiety comprises or may be engineered to comprise at least one chemically reactive group for linking to the polymer portion of the ADC. In one aspect, the reactive group is a selenocysteine moiety.

In a particular embodiment, the recognition moiety is an antibody.

As used in the present specification, the term antibody means any polypeptide chain-containing molecular structure that has a specific shape which binds to and recognizes an antigen/epitope on a target cell, where one or more non-covalent binding interactions stabilize the complex between the polypeptide chain-containing molecular structure and the antigen/epitope. In one embodiment, the antibody molecule is an immunoglobulin. The term antibody therefore includes all types of immunoglobulins (IgG, IgM, IgA, IgE, IgD, etc.), from all sources (e.g., human, rodent, rabbit, cow, sheep, pig, dog, other mammal, etc.). Antibodies may be monoclonal antibodies or polyclonal antibodies; in one aspect, the antibodies are monoclonal antibodies. Methods of raising antibodies and generating monoclonal antibodies are known to those of skill in the art. Antibodies or antigen binding fragments may also be produced by genetic engineering.

In one aspect, the antibodies of the present disclosure are modified to reduce the potential for induction of an immune response in a subject, such as a human subject. Therefore, the term antibodies includes humanized, chimeric, or xenogenic human antibodies, which produce less of an immune response when administered to humans. Alternatively, single chain antibodies (sc-Fv, described below) can be produced containing human variable regions. Therefore, the term antibodies may include single chain antibodies (also referred to herein as sc-antibodies or sc-Fv fragments).

In addition to the entire immunoglobulin structure, immunoglobulin fragments comprising the antigen/epitope binding sites may be used. Therefore, the term antibodies includes immunoglobulin fragments. Such fragments include, but are not limited to, Fab', F(ab')$_2$, or other fragments. Such antibody fragments may be generated from whole immunoglobulins by pepsin, papain, or other protease cleavage. Such fragments may also be designed utilizing recombinant immunoglobulin techniques. For instance sc-antibodies "Fv" immunoglobulins for use in the present invention may be produced by linking a variable light chain region to a variable heavy chain region via a peptide linker (for example, a poly-glycine or another sequence which does not form an alpha helix or beta sheet motif).

The term antibody also includes functional equivalents. The term "functional equivalents" includes antibodies with homologous sequences, chimeric antibodies, artificial antibodies and modified antibodies. One of ordinary skill in the art will understand that there is an overlap in the group of molecules termed "antibody fragments" and the group termed "functional equivalents." Methods of producing functional equivalents are known to the person skilled in the art. Artificial antibodies include scFv fragments, diabodies, triabodies, tetrabodies and molecular recognition unit (mru), each of which has antigen-binding ability. In the single chain antibody, the $V_H$ and VL domains of an antibody are linked by a flexible peptide. Typically, this linker peptide is about 15 amino acid residues long. If the linker is smaller, for example 5 amino acids, diabodies are formed, which are bivalent scFv dimers. If the linker is reduced to less than three amino acid residues, trimeric and tetrameric structures called triabodies and tetrabodies are formed. The smallest binding unit of an antibody is a CDR, typically the CDR2 of the heavy chain which has sufficient specific recognition and binding that it can be used separately. Such a fragment is called a mru.

Several such mrus can be linked together with short linker peptides, therefore forming an artificial binding protein with higher avidity than a single mru.

The functional equivalents also include modified antibodies, including antibodies modified by the covalent attachment of any type of molecule to the antibody. For example, modified antibodies include antibodies that have been modified by glycosylation, acetylation, phosphorylation, amidation, derivatization by known protecting/blocking groups, proteolytic cleavage, linkage to a cellular ligand or other protein. These modifications may be carried out by known techniques, including, but not limited to, specific chemical cleavage, acetylation and formylation.

Functional equivalents may be produced by interchanging different CDRs on different chains within different frameworks. Thus, for example, different classes of antibody are possible for a given set of CDRs by substitution of different heavy chains, whereby, for example, IgG1-4, IgM, IgA1-2, IgD, IgE antibody types and isotypes may be produced. Similarly, artificial antibodies within the scope of the invention may be produced by embedding a given set of CDRs within an entirely synthetic framework. Functional equivalents may be readily produced by mutation, deletion and/or insertion within the variable and/or constant region sequences that flank a particular set of CDRs, using a wide variety of methods known in the art. The CDRs are of primary importance for epitope recognition and antibody binding. However, changes may be made to the residues that comprise the CDRs without interfering with the ability of the antibody to recognize and bind its cognate epitope. For example, changes that do not affect epitope recognition, yet increase the binding affinity of the antibody for the epitope may be made. Thus, also included in the scope of the present invention are improved versions the foregoing, preferably with increased affinity. Several studies have surveyed the effects of introducing one or more amino acid changes at various positions in the sequence of an antibody, based on the knowledge of the primary antibody sequence, on its properties such as binding and level of expression (Yang, W. P. et al., 1995, J. Mol. Biol., 254: 392-403; Rader, C. et al., 1998, Proc. Natl. Acad. Sci. USA, 95: 8910-8915; Vaughan, T. J. et al., 1998, Nature Biotechnology, 16: 535-539). In these studies, equivalents of the primary antibody have been generated by changing the sequences of the heavy and light chain genes in the CDR1, CDR2, CDR3, or framework regions, using methods such as oligonucleotide-mediated site-directed mutagenesis, cassette mutagenesis, error-prone PCR, DNA shuffling, or mutator-strains of E. coli (Vaughan, T. J. et al., 1998, Nature Biotechnology, 16: 535-539; Adey, N. B. et al., 1996, Chapter 16, pp. 277-291, in "Phage Display of Peptides and Proteins", Eds. Kay, B. K. et al., Academic Press). These methods of changing the sequence of the primary antibody have resulted in improved affinities of the antibodies (Gram, H. et al., 1992, Proc. Natl. Acad. Sci. USA, 89: 3576-3580; Boder, E. T. et al., 2000, Proc. Natl. Acad. Sci. USA, 97: 10701-10705; Davies, J. and Riechmann, L, 1996, Immunotechnolgy, 2: 169-179; Thompson, J. et al., 1996, J. Mol. Biol., 256: 77-88; Short, M. K. et al., 2002, J. Biol. Chem., 277: 16365-16370; Furukawa, K. et al., 2001, J. Biol. Chem., 276: 27622-27628).

In one embodiment, such amino acid substitutions are those which: (1) reduce susceptibility to proteolysis, (2) reduce susceptibility to oxidation, (3) alter binding affinity for forming protein complexes, and (4) confer or modify other physico-chemical or functional properties of such antibodies. Such functional equivalents can include various mutations of a sequence from the naturally-occurring peptide sequence. For example, single or multiple amino acid substitutions (preferably conservative amino acid substitutions) may be made in the naturally-occurring sequence (preferably in the portion of the polypeptide outside the domain (s) forming intermolecular contacts). A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al., 1991, Nature, 354: 105, which are each incorporated herein by reference.

Furthermore, any of the foregoing antibodies may be modified to contain one or more non-classical amino acids. In one embodiment, the non-classical amino acid is a selenocysteine residue (for example, as described in Biochemistry. 2009 Dec. 22; 48(50):12047-57, which is incorporated by reference for such teaching). In one embodiment, the non-classical amino acid is placed at the C-terminal end of the antibody so as to minimize interference with the antigen/epitope binding.

In a particular embodiment, the recognition moiety is an antibody. In a further particular embodiment, the recognition moiety is a single-chain antibody. The use of antibodies, particularly monoclonal antibodies and sc-antibodies, in the prevention, diagnosis, and therapy of human diseases is increasing. Over 20 monoclonal antibodies are approved by the Food and Drug Administration and many more are at various stages in clinical development. In addition, ADCs are also being explored to exploit the specificity of the antibody component and the action of a chemical component/agent, for example, a small molecule or an agent-containing polymer. For example, while the antibody molecule provides specificity and affinity, the small molecule affords imaging capability or cytotoxicity.

In one embodiment, the recognition moiety, whether an antibody a single-chain antibody or other form, binds to receptor tyrosine kinase-like orphan receptor (ROR) (reviewed in Front. Oncol., 18 Apr. 2012|doi: 10.3389/fonc.2012.00034). Receptor tyrosine kinases (RTKs) are known to be key regulators of normal cellular processes such as differentiation, migration, proliferation and survival, but they also have a critical role in the development and progression of many types of human cancers. Consequently, RTKs and their ligands have become attractive molecular targets for therapeutic interventions of cancer. These receptors are normally expressed at high levels during development, playing a key role in skeletal and neural organogenesis, but then become repressed in adult tissues. The ROR family of RTKs consists of two evolutionarily conserved proteins, ROR1 and ROR2 and gene expression profiling identified ROR1 and ROR2 as one of the signature genes overexpressed in a variety of cancers. For example, ROR1 has been found to be overexpressed in a variety of hematopoietic cancers including B-cell chronic lymphocytic leukemia, B-cell acute lymphocytic leukemia, and mantle cell leukemia, while ROR2 has been found to be overexpressed in a variety of sarcomas and carcinomas.

ROR2 is a membrane-bound RTK that is activated by non-canonical Wnt signalling through its association with the Wnt5A glycoprotein during the course of normal bone and cartilage development. ROR2 expression is required to mediate the migration of cells during palate development in mammals and mutations in the ROR2 gene have been shown to cause diseases such as brachydactyly type B and autosomal recessive Robinow syndrome. ROR2 has been reported to have pro-tumorigenic effects in certain cell lines. ROR2 has been found to be overexpressed in a variety of sarcomas and carcinomas.

Carcinomas are the most common type of human cancer, arising from cells that have developed the cytological appearance, histological architecture, or molecular characteristics of epithelial cells. Carcinomas are quite heterogeneous entities, reflecting the wide variety, intensity, and potency of various carcinogenic promoters. Subtypes include adenocarcinomas, squamous cell carcinoma, anaplastic carcinoma, large cell and small cell carcinoma, and mixtures thereof. Carcinomas are also classified by the site in which they occur, for example lung cancer, ductal carcinoma of the breast, adenocarcinoma of the prostate, adenocarcinoma or squamous cell carcinoma of the colon and rectum, and the like. Sarcomas are a heterogeneous group of over 60 tumour types that originate from mesenchymal cells and that account for approximately 1% of all human malignancies. Most sarcomas demonstrate a propensity for locally aggressive growth and metastasis.

Selenocysteine Conjugation

A number of conventional methods to conjugate an antibody to a compound are known. For example, the ε-amino group of a lysine (Lys) residue or the thiol group of cysteine (Cys) residue may be used in conjugation reactions with an appropriate functionality on the agent. However, using these approaches, the ADC produced is not a single species of molecule, but rather a mixture of molecules with a range of antibody/agent stoichiometries and points of attachment. Furthermore, the ADCs produced are characterized by substantial batch-to-batch variability. Such a random pattern of conjugation can in many cases impair the antigen/antibody binding reaction. Site specific conjugation of the chemical component/agent to the antibody provides for a defined stoichiometry, decreased batch variability and the potential to preserve the antigen/antibody binding reaction. The goal of site-specific conjugation is to introduce a unique chemical reactivity into the antibody without significantly impacting the structure and/or function of the antibody molecule.

A selenocysteine format has recently been used to provide for site-specific conjugation of a chemical component to an antibody by providing an engineered interface between the antibody and a chemical component. The selenocysteine provides for targeted placement of the chemical component at a desired location and provides for a 1:1 stoichiometry. The process has been described by Hofer and colleagues (PNAS, 105(34), 12451-12456, 2008; Biochemistry, 48(50), 12047-12057, 2009; each of the foregoing are hereby incorporated by reference for such teachings). The selenocysteine interface technology has been used with both whole antibody molecules and antibody fragments without impacting the biological property of the antibody or antibody fragments. As compared to other site-specific antibody conjugation methods, selenocysteine interface method: (a) involves a minor modification of the antibody structure, such as at the C-terminus, which does not interfere with structure or function; (b) utilizes simple and efficient coupling chemistry; and (c) results in 1:1 stoichiometry of the antibody and chemical component.

Agent

The agent may be any agent useful in the treatment of a disease or condition or the diagnosis of a disease or condition. In certain embodiments, the agent is a diagnostic agent or a therapeutic agent. In certain embodiment, the therapeutic agent is an organic small molecule. Furthermore, the agent may be any molecule having a therapeutic or diagnostic application, wherein the agent is capable of forming a linkage with a functional group on a polymer of the present disclosure, such as but not limited to, a POZ polymer, or a linking group linked to a polymer of the present disclosure.

The agent for use with the present disclosure may include any agent known. In one embodiment, the agent is useful for treating cancer. In one embodiment the agent is a cytotoxic agent. In one embodiment, the agent is a microtubule inhibitor, a DNA-damaging agent or a polymerase II inhibitor. Microtubule inhibitors bind tubulin, destabilize microtubules, and cause G2/M phase cell cycle arrest. Auristatins and maytansinoids are two classes of microtubule inhibitors. DNA-damaging agents include anthracyclines, calicheamicins, duocaimycins, and pyrrolobenzodiazepines (PBDs). All of these drugs function by binding the minor groove of DNA and causing DNA stand scission, alkylation, or cross-linking.

Classes of agents useful in the conjugates of the present disclosure include, but are not limited to, auristatin (such as but not limited to monomethyl auristatin E, monomethyl auristatin F, desmethyl-auristatin F), anthracyclines (such as but not limited to daunorubicine, doxorubicin, epirubicin, idarubicin, valrubicin and mitoxantrone), calicheamicins (such as but not limited to calicheamicin and N-acetyl-γ calicheamicin 1,2-dimethyl hydrazine dichloride), maytansinoids (such as but not limited to, DM1, DM4 and ansomitocin), pyrrolobenzodiazepines (such as but not limited to abbeymycin, chicamycin, DC-81, mazethramycin, neothramycins A and B, porothramycin prothracarcin, sibanomicin (DC-102) sibiromycin and tomamycin), dimers of pyrrolobenzodiazepines (such as but not limited to, SJG-136, SG 2285, DRG-16 and ELB-21), colchicines (such as but not limited to colchicine, deacetylcholchicine), dolastatins (such as but not limited to dolstatin 10, 15 and 16), tubulysins (such as but not limited to tubulysin, A, B, D and M), maytansinol, duocarmycins (such as but not limited to duocarmycin A, B1, B2, C1, C2, D, SA and CC-1065 and adozelesin, bizelesin and carzelesin), nemorubicin and other doxorubicin analogues, and, cryptophycins (such as but not limited to, cryptophycinl, 8, 24, 52, 55, 296 and 309) epithilones (such as but not limited to epithilone A, B, C, D, E, F, BMS 247550 and BMS 310705) and safracin (such as but not limited to safracin A and B). Derivatives and analogues of the foregoing are also included within the scope of the present disclosure.

Pharmaceutical Compositions

The polymer conjugates, including polymer-ADCs, of the present disclosure can be formulated for both human and veterinary use and may comprise the polymer-ADC and a pharmaceutically acceptable carrier. In general, a pharmaceutical composition will include a polymer-ADC of the present disclosure in addition to one or more inactive agents such as a sterile, biocompatible carrier including, but not limited to, sterile water, saline, buffered saline, or dextrose solution. The pharmaceutical compositions may be administered either alone or in combination with other therapeutic regimens including other chemotherapeutic compounds, hormones, vaccines, and/or radiation therapy. By "in combination with", it is not intended to imply that the additional regimens must be administered at the same time or formulated for delivery together, although these methods of delivery are within the scope of the invention. In general, each will be administered at a dose and on a time schedule determined for that regimen. Additionally, the invention encompasses the delivery of the polymer-ADC of the present disclosure in combination with agents that may improve bioavailability, reduce or modify metabolism, inhibit excretion, or modify distribution within the body. Alternatively or additionally the polymer-ADC of the present disclosure may be administered together with one or more other compounds that address a symptom or cause of the disease or disorder being treated, or of any other ailment from which the patient suffers. Although the pharmaceutical compositions of the present invention can be used for treatment of any subject (e.g., any animal) in need thereof, they are most preferably used in the treatment of humans.

The pharmaceutical compositions of this invention can be administered to humans and other animals by a variety of routes including oral, intravenous, intramuscular, intraarterial, subcutaneous, intraventricular, transdermal, rectal, intravaginal, intraperitoneal, topical (as by powders, ointments, or drops), buccal, or as an oral or nasal spray or aerosol. In general the most appropriate route of administration will depend upon a variety of factors including the nature of the compound (e.g., its stability in the environment of the gastrointestinal tract), the condition of the patient (e.g., whether the patient is able to tolerate oral administration). At present the intravenous route is most commonly used to deliver the polymer-ADC of the present disclosure. However, the disclosure encompasses the delivery of the polymer-ADC of the present disclosure by any appropriate route taking into consideration likely advances in the sciences of drug delivery.

Methods of Treating

In certain embodiments, the polymer-conjugates of the present disclosure may be targeted to a particular cell or tissue, such as a cancer cell or tumor mass. In one aspect of this embodiment, the polymer-ADC may be used to target a particular cell or tissue expressing an antigen (such as, but not limited to, a cell surface receptor) that is capable of being bound by the antibody attached to the polymer.

In one embodiment, a method of treating a disease state or condition is disclosed. Such method comprises the step of administering to the subject an amount of a polymer conjugate (including a polymer-ADC conjugate) of the present disclosure to a subject which binds to a selected antigen on a target cell and delivers the agent to the cell. In one embodiment, the agent is a cytotoxic agent. In one embodiment, the agent is a microtubule inhibitor, a DNA-damaging agent or a polymerase II inhibitor.

Methods are provided for inhibiting the growth of a cell that expresses an antigen recognized by the antibody on the polymer conjugates of the present disclosure. Such method comprises the step of administering to the subject an amount of a polymer conjugate (including a polymer-ADC conjugate) of the present disclosure to a subject which binds to a selected antigen on a target cell and delivers the agent to the cell. In one embodiment, the agent is a cytotoxic agent. In one embodiment, the agent is a microtubule inhibitor, a DNA-damaging agent or a polymerase II inhibitor. The method for inhibiting the growth of selected cell populations can be practiced in vitro, in vivo, or ex vivo. As used herein, "inhibiting growth" means slowing the growth of a cell, decreasing cell viability, causing the death of a cell, lysing a cell and inducing cell death, whether over a short or long period of time.

As a result, the present disclosure includes the use of anti-the polymer-ADC conjugates described as medicaments.

In the methods described, the polymer conjugate may be administered alone or as a part of a pharmaceutical composition as described herein. In one embodiment, the subject is determined to be in need of such treatment. In a further embodiment, the polymer conjugate is administered in a therapeutically effective amount. In the methods disclosed herein, the subject may be a mammal. In certain embodiments, the subject is a human.

In one embodiment, the disease state is cancer. The polymer-ADCs of the present disclosure are useful in the treatment or prevention of a variety of cancers, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burkitt's lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma. The nature of the cancer to be treated may be determined by the nature of the antibody bound to the polymer conjugate.

Methods are provided for inhibiting the growth of a ROR1 and/or ROR2 positive cell by administering to a patient in need thereof a polymer-ADC of the present disclosure which binds to ROR1 and/or ROR2 and delivers the agent to the ROR1 and/or ROR2 positive cell. In one embodiment, the agent is a cytotoxic agent. The method for inhibiting the growth of selected cell populations can be practiced in vitro, in vivo, or ex vivo. As used herein. "inhibiting growth" means slowing the growth of a cell, decreasing cell viability, causing the death of a cell, lysing a cell and inducing cell death, whether over a short or long period of time. As a result, the present disclosure includes the use of anti-the polymer-ADC conjugates described as medicaments.

For clinical in vivo use, the polymer-conjugate will be supplied as solutions that are tested for sterility and for endotoxin levels. Examples of suitable protocols for administration of the polymer conjugate of the present disclosure are as follows: daily, semi-weekly, weekly for at least one week, at least 2 weeks, at least three weeks, at least 4 weeks or more, by any suitable route. Specific clinical protocols with regard to route of administration, excipients, diluents, dosages, times, etc., can be determined by one of ordinary skill in the art as the clinical situation warrants.

Kits

The present disclosure provides a kit comprising, consisting essentially of or consisting of a polymer conjugate of the present disclosure, packaging material, and instructions for administering the foregoing to a subject for the treatment of a disease or condition such a, but not limited to cancer.

EXAMPLES

Preparation of Materials

To illustrate the teachings of the present disclosure, the preparation of polyoxazoline-ADC conjugates is provided, and the biological activity of these conjugates is described. Abbreviations used are as follows: DC, deacetylcolchicine; MMAE, auristatin; POZ, polyoxazoline terminated with propionic acid; VC, valine-citrine; Phe-Lys, Phenylalanine and Lysine; PAB, p-aminobenzyl alcohol; DCM, dichloromethane; TEA, trimethylamine; DMAP, dimethylaminopyridine; DIPEA, diisopropylethylamine; ACN, acetonitrile; NPC, nitrophenylcarbonate, PEG, polyethylene glycol; $N_3$, azide or azido.

Materials:

Colchicine was purchased from Sigma. Di-tert-butyl dicarbonate, 4-(dimethylamino)pyridine (DMAP), triethylamine (TEA), 0.5 N sodium methoxide in methanol, trifluroacetic acid (TFA), N,N'-Dicyclohexylcarbodiimide (DCC), N-hydroxysuccinimide (NHS), N-Boc-ethylenediamine (Boc-EDA), N,N-diisopropylethylamine (DIPEA), Fmoc Chloride (Fmoc-C1), N-(2-Aminoethyl)Maleimide TFA salt, 1-Hydroxybenzotriazole hydrate (HOBT), Copper (I) iodide and piperidine were purchased from Sigma-Aldrich. $N_3$-PEG4-VC-PAB-PNP, $N_3$-PEG$_4$-VC-PAB-MMAE and $N_3$-PEG4-Phe-Lys(Trt)-PAB-NPC were purchased from Concortis. Diethyl ether, dichloromethane (DCM) and acetonitrile (ACN) were purchased from EMD. Biotin-PEG3-Azide was purchased from Chempep. L(+)-Ascorbic acid sodium salt and cupric sulfate pentahydrate ($CuSO_4.5H_2O$) were purchased from Fluka. Dowex® M4195 was purchased from Supelco. Dimethylformamide (DMF), tetrahydrafuran (THF), dichloromethane (DCM), acetonitrile (ACN), anhydrous sodium sulfate, anhydrous magnesium sulfate, and silica gel 60 (70-230 mesh) were purchased from EMD. Succinimidyl iodoacetate was purchased from CovaChem. Biotin-PEG3-Azide was purchased from Chempep.

Example 1

Preparation of POZ 10p Maleimide 5K

POZ of MW 5,000 with 10 pendent alkyne groups and terminated with a carboxylic acid (POZ 10p acid 5K) was synthesized according to the procedures described in the U.S. Pat. Nos. 8,110,651 and 8,101,706 (each of which are hereby incorporated by reference for such teachings). POZ 10p acid 5K had a $M_n$ of 5,500 g/mol and PDI of 1.01 as determined by matrix-assisted laser desorption/ionization (MALDI) mass spectrometry (MS). End group analysis of polymer by AKTA chromatography (DEAE column) showed that polymer had 99.8% acid end group. The $^1$H NMR spectrum conformed to the structure and indicated that the ratio of 2-pentynyl-2-oxazoline and 2-ethyl-2-oxazoline units in the polymer was 10:40.

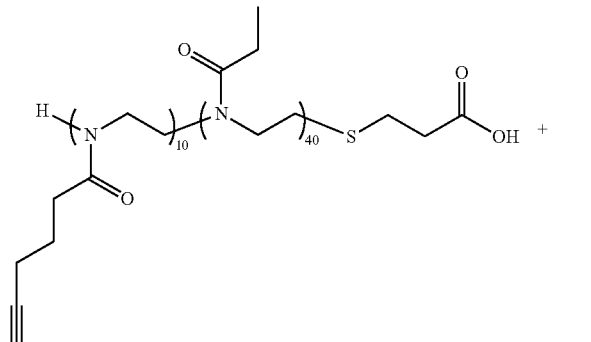

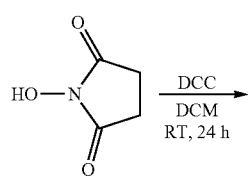

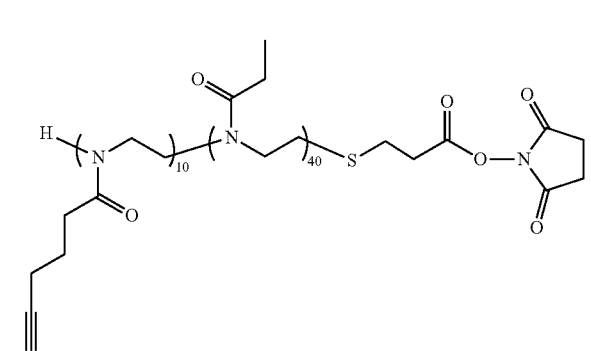

POZ acid activated as the succinimidyl derivative (POZ 10p SPA 5K) was synthesized according to the procedure described in the U.S. Pat. No. 7,943,141. The $^1$H NMR spectrum conformed to the structure and indicated quantitative conversion of acid group to succinimidyl ester.

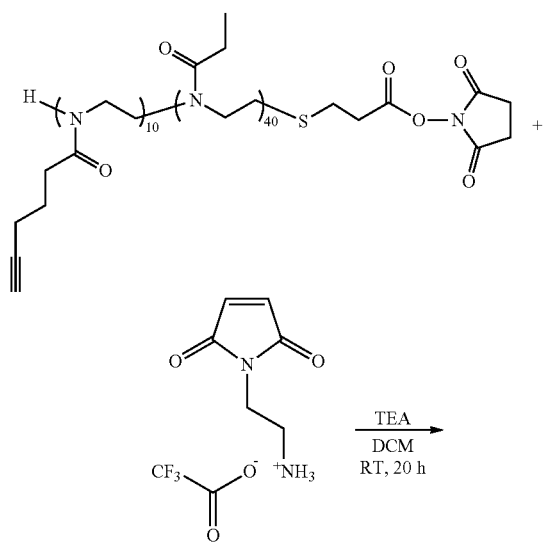

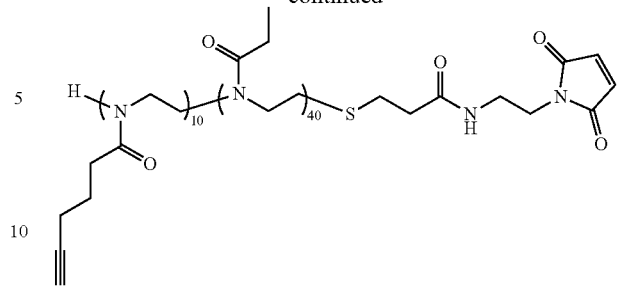

N-(2-Aminoethyl)maleimide trifluoroacetate salt (0.0794 g, $3.125\times10^{-4}$ mol, 1.25 eq.) was dissolved in 15 mL of dichloromethane in a 25 mL round bottom flask. 0.0871 mL of triethylamine (0.0632 g, $6.25\times10^4$ mol, 2.5 eq.) was added into the flask. 1.375 g of POZ 10p SPA 5K ($2.5\times10^{-4}$ mol, 1 eq.) was then added into the flask and the solution was stirred at room temperature under argon for 20 h. At the end of this time, the solution was rotary evaporated to dryness. The residue was dissolved in 100 mL of deionized water, 10 wt. % sodium chloride and extracted into dichloromethane (3×25 mL). The dichloromethane phase was separated and washed with 25 mL of 10 wt. % sodium chloride solution. The dichloromethane phase was separated again, dried over sodium sulfate, filtered, concentrated to 15 mL and precipitated into 225 mL of diethyl ether. The polymer was filtered through a glass sintered frit and dried under high vacuum overnight to give 1.00 g of product (yield: 72%). $^1$H NMR (Varian, 10 mg/mL CDCl$_3$, δ) showed the usual backbone peaks at 1.12 ppm (s, 3H, CH$_3$CH$_2$CO—); 2.31 ppm (small s) and 2.41 ppm (large s) (total area 2H, CH$_3$CH$_2$CO—); and 3.47 ppm (s, 4H, —NHCH$_2$CH$_2$NH—). The pendent group peaks appeared at 1.84 ppm (m, 2H, —CH$_2$CH$_2$CH$_2$CC≡H); and 2.00 ppm (m, 1H, CH$_2$CH$_2$CH$_2$CC≡H). The terminal —CH$_2$SCH$_2$CH$_2$CONH— peaks appeared at 2.70-2.82 ppm. The —CH$_2$ group connected to the nitrogen of the maleimide and the —CH groups of the maleimide appeared at 3.68 ppm and 6.72 ppm, respectively. The ratio of 2-pentynyl-2-oxazoline and 2-ethyl-2-oxazoline units in the polymer was 10.2:40. POZ 10p maleimide 5K had a M$_n$ of 6,400 g/mol and PDI of 1.02 from MALDI.

Preparation of POZ 2p Maleimide 5K

POZ 2p acid 5K was synthesized according to the procedures described in the U.S. Pat. Nos. 8,110,651 and 8,101,706. POZ 2p acid 5K had a M$_n$ of 5,200 g/mol and PDI of 1.02 from MALDI. End group analysis of polymer by AKTA (DEAE column) showed that polymer had 98.6% acid end group. $^1$H NMR indicated that the ratio of 2-pentynyl-2-oxazoline and 2-ethyl-2-oxazoline units in the polymer was 1.9:48.

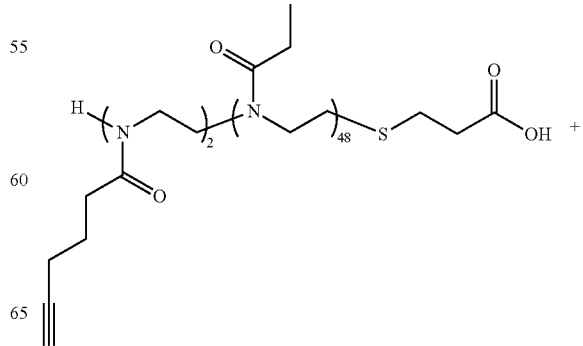

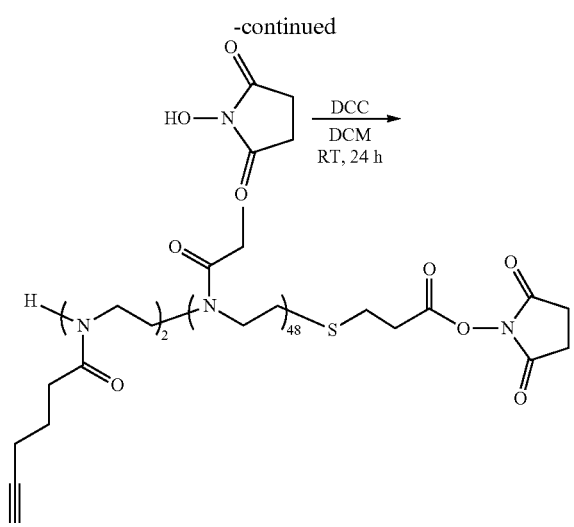

POZ 2p SPA 5K was synthesized according to the procedure described in the U.S. Pat. No. 7,943,141. The $^1$H NMR spectrum conformed to the structure and indicated quantitative conversion of acid group to NHS ester.

added into the flask. The solution was stirred at room temperature under argon for 24 h. The solution was washed with 10 wt % NaCl (0.1N HCl) solution (3×50 mL). Dichloromethane phase was separated, dried over sodium sulfate, filtered, concentrated to 50 mL and precipitated into 750 mL of diethyl ether. The polymer was filtered through a glass sintered frit and dried under high vacuum overnight to give 4.53 g of product (yield: 90%). The $^1$H NMR (Varian, 10 mg/mL CDCl$_3$, δ) showed the usual backbone peaks at 1.13 ppm (s, 3H, CH$_3$CH$_2$CO—); 2.29 ppm (small s) and 2.41 ppm (large s) (total area 2H, CH$_3$CH$_2$CO—); and 3.47 ppm (s, 4H, —NHCH$_2$CH$_2$NH—). The pendent group peaks appeared at 1.84 ppm (m, 2H, —CH$_2$CH$_2$CH$_2$CC≡H); and 2.00 ppm (m, 1H, CH$_2$CH$_2$CH$_2$CC≡H). The terminal —CH$_2$SCH$_2$CH$_2$CONH— peaks appeared at 2.68-2.82 ppm. The —CH$_2$ group connected to the nitrogen of the maleimide and the —CH groups of the maleimide appeared at 3.67 ppm and 6.72 ppm, respectively. The ratio of 2-pentynyl-2-oxazoline and 2-ethyl-2-oxazoline units in the polymer was 1.9:48. POZ 2p maleimide 5K had a M$_n$ of 4,850 g/mol and PDI of 1.02 from MALDI.

Example 2

Coupling of Azido Toxin to POZ with Pendent Pentyne Groups

This reaction is carried out as described in U.S. Pat. No. 8,101,706, which is hereby incorporated by reference for such teaching.

Example 3

Synthesis of Deacetylcolchicine.TFA (3)

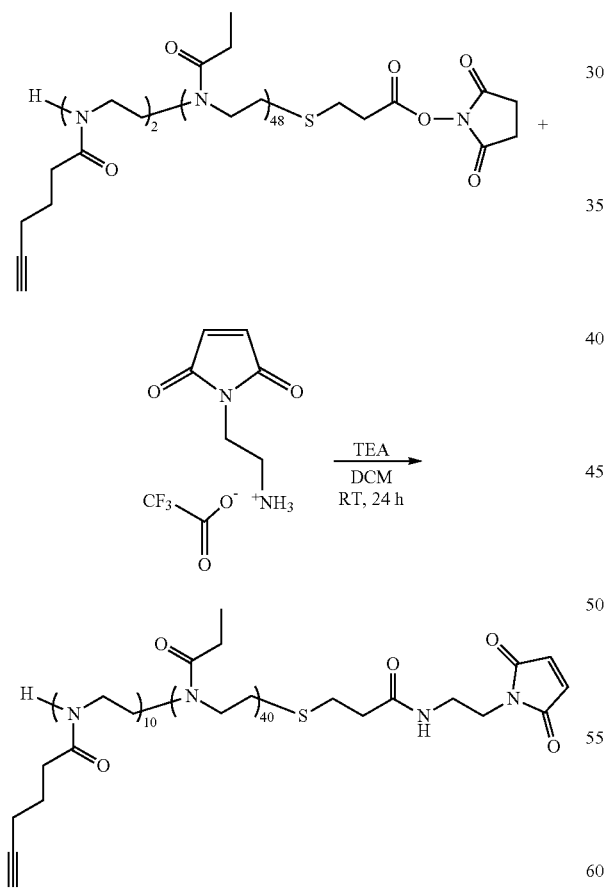

0.31 g of N-(2-Aminoethyl)maleimide trifluoroacetate salt (1.2×10$^{-3}$ mol, 1.25 eq.) was dissolved in 50 mL of dichloromethane in a 100 mL round bottom flask. Triethylamine (0.24 g, 2.4×10$^{-3}$ mol, 2.5 eq.) was added into the flask. POZ 2p SPA 5K (5.0 g, 9.6×10$^{-4}$ mol, 1 eq.) was then

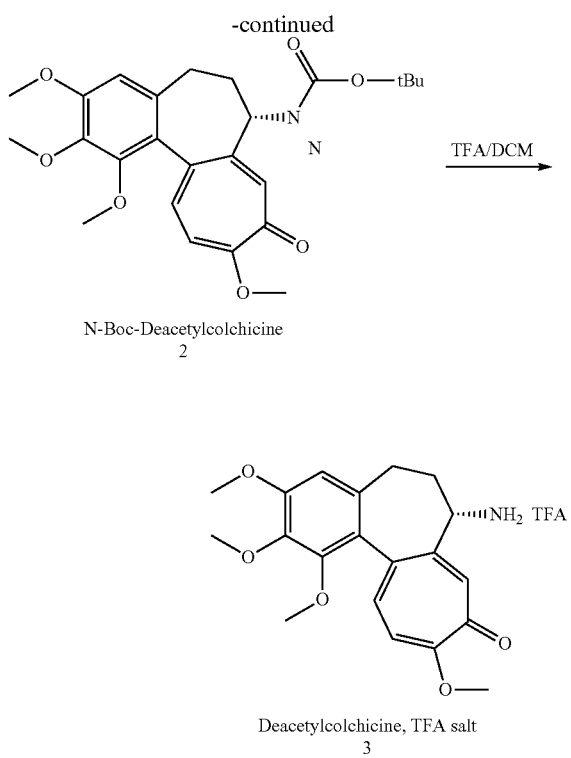

N-Boc-Deacetylcolchicine
2

Deacetylcolchicine, TFA salt
3

Step 1. Synthesis of N-Boc-Colchicine (1)

Deacetylcolchicine (DC) was synthesized according to L. Lebeaii, et al., Syn. Comm., 27(2), 293-296 (1997). A solution of colchicine (2.00 gm, 4.76 mmol) in acetonitrile (ACN) (20 mL) was evaporated to dryness. ACN (20 mL) was then added to the solid. Triethylamine (TEA) (0.74 mL, 5.34 mmol) and dimethylaminopyridine (DMAP) (0.65 gm, 5.33 mmol) were added to the solution, followed by addition of di-tert-butyl dicarbonate (6.23 mL, 27.1 mmol). The solution was allowed to stir under argon atmosphere at 80° C. overnight. After cooling to room temperature, the solution was evaporated on a rotary evaporator to dryness. The crude residual was dissolved in ethyl acetate, and purified by silica gel chromatography on a Biotage Isolera system using ethyl acetate as mobile phase. The product fraction was evaporated on a rotary evaporator to dryness, which afforded 1.47 gm of solid (1. Yield: 59%). Purity>99% by HPLC. $^1$H-NMR of compound 1 in CDCl$_3$: 7.573 ppm, s, 1H; 7.198 ppm, d, 1H; 6.758 ppm, d, 1H; 6.524 ppm, s, 1H; 5.139 ppm, m, 1H; 3.966 ppm, s, 3H; 3.930 ppm, s, 3H; 3.894 ppm, m, 3H; 3.657 ppm, s, 3H; 2.497-2.672 ppm, m, 3H; 2.277 ppm, s, 3H; 1.961 ppm, m, 1H; 1.558 ppm, s, 9H.

Step 2. Synthesis of N-Boc-deacetylcolchicine (2) and Deacetylcolchicine.TFA (3)

N-Boc-Colchicine (1, 1.47 gm, 2.94 mmol) was dissolved in methanol (35 mL), which was allowed to cool to 0° C. under argon atmosphere. To the stirring solution, a 0.5 N sodium methoxide in methanol (23.6 mL, 11.78 mmol) was added dropwise. The solution was allowed to stir at 0° C. Following 65 minutes of reaction, NH$_4$Cl (0.63 gm, 11.78 mmol) was added to neutralize the reaction mixture at 0° C. Following five minutes of stirring, the clear solution was evaporated to dryness on a rotary evaporator. The residual was stirred with DCM (30 mL), and then filtered to remove solid salt. The salt was rinsed with more DCM (10 mL), and filtered into the same filtrate. To this filtrate of crude N-Boc-deacetylcolchicine (2) in DCM was added TFA (4 mL). The solution was allowed to stir at room temperature under argon. Following 2.5 hours of reaction, toluene (35 mL) was added to the reaction mixture, followed by evaporation to dryness (ramp to 0 Torr). The crude residual was dissolved in DCM (10 mL), purified on a silica gel column on Biotage using DCM-Methanol (9:1 v/v) as mobile phase. The elution was monitored at 247 nm. The product containing fraction (R$_f$=0.34 by TLC) was evaporated to near dryness by rotary evaporation, and further dried in vacuum overnight, to give 1.2 gm of yellow colored solid (3, Yield: 87%). Purity>99% by HPLC. $^1$H-NMR of 3 in DMSO-d6: 8.447 ppm, s, 3H; 7.105-7.189 ppm, m, 3H; 6.823 ppm, s, 1H; 3.910 ppm, s, 3H; 3.844 ppm, s, 3H; 3.813 ppm, m, 1H; 3.780 ppm, s, 3H; 2.655 ppm, m, 1H; 2.267 ppm, m, 2H; 1.929 ppm, m, 1H.

Example 4

Synthesis of N—(N$_3$-PEG4-VC-PABC)-Deacetylcolchicine (4)

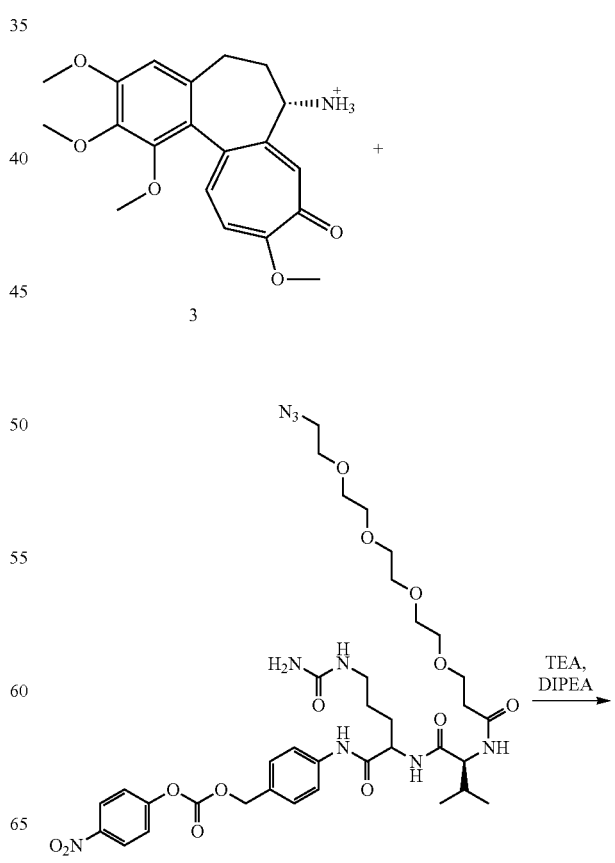

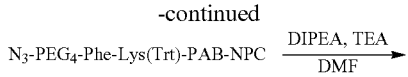

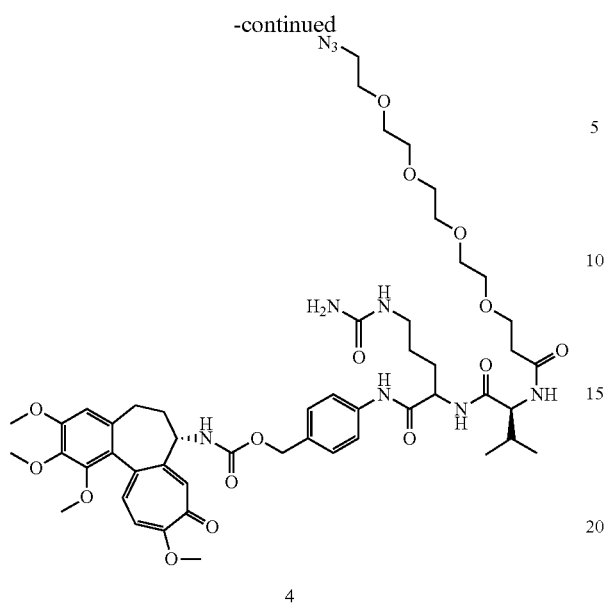

4

Deacetylcolchicine.TFA (3, 0.30 gm, 0.64 mmol) was dissolved in anhydrous DCM (20 mL), and stirred under argon atmosphere. To the yellow colored solution $N_3$-PEG4-VC-PAB-PNP (0.66 gm, 0.76 mmol) was added, followed by addition of TEA (0.27 mL, 1.91 mmol), ACN (5 mL) and DMF (5 mL). DIPEA (0.44 mL, 2.55 mmol) was then added to the reaction mixture. Following 2 days of reaction, reversed phase HPLC analysis of the reaction mixture showed 97% of conversion. The reaction mixture was evaporated to dryness under vacuum at 37° C. The crude residual was dissolved in ethyl acetate-methanol (10 mL, 10:1 v/v), purified by a silica gel column on Biotage using ethyl acetate as mobile phase A and methanol as mobile phase B. Elution was monitored at 247 nm. The product-containing fraction was evaporated to near dryness by rotary evaporation, and further dried in vacuum overnight, to give 0.56 gm of yellow colored solid (4, Yield: 84%). $^1$H-NMR of compound 4 in DMSO-d6: 9.985 ppm, s, 1H; 8.112 ppm, m, 2H; 7.868 ppm, d, 1H; 7.576 ppm, d 2H; 7.234 ppm, d, 3H; 7.115 ppm, d, 1H; 7.032 ppm, d, 1H; 6.768 ppm, s, 1H; 5.977 ppm, t, ill resolved, 1H; 5.411 ppm, s, $NH_2$—; 4.903 ppm, q, 2H; 4.379 ppm, m, 1H; 4.230 ppm, m, 1H; 4.147 ppm, m, 1H; 3.879 ppm, s, 3H; 3.833 ppm, s, 3H; 3.789 ppm, s, 3H; 3.592 ppm, s, 3H; 3.531 ppm, m, —$CH_2CH_2O$—; 3.316 ppm, t, 2H; 3.020 ppm, m, 1H; 2.949 ppm, in, 1H; 2.568 ppm, m, 1H; 2.375 ppm, m, 1H; 2.184 ppm, m, 1H; 1.829 ppm, m, 1H; 1.686 ppm, m, 1H; 1.592 ppm, m, 1H; 1.433 ppm, m, 1H; 1.369 ppm, m, 1H; 0.860 ppm, d, 3H; 0.827 ppm, d, 3H.

Example 5

Synthesis of N—($N_3$-PEG4-Phe-Lys(Trt)-PABC)-Deacetylcochicine 5

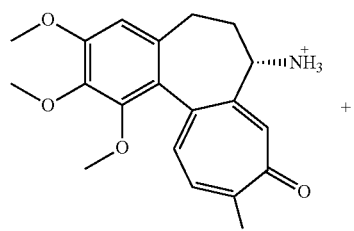

3

$N_3$-PEG4-Phe-Lys(Trt)-PAB-NPC $\xrightarrow{\text{DIPEA, TEA}}{\text{DMF}}$

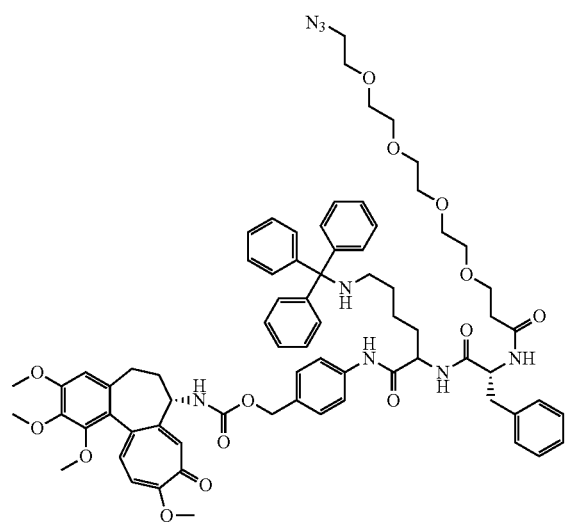

5

Deacetylcolchicine.TFA (3, 0.18 gm, 0.39 mmol, 1.0 eq.) and $N_3$-PEG4-Phe-Lys(Trt)-PAB-NPC (0.50 gm, 0.46 mmol, 1.2 eq.) were dissolved in anhydrous DMF (5 mL). TEA (162 µL, 1.16 mmol, 3.0 eq.) and DIPEA (202 µL, 1.16 mmol, 3.0 eq.) were added to the reaction mixture. The yellowish-colored solution was allowed to stir overnight at room temperature under argon atmosphere. The reaction mixture was evaporated to dryness under vacuum at 37° C. The crude product was dissolved in ethyl acetate, purified by a silica gel column on Biotage using ethyl acetate as mobile phase A and methanol as mobile phase B. Elution was monitored at 317 nm. The product-containing fraction was evaporated to near dryness by rotary evaporation, and further dried in vacuum overnight, to give 0.47 gm of yellow colored solid (5, Yield: 79%). Purity 98% (HPLC). $^1$H NMR of compound 5 (Varian, 10 mg/mL DMSO-d6, δ): 9.992 ppm, s, 1H; 8.112 ppm, m, 2H; 8.020 ppm, d, 1H; 7.566 ppm, d, 2H; 7.381 ppm, d, 6H; 7.226-7.271 ppm, m, 14H; 7.105-7.209 ppm, m, 4H; 7.039 ppm, d, 1H; 6.766 ppm, s, 1H; 4.891 ppm, dd, 2H; 4.557 ppm, t, 1H, ill resolved; 4.080 ppm, m, 1H; 3.870 ppm, s, 3H; 3.828 ppm, s, 3H; 3.784 ppm, s, 3H; 3.527 ppm, m, —$CH_2CH_2O$—; 3.519 ppm, s, 3H; 2.996 ppm, dd, 1H; 2.742 ppm, 7, 1H; 2.575 ppm, m, 1H; 1.2-2.3 ppm, multiple peaks.

Example 6

Synthesis of POZ 10p-EDA-Boc 20K (7)

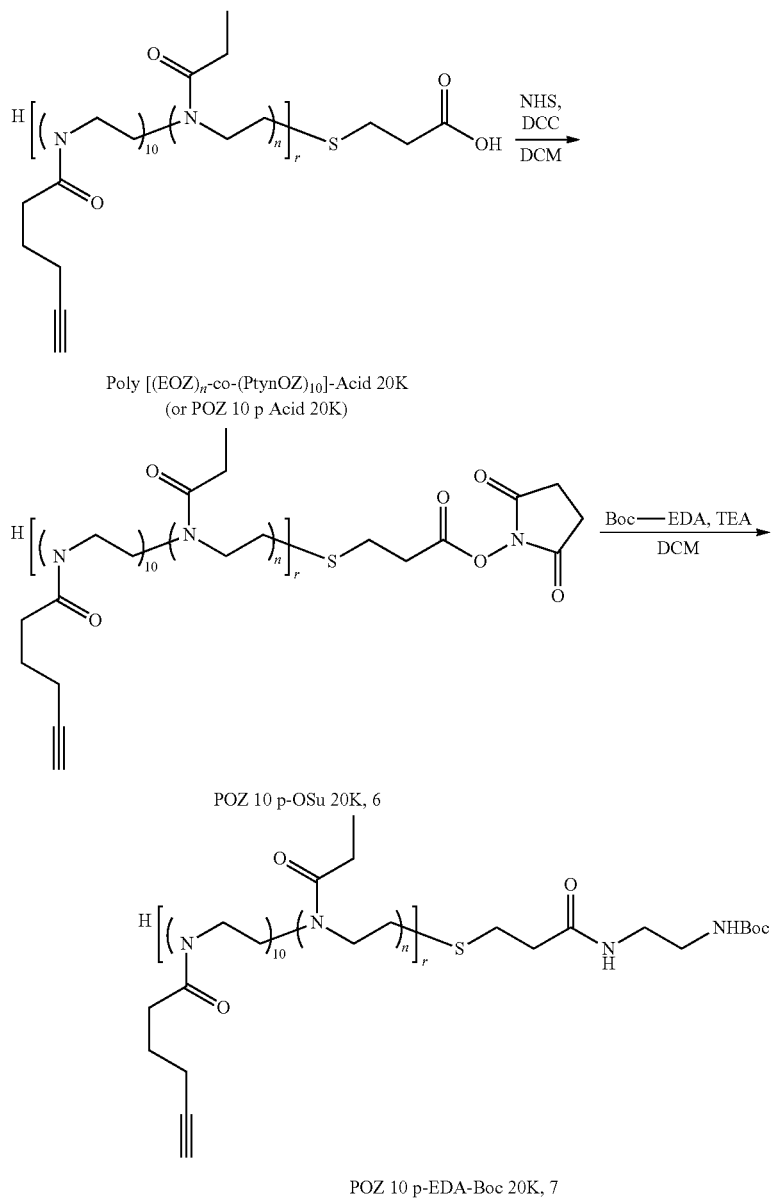

Pendent POZ 10p acid 20K (10 gm, 0.52 mmol, 1.0 eq.) and NHS (0.078 gm, 0.67 mmol, 1.3 eq.) were dissolved in anhydrous ACN (200 mL). The solution was evaporated by rotary evaporation to dryness. The residual was dissolved in anhydrous DCM (100 mL), followed by addition of DCC (0.138 gm, 0.67 mmol, 1.3 eq.). The solution was allowed to stir under argon atmosphere overnight. The reaction mixture was precipitated by slow addition into diethyl ether (1600 mL). The precipitate was filtered, and dried under vacuum overnight, which afforded 8.8 gm of white powder (6). The substitution of succinimidyl group on 6 is 98%, as determined by ion exchange chromatography. $^1$H NMR of compound 6 (Varian, 10 mg/mL CDCl$_3$, δ) showed the usual backbone peaks at 1.12 ppm (s, 3H, CH$_3$CH$_2$CO—); 2.31 ppm (small s) and 2.41 ppm (large s) (total area 2H, CH$_3$CH$_2$CO—); and 3.47 ppm (s, 4H, —NHCH$_2$CH$_2$NH—). The pendent group peaks appeared at 1.84 ppm (m, 2H, —CH$_2$CH$_2$CH$_2$CC≡H); and 2.00 ppm (m, 1H, CH$_2$CH$_2$CH$_2$CC≡H). The terminal succinimidyl group peak appeared at 2.86 ppm (s, 4H).

To a solution of BOC-EDA (0.10 gm, 0.62 mmol, 2.1 eq.) and TEA (0.17 mL, 1.2 mmol, 4.1 eq.) in anhydrous DCM (100 mL) was added compound 6 (5.6 gm, 0.29 mmol, 1 eq.). The solution was stirred at room temperature overnight under argon atmosphere. The reaction mixture was then precipitated by slowly adding into diethyl ether (800 mL).

The precipitate was filtered, and dried overnight in vacuum, which afford 5.0 gm of white powder (7). The substitution of Boc-EDA on 7 is 91%, as determined by ion exchange chromatography. $^1$H NMR of compound 7 (Varian, 10 mg/mL CDC$_3$, δ) showed the usual backbone peaks at 1.12 ppm (s, 3H, CH$_3$CH$_2$CO—); 2.31 ppm (small s) and 2.41 ppm (large s) (total area 2H, CH$_3$CH$_2$CO—); and 3.45 ppm (s, 4H, —NHCH$_2$CH$_2$NH—). The pendent group peaks appeared at 1.84 ppm (m, 2H, —CH$_2$CH$_2$CH$_2$CC≡H); and 1.94 ppm (m, 1H, CH$_2$CH$_2$CH$_2$CC≡H). The terminal —O—C(CH$_3$)$_3$ group peak appeared at 1.43 ppm (s, 9H).

Example 7

Synthesis of POZ 20K Pendent [(Biotin)$_2$(PEG4-VC-PABC-Deacetylcolchicine)$_6$]$_a$-Iodoacetamide (11)

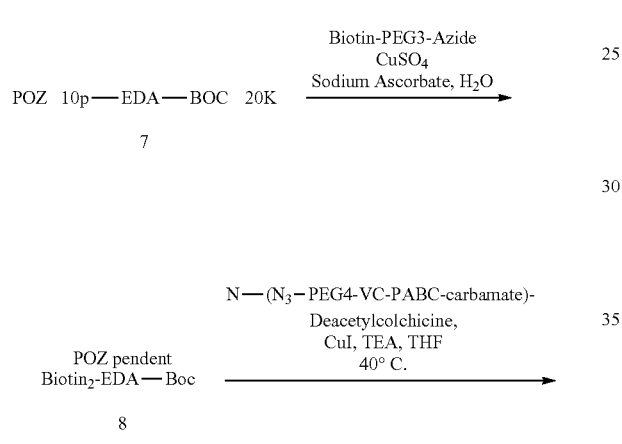

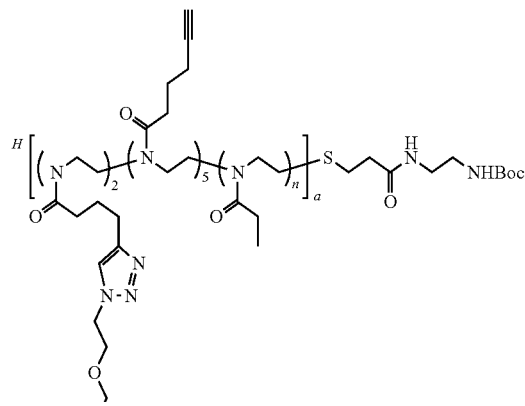

(8)

Structure of POZ 20K Pendent Biotin$_2$-EDA-Boc

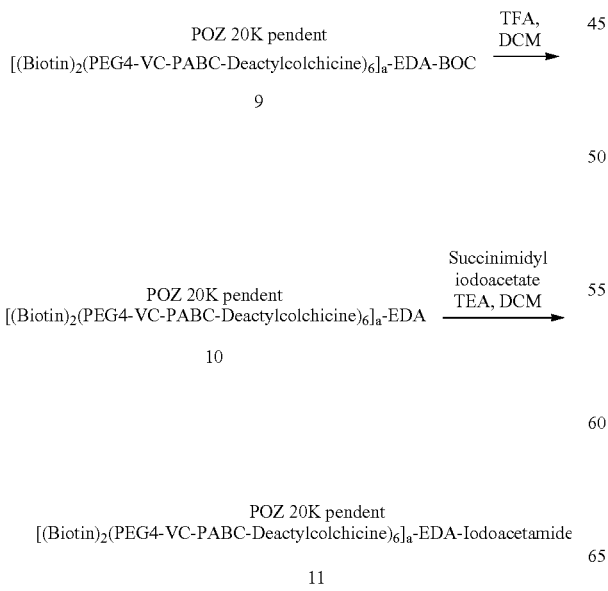

(9)

51
-continued
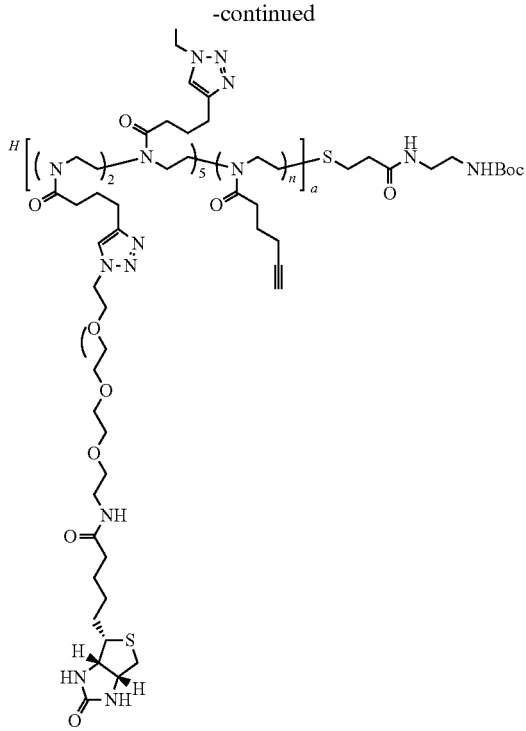
Structure of POZ 20K Pendent
[(Biotin)₂(PEG₄-VC-PABC-Deacetylcolchicine)₆]ₐ-EDA-Boc
52
-continued
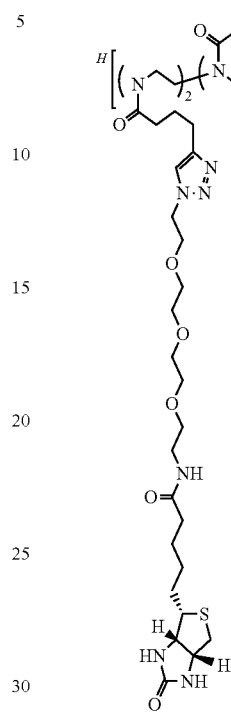
Structure of POZ 20K Pendent
[(Biotin)₂(PEG₄-VC-PABC-Deacetylcolchicine)₆]ₐ-EDA
(10)
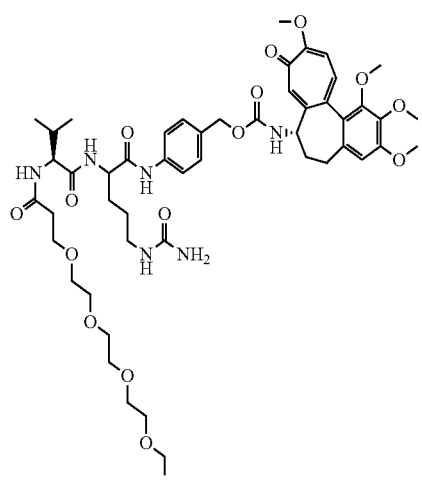
(11)
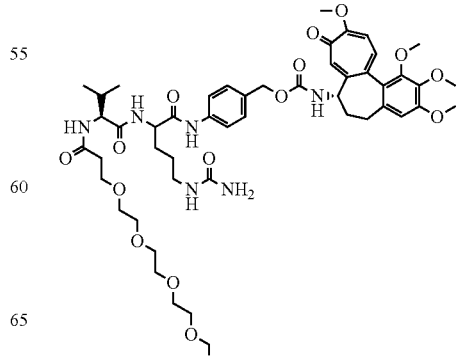

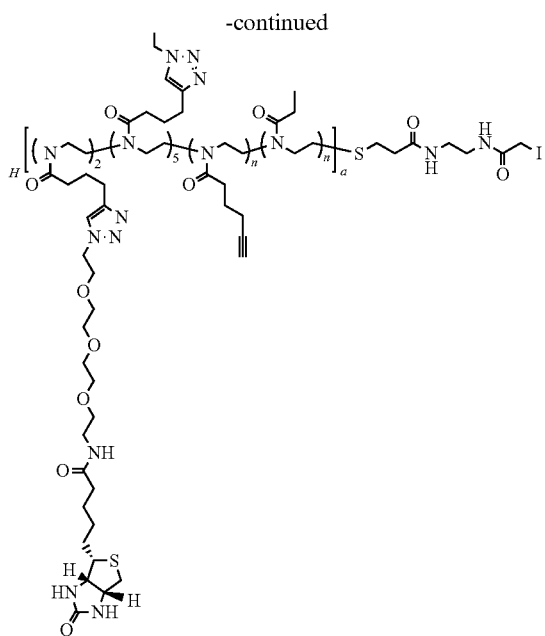

Structure of POZ 20K Pendent
[(Biotin)$_2$(PEG4-VC-PABC-Deacetylcochicine)$_6$]$_a$-Iodoacetamide Azide-PEG3-Biotin (98 mg, 0.22 mmol, 2.1 eq.) and POZ 10p-EDA-BOC 20K (7, 2.000 gm, 0.10 mmol, 1.0 eq.) were dissolved in deionized water (25 mL). The solution was sparged with a slow argon flow for 15 minutes. L(+)-Ascorbic acid sodium salt (44 mg, 0.22 mmol, 2.1 eq.) was then added to the flask, followed by immediate addition of CuSO$_4$.5H$_2$O (55 mg, 0.22 mol, 2.1 eq.). The solution was stirred at room temperature overnight under argon atmosphere. Reversed phase HPLC analysis of the reaction mixture indicated that the reaction went to completion. The solution was passed through a column packed with Dowex® M4195 media (20 gm) to remove copper. The column was eluted with additional deionized water (175 mL). NaCl (30 gm) was dissolved into the eluent (200 mL). The solution was extracted with DCM (3×100 mL). The DCM solution was dried over anhydrous magnesium sulfate (1.5 gm) and sodium sulfate (100 gm). The mixture was filtered through a glass frit. The filtrate was concentrated to near dryness by rotary evaporation, and was further dried in vacuum overnight, which yielded 1.7 gm of white solid (8). $^1$H NMR of compound 8 (Varian, 10 mg/mL DMSO-d6, δ) showed the usual POZ backbone peaks at 0.95 ppm (s) and 0.97 ppm (s) (total area 3H per CH$_3$CH$_2$CO—); 2.28 ppm (large s) and 2.33 ppm (small s) (total area 2H per CH$_3$CH$_2$CO—); and 3.35 ppm (large s) and 3.44 ppm (small s) (total area 4H per —NHCH$_2$CH$_2$NH—). The remaining pendent group peaks appeared at 1.65 ppm (m, 2H per —CH$_2$CH$_2$CH$_2$CC≡H); and 2.75 ppm (m, 1H per CH$_2$CH$_2$CH$_2$CC≡H). The POZ terminal group peaks appeared at 1.37 ppm (s, 9H, —O—C(CH$_3$)$_3$), 6.77 ppm (t, ill resolved, 1H, —NH-Boc); 7.92 ppm (t, ill resolved, 1H, —CONH—). The pendent biotin related peaks include 3.79 ppm (t, ill resolved, 2H per triazole-CH$_2$CH$_2$O—); 4.12 ppm (m, 1H per —CONHCH (CH$_2$S—)— on biotin) and 4.30 ppm (m, 1H per —CONHCH on biotin); 4.45 ppm (t, ill resolved, 2H per triazole-CH$_2$CH$_2$O—); 6.34 ppm (s) and 6.40 ppm (s)(2H per —NH—CO—NH—); 7.81 ppm (m, 1H per triazole ring =CH—N, 1H per —CONH—).

To N—(N$_3$-PEG4-VC-PABC)-Deacetylcolchicine (4, 0.15 gm, 0.15 mmol, 7.5 eq.) in a 50 mL round bottom flask was added anhydrous THF (10 mL). POZ 20K pendent Biotin$_2$-EDA-Boc (8, 0.40 gm, 0.020 mmol, 1 eq.) was then dissolved into the solution. The solution was allowed to stir for 10 minutes under a slow argon flow. CuI (23 mg, 0.12 mmol, 6.0 eq.) was then added, followed by immediate addition of TEA (17 µL, 0.12 mmol, 6.0 eq.). DMF (1 mL) was added into the reaction mixture. The greenish solution was stirred at 40° C. for overnight under argon atmosphere. Reversed phase HPLC analysis of the reaction mixture indicated that the reaction went completion after overnight of stirring. The reaction mixture was filtered, and the filtrate was concentrated to near dryness by rotary evaporation. Residual DMF was further evaporated under vacuum. To the residual 20 mL of methanol was added. The clear green-colored solution was purified by passing through a column packed with Dowex® M4195 media (20 mL) to remove copper. The column was eluted with additional methanol (80 mL). The eluent (100 mL) was concentrated to dryness by rotary evaporation. The residual was dissolved in DCM (10 mL), which was precipitated by slow addition into diethyl ether (150 mL). The precipitate was filtered, and then dried in vacuum overnight, which afforded 0.49 gm of amber colored powder (9). $^1$H NMR of compound 9 (Varian, 10 mg/mL DMSO-d6, δ) showed the usual POZ backbone peaks at 0.95 ppm (s) and 0.97 (s) (total area 3H per CH$_3$CH$_2$CO—); 2.28 ppm (large s) and 2.33 ppm (small s) (total area 2H per CH$_3$CH$_2$CO—); and 3.35 ppm (large s) and 3.44 (small s) (total area 4H per —NHCH$_2$CH$_2$NH—). The POZ terminal group peaks appeared at 1.37 ppm (s, 9H, —O—C(CH$_3$)$_3$), 6.77 ppm (t, ill resolved, 1H, —NH-Boc); 7.82 ppm (t, ill resolved, 1H, —CONH—). The pendent biotin related peaks include 3.79 ppm (t, ill resolved, 2H per triazole-CH$_2$CH$_2$O—); 4.12 ppm (m, 1H per —CONHCH (CH$_2$S—)— on biotin) and 4.30 ppm (m, 1H per —CONHCH on biotin); 4.46 ppm (t, ill resolved, 2H per triazole-CH$_2$CH$_2$O—); 6.34 ppm (s) and 6.40 ppm (s)(2H per —NH—CO—NH—); 7.81 ppm (m, 1H per triazole ring =CH—N, 1H per —CONH—). Some of the pendent PEG4-VC-PABC-deacetylcolchicine peaks (number of H below refer to per pendent PEG4-VC-PABC-deacetylcolchicine) include 0.827 ppm, d, 3H; 0.860 ppm, d, 3H; 1.37 ppm, m, 1H; 1.43 ppm, m, 1H; 1.59 ppm, m, 1H; 1.69 ppm, m, 1H; 1.83 ppm, m, 1H; 2.58 ppm, m, 1H; 2.95 ppm, m, 1H; 3.02 ppm, m, 1H; 3.53 ppm, m, —CH$_2$CH$_2$O—; 3.59 ppm, s, 3H; 3.79 ppm, s, 3H; 3.83 ppm, s, 3H; 3.88 ppm, s, 3H; 4.15 ppm, m, 1H; 4.23 ppm, m, 1H; 4.38 ppm, m, 1H; 4.45 ppm, t, 2H; 4.90 ppm, q, 2H; 5.41 ppm, s, NH$_2$—; 5.98 ppm, t, ill resolved, 1H; 6.77 ppm, s, 1H; 7.03 ppm, d, 1H; 7.12 ppm, d, 1H; 7.23 ppm, d, 3H; 7.58 ppm, d 2H; 7.82 ppm, t, 1H; 7.87 ppm, d, 1H; 8.11 ppm, m, 2H; 9.98 ppm, s, 1H.

POZ 20K Pendent [(Biotin)$_2$(PEG4-VC-PABC-Deacetyl-colchicine)$_6$]$_a$-EDA-BOC (9, 0.480 gm) was dissolved in DCM (3.2 mL) followed by addition of TFA (3.2 mL). The solution was allowed to stir at room temperature under argon for 3 hours. The mixture was then evaporated to dryness by rotary evaporation at 28° C. The residual was dissolved DCM (30 mL). The solution was washed by 15% brine (2×20 mL). Following phase separation, the DCM solution was washed with 15% brine (40 mL, pH was adjusted to 12 by 1N NaOH). Following phase separation, the DCM solution was collected, dried over anhydrous sodium sulfate (20 gm). The mixture was filtered through a glass frit. The filtrate was evaporated to dryness. The residual was dissolved in DCM (7 mL), followed by precipitation in diethyl ether (150 mL). The precipitate was filtered, and dried in vacuum for overnight, which afforded 0.13 gm of white powder (10). $^1$H NMR of compound 10 (Varian, 10 mg/mL DMSO-d6, δ) showed the usual POZ backbone peaks at 0.95 ppm (s) and 0.97 (s) (total area 3H per CH$_3$CH$_2$CO—); 2.28 ppm (large s) and 2.33 ppm (small s) (total area 2H per CH$_3$CH$_2$CO—); and 3.35 ppm (large s) and 3.44 (small s) (total area 4H per —NHCH$_2$CH$_2$NH—). The 1.37 ppm peak of POZ terminal Boc group was greatly reduced, which indicated the removal of terminal Boc group. Terminal amide NH appeared at 7.82 ppm (t, ill resolved, 1H, —CONH—). Some of the pendent biotin related peaks include 3.79 ppm (t, ill resolved, 2H per triazole-CH$_2$CH$_2$O—); 4.12 ppm (m, 1H per —CONHCH(CH$_2$S—)— on biotin) and 4.30 ppm (m, 1H per —CONHCH on biotin); 4.46 ppm (t, ill resolved, 2H per triazole-CH$_2$CH$_2$O—); 6.34 ppm (s)(2H per —NH—CO—NH—) and 6.40 ppm (s); 7.81 ppm (m, 1H per triazole ring =CH—N, 1H per —CONH—). Some of the pendent PEG4-VC-PABC-deacetylcolchicine peaks (number of H below refer to per pendent PEG4-VC-PABC-deacetylcolchicine) include 0.827 ppm, d, 3H; 0.860 ppm, d, 3H; 1.37 ppm, m, 1H; 1.43 ppm, m, 1H; 1.59 ppm, m, 1H; 1.69 ppm, m, 1H; 1.83 ppm, m, 1H; 2.58 ppm, m, 1H; 2.95 ppm, m, 1H; 3.02 ppm, m, 1H; 3.53 ppm, m, —CH$_2$CH$_2$O—; 3.59 ppm, s, 3H; 3.79 ppm, s, 3H; 3.83 ppm, s, 3H; 3.88 ppm, s, 3H; 4.15 ppm, m, 1H; 4.23 ppm, m, 1H; 4.38 ppm, m, 1H; 4.45 ppm, t, 2H; 4.90 ppm, q, 2H; 5.41 ppm, s, NH$_2$—; 5.98 ppm, t, ill resolved, 1H; 6.77 ppm, s, 1H; 7.03 ppm, d, 1H; 7.12 ppm, d, 1H; 7.23 ppm, d, 3H; 7.58 ppm, d 2H; 7.82 ppm, t, 1H; 7.87 ppm, d, 1H; 8.11 ppm, m, 2H; 9.98 ppm, s, 1H.

POZ pendent [(Biotin)$_2$(PEG4-VC-PABC-Deacetylcolchicine)$_6$]$_a$-EDA 20K (10, 0.11 gm, 0.0042 mmol, 1 eq.) was dissolved in ACN (5 mL), which was then evaporated to dryness by rotary evaporation. The residual was dissolved in DCM (5 mL). Succinimidyl iodoacetate (2.5 mg, 0.0083 mmol, 2 eq.) was added, followed by addition of TEA (4.6 µL, 0.033 mmol, 8 eq.). The solution was allowed to stir under argon atmosphere in dark. Following reaction overnight, the solution was precipitated into 80 mL of diethyl ether. The precipitate was filtered, rinsed by diethyl ether (5 mL), and dried in vacuum, which yield 99 mg of white powder (11). Iodoacetamide substitution of 11 was 81%, as determined by ion exchange chromatography after reacting with 3-mercaptopropionic acid.

Example 8

Synthesis of POZ 10p-EDA-Fmoc 20K (13)

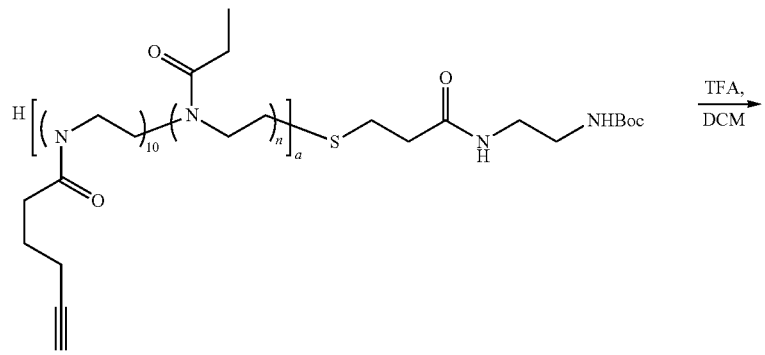

POZ 10 p-EDA-Boc 20K, 7

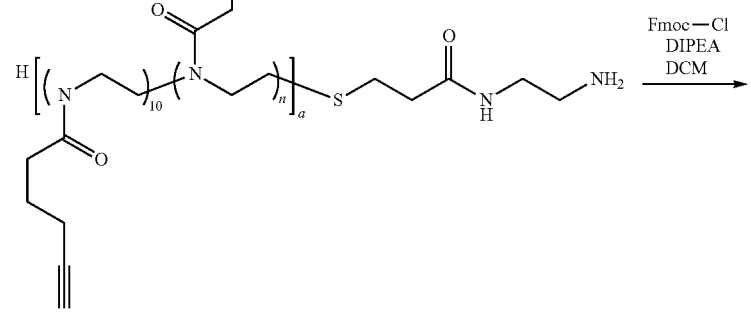

POZ 10 p-EDA 20K, 12

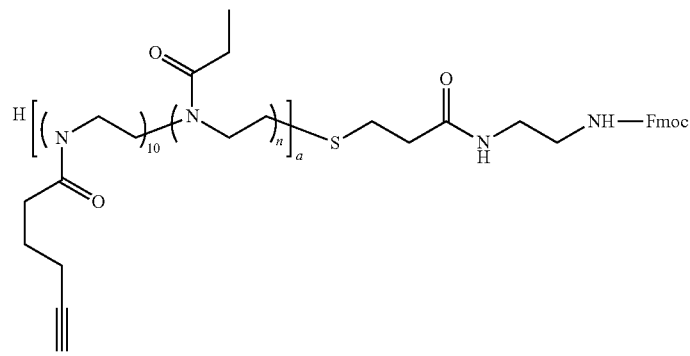

POZ 10 p-EDA 20K, 13

POZ 10p-EDA-BOC 20K (7, 1.0 gm) was dissolved in DCM (6 mL) followed by addition of TFA (6 mL). The solution was stirred at room temperature under argon atmosphere for two hours. The mixture was then evaporated to dryness at 28° C. The residual was dissolved deionized water (10 mL), and the solution pH was adjusted to 11 by 1N NaOH. NaCl was added to the solution to make 15% brine, which was extracted by DCM (4×30 mL). Following phase separation, the DCM phase was collected, dried over anhydrous $MgSO_4$ (1 gm) and $Na_2SO_4$ (90 gm). After filtering off the solids, the filtrate was evaporated to dryness. The residual was dissolved in DCM (10 mL), which was added into diethyl ether (200 mL) to precipitate the polymer. The precipitate was filtered, and dried in vacuum overnight, which afforded 0.86 gm of white powder (12). $^1$H NMR of compound 12 (Varian, 10 mg/mL DMSO-d6, δ) showed the usual POZ backbone peaks at 0.95 ppm (s) and 0.97 (s) (total area 3H per $CH_3CH_2CO$—); 2.28 ppm (large s) and 2.33 ppm (small s) (total area 2H per $CH_3CH_2CO$—); and 3.35 ppm (large s) and 3.44 (small s) (total area 4H per —$NHCH_2CH_2NH$—). The pendent group peaks appeared at 1.64 ppm (m, 2H per —$CH_2CH_2CH_2CC\equiv H$); and 2.77 ppm (m, 1H per $CH_2CH_2CH_2CC\equiv H$). The POZ terminal Boc group (1.37 ppm) disappeared, which indicated that the complete removal of terminal Boc group.

The solution of POZ 10p-EDA 20K (12, 0.42 gm, 0.022 mmol, 1 eq.) in 10 mL of ACN (10 mL) was evaporated to dryness by rotary evaporation. The residual was dissolved in DCM (6 mL). DIPEA (15 μL, 0.087 mmol, 4 eq.) and Fmoc chloride (12 mg, 0.044 mmol, 2 eq.) were added. Following overnight stirring under argon, the solution was evaporated to dryness. The residual was dissolved in deionized water (10 mL), followed by dissolving NaCl (1 gm). The aqueous solution was washed by diethyl ether (15 mL), followed by extraction of the remaining aqueous solution with DCM (3×15 mL). The DCM solution was dried over $Na_2SO_4$ (20 gm), and then filtered to remove solid. The filtrate was concentrated to ~4 mL by rotary evaporation and then precipitated in diethyl ether (80 mL). The precipitate was collected by filtration, and dried in vacuum overnight, which afforded 0.36 gm of white powder (13). NMR in $CDCl_3$ shows conversion to Fmoc. NMR of compound 13 (Varian, 10 mg/mL $CDCl_3$, δ) showed the usual backbone peaks at 1.12 ppm (s, 3H, $CH_3CH_2CO$—); 2.31 ppm (small s) and 2.41 ppm (large s) (total area 2H, $CH_3CH_2CO$—); and 3.45 ppm (s, 4H, —$NHCH_2CH_2NH$—). The pendent group peaks appeared at 1.84 ppm (m, 2H, —$CH_2CH_2CH_2CC\equiv H$); and 2.03 ppm (m, 1H, $CH_2CH_2CH_2CC\equiv H$). Fmoc group peaks appeared at 4.20 ppm (t, 1H); 4.37 ppm (m, 2H); 7.31 ppm (t, 2H); 7.40 ppm (t, 2H); 7.59 ppm (d, 2H); and 7.76 ppm (d, 2H).

Example 9

Synthesis of POZ 20K Pendent [(Biotin)$_2$(PEG4-Phe-Lys-PABC-Deacetylcolchicine)$_5$]$_a$-Iodoacetamide (17)

POZ 10p—EDA—Fmoc 20K

13

$\xrightarrow[\text{50° C.}]{\substack{\text{N—(N}_3\text{—PEG4-Phe-Lys(Trt)-PABC-} \\ \text{Deacetylcolchicine) (5),} \\ \text{Biotin-PEG3-Azide,} \\ \text{CuI, TEA, DMF}}}$ POZ pendent [(Biotin)$_2$(PEG4-Phe-Lys(Trt)-PABC-Deacetylcolchicine)$_5$]$_a$-EDA-Fmoc 20K

14

$\xrightarrow{\text{Piperidine}}$

POZ pendent [(Biotin)$_2$(PEG4-Phe-Lys(Trt)-PABC-Deacetylcolchicine)$_5$]$_a$-EDA 20K

15

$\xrightarrow[\text{TEA}]{\text{Succinimidyl iodoacetate}}$

POZ pendent [(Biotin)$_2$(PEG4-Phe-Lys(Trt)-PABC-Deacetylcolchicine)$_5$]$_a$-Iodoacetamide 20K

16

$\xrightarrow{\text{TFA}}$

POZ pendent [(Biotin)$_2$(PEG4-Phe-Lys-PABC-Deacetylcolchicine)$_5$]$_a$-Iodoacetamide 20K

17

14

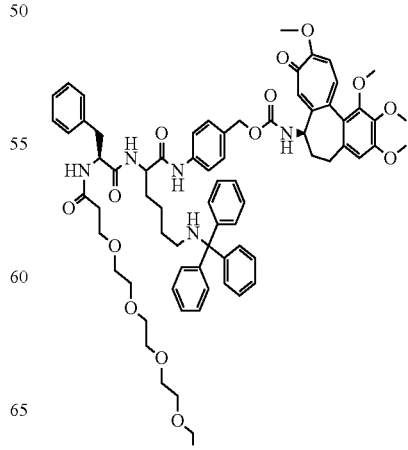

59
-continued
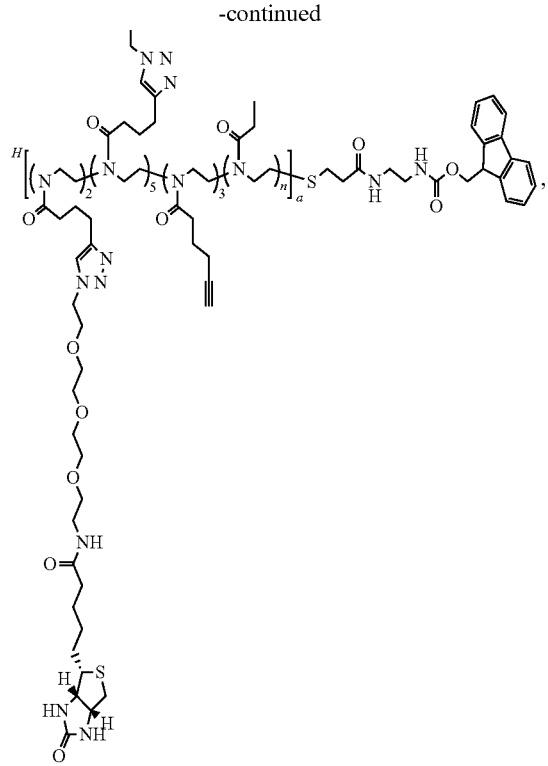
POZ 20K pendent
[(Biotin)₂(PEG4-Phe-Lys(Trt)-PABC-Deacetylcolchicine)₅]ₐ-EDA-Fmoc
60
-continued
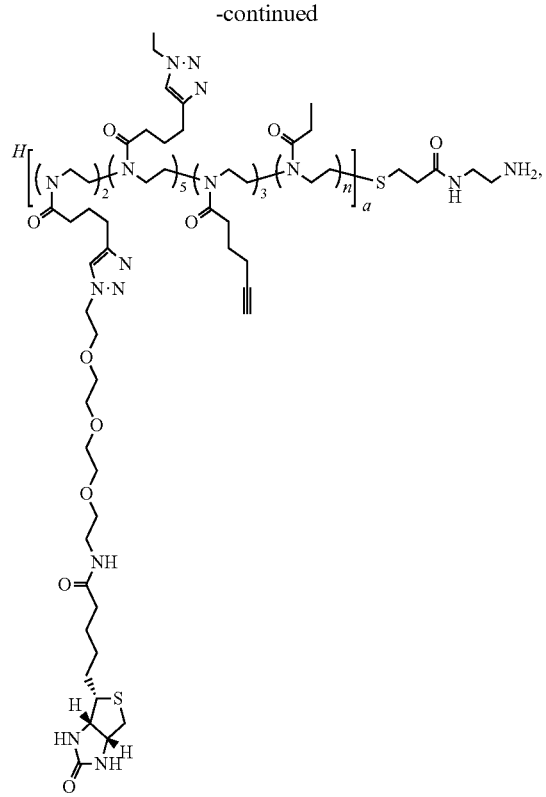
POZ 20K pendent
[(Biotin)₂(PEG4-Phe-Lys(Trt)-PABC-Deacetylcolchicine)₅]ₐ-EDA
15
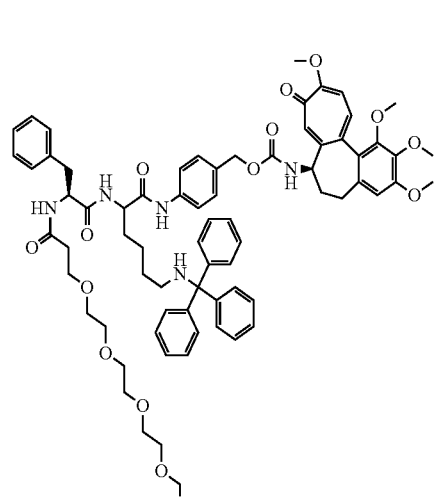
16
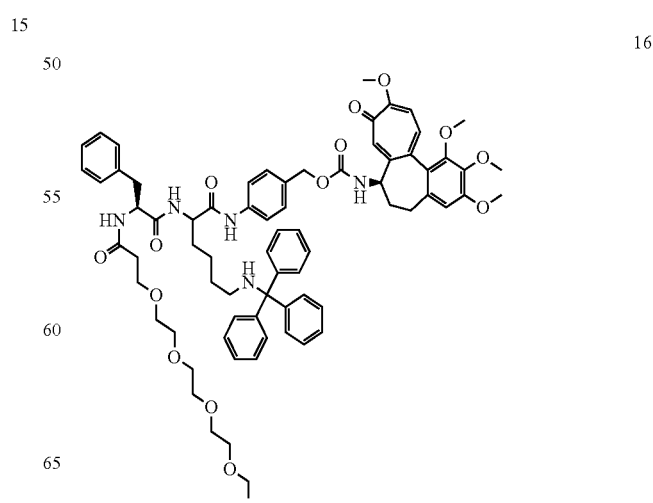

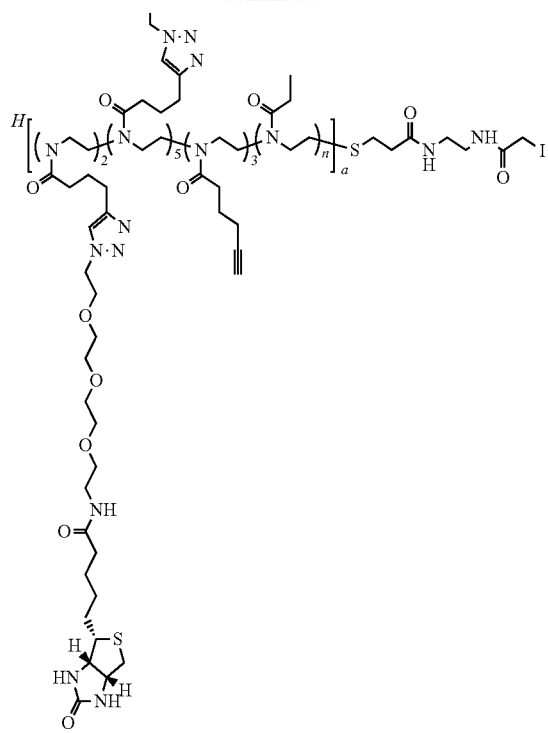

POZ 20K pendent
[(Biotin)₂(PEG4-Phe-Lys(Trt)-PABC-
Deacetylcolchicine)₅]ₐ-Iodoacetamide

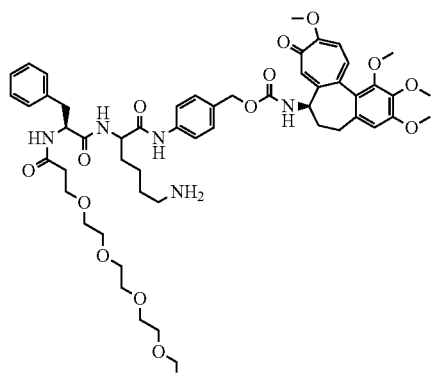

17

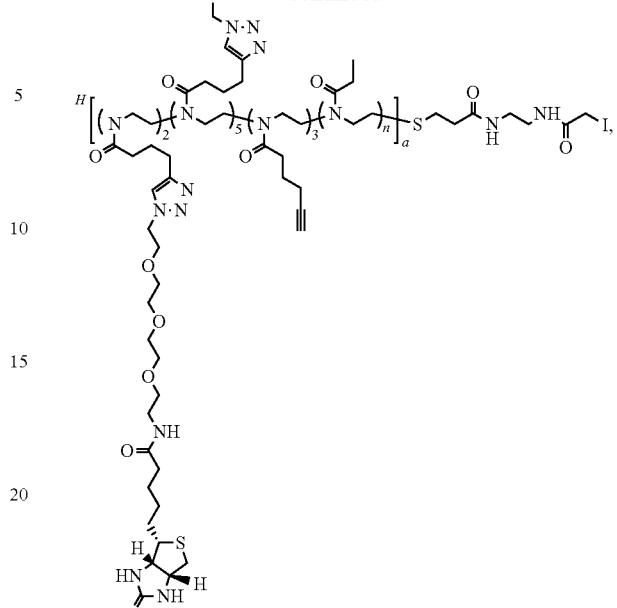

POZ 20K pendent
[(Biotin)₂(PEG4-Phe-Lys-PABC-
Deacetylcolchicine)₅]ₐ-Iodoacetamide To N₃-PEG4-Phe-Lys(Trt)-PABC-Carbonate-Deacetylcolchicine (5, 193 mg, 0.145 mmol, 6 eq.) and POZ 10p-EDA-Fmoc 20K (13, 470 mg, 0.0242 mmol, 1 eq.) in a 100 mL round-bottomed flask was added Biotin-PEG3-Azide (22 mg, 0.048 mmol, 2.0 eq.), which was pre-dissolved in 1 mL of DMF. DMF (1 mL) was used to rinse and transfer the residual Biotin-PEG3-Azide to the reaction mixture. Anhydrous THF (15 mL) was then added. The solution was stirred for 15 minutes under argon. CuI (29 mg, 0.15 mmol, 6.4 eq.) was then added, followed by immediate addition of TEA (22 μL, 0.15 mmol, 6.4 eq.). The greenish solution was stirred at 50° C. for overnight under argon. The reaction mixture was filtered through a 0.2 μm filter, and the filtrate was evaporated to dryness by rotary evaporation. DMF was evaporated under vacuum. Methanol (10 mL) was added to dissolve the residual. The clear, green-colored solution was passed through a column packed with Dowex® M4195 media (9 gm) to remove copper. The column was eluted with additional methanol (90 mL). The eluent was concentrated to dryness. The residual was dissolved in DCM (12 mL). The DCM solution was precipitated by slow addition into diethyl ether (200 mL). The precipitate was filtered, and then dried in vacuum, which afforded 0.64 gm of amber colored powder (14). ¹H NMR of compound 14 (Varian, 10 mg/mL DMSO-d6, δ) showed the usual POZ backbone peaks at 0.95 ppm (s) and 0.97 ppm (s) (total area 3H per CH₃CH₂CO—); 2.27 ppm (large s) and 2.32 ppm (small s) (total area 2H per CH₃CH₂CO—); and 3.35 ppm (large s) and 3.44 (small s) (total area 4H per —NHCH₂CH₂NH—). Fmoc group peaks appeared at 4.12 ppm (m, 1H); 4.30 ppm (m, 2H). Some of the pendent biotin related peaks include 3.79 ppm (t, ill resolved, 2H per triazole-CH₂CH₂O—); 4.12 ppm (m, 1H per —CONHCH(CH₂S—)— on biotin) and 4.30 ppm (m, 1H per —CONHCH on biotin); 4.44 ppm (t, ill resolved, 2H per triazole-CH₂CH₂O—); 6.34 ppm (s)(2H per —NH—CO—NH—) and 6.40 ppm (s); 7.81 ppm (m, 1H per triazole ring =CH—N, 1H per —CONH—). Some of pendent PEG4-Phe-Lys(Trt)-PABC-deacetylcolchicine relevant peaks (number of H below refer to per pendent PEG4-Phe-Lys(Trt)-PABC-deacetylcolchicine) are 3.52 ppm, s, 3H; 3.78 ppm, s, 3H; 3.82 ppm, s, 3H; 3.87 ppm, s, 3H; 4.12 ppm, m, 1H; 4.44 ppm (t, ill resolved, 2H per triazole-CH$_2$CH$_2$O—); 4.53 ppm, t, 1H, ill resolved; 4.91 ppm, s, 2H; 6.76 ppm, s, 1H; 7.02 ppm, d, 1H; 7.11-7.21 ppm, m, 4H; 7.37 ppm (d, from Trt group); 7.56 ppm, d 2H; 7.80 ppm (m, 1H per triazole ring =CH—N); 8.03 ppm, d, 1H; 8.11 ppm, m, 2H; 9.99 ppm, s, 1H.

POZ 20K Pendent [(Biotin)$_2$(PEG4-Phe-Lys(Trt)-PABC-Deacetylcolchicine)$_5$]$_a$-Fmoc (14, 0.44 gm) was dissolved in anhydrous DMF (4 mL) under Ar. Piperidine (0.20 mL) was added to the solution. The solution was allowed to stir under argon atmosphere for one hour. The solution was then evaporated to dryness under vacuum at 40° C. The residual was dissolved in DCM (4 mL) followed by precipitation in diethyl ether (80 mL). The precipitate was washed by diethyl ether (5 mL), and then dried in vacuum, which afforded 0.42 gm of powder. The dried powder was dissolved in DCM (15 mL), and then was washed by 7% brine (30 mL) in a separatory funnel. Following phase separation, the DCM solution was dried over Na$_2$SO$_4$. Following filtration to remove Na$_2$SO$_4$, the filtrate was concentrated to mL, which was precipitated into diethyl ether (150 mL). The precipitate was removed by filtration, rinsed with diethyl ether (10 mL), and then dried in vacuum overnight, which afforded 0.37 gm of powder (15). $^1$H NMR of compound 15 (Varian, 10 mg/mL DMSO-d6, δ) showed the usual POZ backbone peaks at 0.95 ppm (s) and 0.97 (s) (total area 3H per CH$_3$CH$_2$CO—); 2.27 ppm (large s) and 2.32 ppm (small s) (total area 2H per CH$_3$CH$_2$CO—); and 3.35 ppm (large s) and 3.44 (small s) (total area 4H per —NHCH$_2$CH$_2$NH—). Some of pendent biotin relevant peaks include 4.44 ppm (t, ill resolved, 2H per triazole-CH$_2$CH$_2$O—); 6.34 ppm (s) and 6.40 ppm (s)(2H per —NH—CO—NH—); 7.81 ppm (m, 1H per triazole ring =CH—N, 1H per —CONH—). Some of pendent PEG4-Phe-Lys(Trt)-PABC-deacetylcolchicine relevant peaks (number of H below refer to per pendent PEG4-Phe-Lys(Trt)-PABC-deacetylcolchicine) are 3.44 ppm, s, PEG4 —CH$_2$CH$_2$O—; 3.52 ppm, s, 3H; 3.78 ppm, s, 3H; 3.82 ppm, s, 3H; 3.86 ppm, s, 3H; 4.13 ppm, m, 1H; 4.44 ppm (t, ill resolved, 2H per triazole-CH$_2$CH$_2$O—); 4.56 ppm, t, 1H, ill resolved; 4.91 ppm, m, 2H; 6.76 ppm, s, 1H; 7.03 ppm, d, 1H; 7.14-7.26 ppm, m, Ar; 7.37 ppm (d, Trt group); 7.56 ppm, d 2H; 7.80 ppm (m, 1H per triazole ring =CH—N); 8.03 ppm, d, 1H; 8.11 ppm, m, 2H; 9.99 ppm, s, 1H.

POZ 20K Pendent [(Biotin)$_2$(PEG4-Phe-Lys(Trt)-PABC-Deacetylcolchicine)$_5$]$_a$-EDA (15, 0.36 gm, MW 26685 Da, 0.013 mmol, 1 eq.) was dissolved in ACN (5 mL), which was then evaporated to dryness by rotary evaporation. The residual was dissolved in anhydrous DCM (5 mL) and protected under argon atmosphere. Succinimidyl iodoacetate (12 mg, 0.040 mmol, 3.0 eq.) was added, followed by addition of TEA (11 µL, 0.080 mmol, 6 eq.). Following overnight stirring in the dark, the solution was precipitated into diethyl ether (150 mL). The solution was filtered, rinsed by diethyl ether (10 mL), and dried in vacuum to yield 0.36 gm of white powder (16).

POZ 20K Pendent [(Biotin)$_2$(PEG4-Phe-Lys(Trt)-PABC-Deacetylcolchicine)$_5$]$_a$-Iodoacetamide (16, 0.16 gm) was dissolved in DCM (2 mL) followed by addition of TFA (0.10 mL). The solution was allowed to stir at room temperature in dark under argon for overnight. The mixture was then evaporated to dryness by rotary evaporation at 28° C. The solution was dissolved in DCM (4 mL), and then precipitated in diethyl ether (80 mL). The precipitate was filtered, washed with copious amounts of ethyl ether, and dried in vacuum. The dried powder (0.15 gm) was dissolved in deionized water (20 mL). The solution was concentrated to 5 mL by ultrafiltration using an amicon ultrafiltration unit with PLBC membrane (44.5 mm, NMWL 3000). The concentrated solution was diluted to 50 mL by deionized water, which was concentrated again to 5 mL. The concentrated solution was diluted to 30 mL, followed by concentration to 5 mL. The concentrated solution was transferred to a 50 mL vial. The ultrafiltration unit was rinsed by deionized water (10 mL) and transferred to a 50 mL vial. The solution was freeze dried in a lyophilizer to yield 0.15 gm of white powder (17). $^1$H NMR of compound 17 (Varian, 10 mg/mL DMSO-d6, δ) showed the usual POZ backbone peaks at 0.95 ppm (s) and 0.97 ppm (s) (total area 3H per CH$_3$CH$_2$CO—); 2.27 ppm (large s) and 2.32 ppm (small s) (total area 2H per CH$_3$CH$_2$CO—); and 3.35 ppm (large s) and 3.44 (small s) (total area 4H per —NHCH$_2$CH$_2$NH—). POZ terminal iodoacetamide (—COCH$_2$I) peak appeared at 3.62 ppm (s, 2H). Pendent biotin relevant peaks include 4.44 ppm (t, ill resolved, 2H per triazole-CH$_2$CH$_2$O—); 6.34 ppm (s) and 6.40 ppm (s)(2H per —NH—CO—NH—); 7.81 ppm (m, 1H per triazole ring =CH—N, 1H per —CONH—). Some of pendent PEG4-Phe-Lys-PABC-deacetylcolchicine relevant peaks (number of H below refer to per pendent PEG4-Phe-Lys-PABC-deacetylcolchicine) include 3.46 ppm, s, PEG4 —CH$_2$CH$_2$O—; 3.52 ppm, s, 3H; 3.79 ppm, s, 3H; 3.83 ppm, s, 3H; 3.87 ppm, s, 3H; 4.13 ppm, m, 1H; 4.44 ppm (t, ill resolved, 2H per triazole-CH$_2$CH$_2$O—); 4.56 ppm, t, 1H, ill resolved; 4.92 ppm, m, 2H; 6.76 ppm, s, 1H; 7.04 ppm, d, 1H; 7.13 ppm, m, Ar; 7.23 ppm, m, Ar; 7.57 ppm, d 2H; 7.64 ppm, m, Ar; 7.80 ppm (m, 1H per triazole ring =CH—N); 8.05 ppm, d, 1H; 8.11 ppm, m, 1H; 10.0 ppm, s, 1H.

Example 10

POZ 20K Pendent [(PEG4-VC-PABC-MMAE)$_9$]$_a$-Maleimide (19)

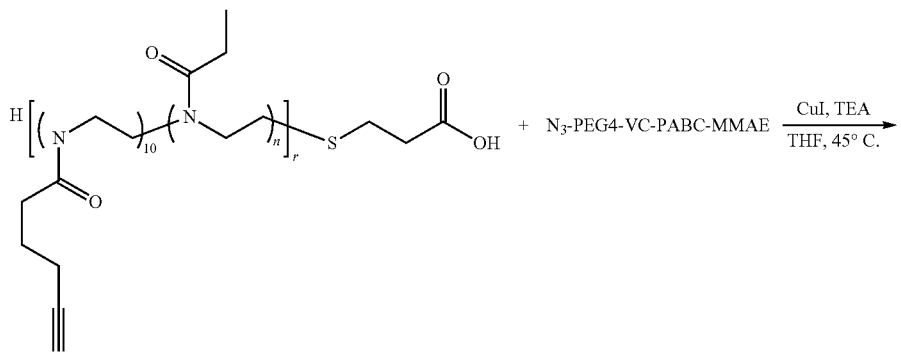

Poly[(EOZ)$_n$-co-(PtynOZ)$_{10}$]-Acid 20K
(or POZ 10 p Acid 20K)

POZ 20K Pendent [(PEG4-VC-PAB-MMAE)9]a-Acid
18

N-(2-Aminoethyl)maleimide•TFA
HOBT, TEA, DCC
DCM
→
-continued

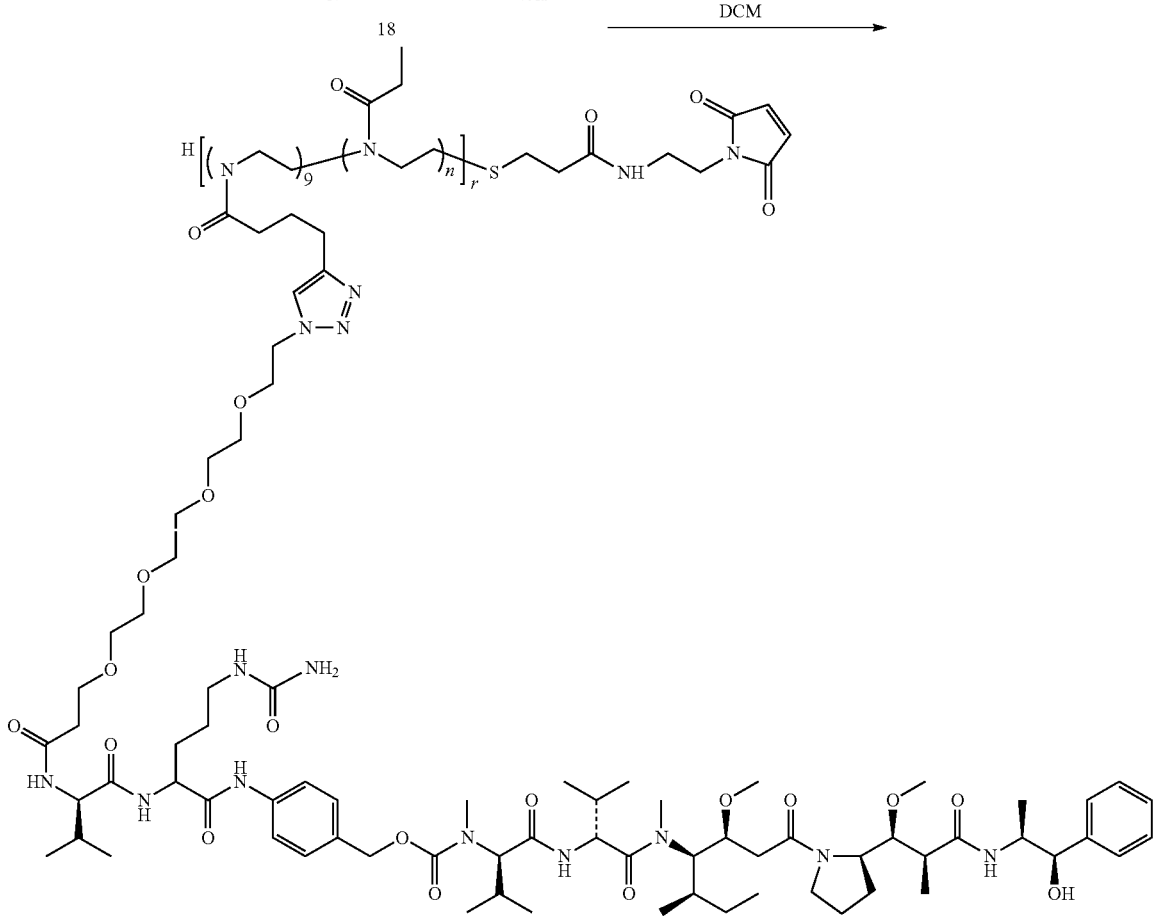

POZ 20K Pendent [(PEG4-VC-PAB-MMAE)9]a-Maleimide, 19

To N3-PEG4-VC-PABC-MMAE (72 mg, 0.049 mmol, 9 eq.) in a glass vial was added THF (4 mL). Poly [(EOZ)$_n$-co-(PtynOZ)$_{10}$]-Acid 20K (106 mg, 0.00544 mmol, 1 eq.) was then added into the solution. The solution was stirred under argon for 10 min. CuI (9 mg, 0.05 mmol, 9 eq.) was then added to the mixture, followed by immediate addition of TEA (7 µL, 0.05 mmol, 9 eq.). The solution was stirred at 45° C. overnight under argon. The greenish mixture was analyzed by reversed phase HPLC, which indicates that the reaction was completed as no residual N3-PEG4-VC-PABC-MMAE remained in the reaction mixture. The solution was evaporated to dryness by rotary evaporation. 2 mM HCl (4 mL) and ACN (4 mL) were added to dissolve the residue, which was purified through a column packed with Dowex M4195 media (2 mL) to remove copper. The column was eluted by 1:1 v/v of 2 mM HCl and ACN (10 mL). ACN was evaporated by rotary evaporation. NaCl was added to the remaining aqueous solution to make 15% brine. The solution was extracted with DCM (3×30 mL). Following phase separation, DCM solution was concentrated to ~20 mL and dried over anhydrous sodium sulfate (10 gm). The mixture was filtered through a glass frit, and the filtrate was concentrated to ~4 mL. The solution was then precipitated into diethyl ether (80 mL). The precipitate was collected by filtration and dried in vacuum to yield 108 mg of white powder 18. $^1$H NMR of compound 18 (Varian, 10 mg/mL DMSO-d6, δ) showed the usual POZ backbone peaks at 0.95 ppm (s) and 0.97 (s) (total area 3H per CH$_3$CH$_2$CO—); 2.27 ppm (large s) and 2.32 ppm (small s) (total area 2H per CH$_3$CH$_2$CO—); and 3.35 ppm (large s) and 3.47 (small s) (total area 4H per —NHCH$_2$CH$_2$NH—). Some of pendent PEG4-VC-PABC-MMAE relevant peaks (number of H below refer to per pendent PEG4-VC-PABC-MMAE) include 0.70-0.95 ppm, m, 24H, —CH$_3$; 3.50 ppm, s, —(CH$_2$CH$_2$O)$_3$—; 3.79 ppm, t, ill resolved, 2H per triazole-CH$_2$CH$_2$O—); 3.99 ppm, m, 2H; 4.23 ppm, m, 2H; 4.45 ppm (main peak, t, ill resolved, 2H per triazole-CH$_2$CH$_2$O—); 5.04 ppm, m, 2H; 5.41 ppm, s, 2H; 6.04 ppm, s, 1H; 7.17 ppm, m, 1H, Ar on MMAE; 7.27 ppm, d, 2H, Ar of PAB; 7.31 ppm, m, 4H, Ar on MMAE; 7.59 ppm, d, 2H, Ar of PAB; 7.82 ppm (m, 1H per triazole ring =CH—N); 8.13 ppm, d, 1H; 10.03 ppm, s, 1H.

POZ 20K pendent-(PEG4-VC-PABC-MMAE)$_9$-Acid (18, 93 mg, 0.0029 mmol, 1.0 eq.) was dissolved in anhydrous ACN (2 mL), followed by addition of HOBT (0.4 mg, 0.002 mmol, 0.8 eq.) and N-(2-aminoethyl)maleimide TFA salt (1 mg, 0.004 mmol, 1.3 eq.). The solution was evaporated by rotary-evaporation to dryness. The residual was dissolved in anhydrous DCM (3 mL), followed by addition of TEA (0.6 μL, 0.004 mmol, 1.5 eq.) and DCC (0.7 mg, $3.5101 \times 10^{-6}$ mol, 1.2 eq.). The solution was allowed to stir under argon atmosphere overnight. The mixture was filtered, and loaded on to a small silica gel column (10 mL) followed by elution with DCM. The eluent (30 mL) was concentrated to 1 mL by rotary evaporation. The solution was added into ethyl ether (15 mL) to precipitate. The precipitate collected by filtration and dried in vacuum to yield 30 mg of white powder (19). $^1$H NMR of compound 19 (Varian, 10 mg/mL DMSO-d6, δ) showed the usual POZ backbone peaks at 0.95 ppm (s) and 0.97 (s) (total area 3H per $CH_3CH_2CO$—); 2.27 ppm (large s) and 2.32 ppm (small s) (total area 2H per $CH_3CH_2CO$—); and 3.35 ppm (large s) and 3.47 (small s) (total area 4H per —$NHCH_2CH_2NH$—). POZ terminal maleimide group peak appeared at 7.00 ppm (s, 2H). Some of pendent PEG4-VC-PABC-MMAE relevant peaks (number of H below refer to per pendent PEG4-VC-PABC-MMAE) include 0.70-0.95 ppm, m, 24H, —$CH_3$; 3.50 ppm, s, —$(CH_2CH_2O)_3$—; 3.79 ppm, t, ill resolved, 2H per triazole-$CH_2CH_2O$—); 3.99 ppm, m, 2H; 4.23 ppm, m, 2H; 4.45 ppm (main peak, t, ill resolved, 2H per triazole-$CH_2CH_2O$—); 5.04 ppm, m, 2H; 5.41 ppm, s, 2H; 6.04 ppm, s, 1H; 7.17 ppm, m, 1H, Ar on MMAE; 7.27 ppm, d, 2H, Ar of PAB; 7.31 ppm, m, 4H, Ar on MMAE; 7.59 ppm, d, 2H, Ar of PAB; 7.82 ppm (m, 1H per triazole ring =CH—N); 8.13 ppm, d, 1H; 10.03 ppm, s, 1H.

Example 11

POZ 20K Pendent [(Biotin)$_2$(PEG4-VC-PABC-MMAE)$_5$]$_a$-Iodoacetamide (22)

Reaction Scheme:

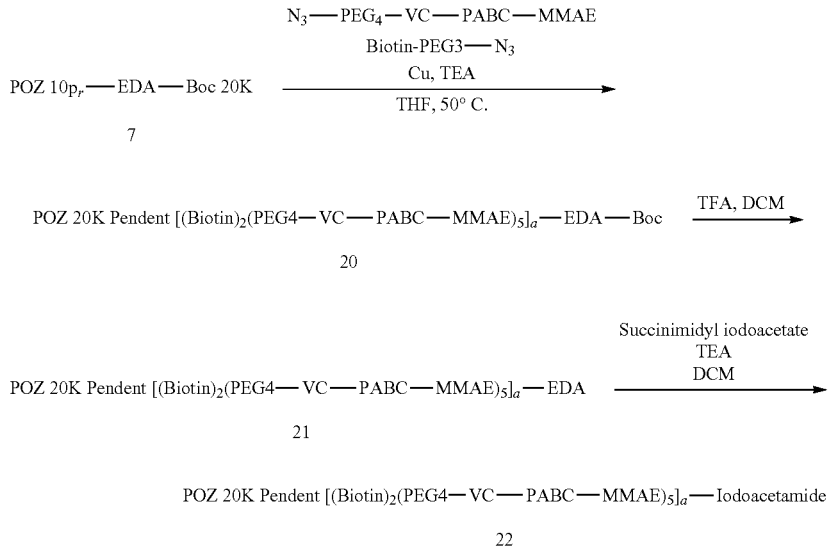

(20)

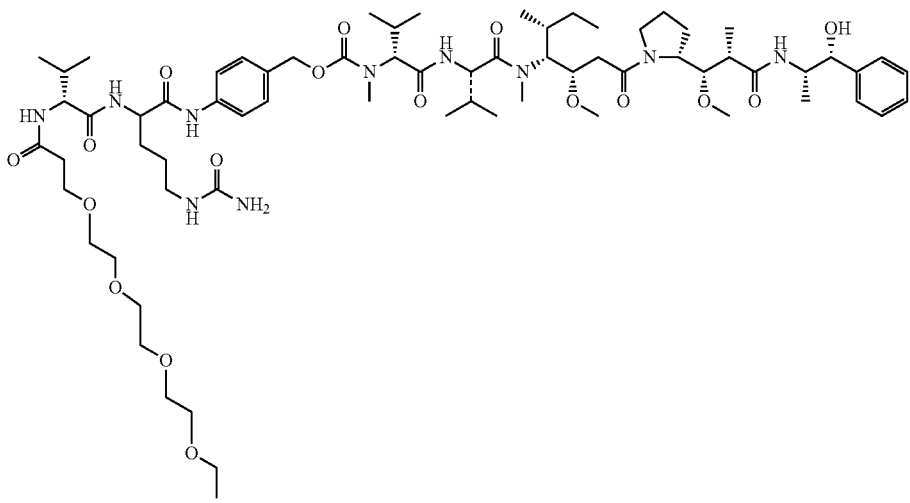

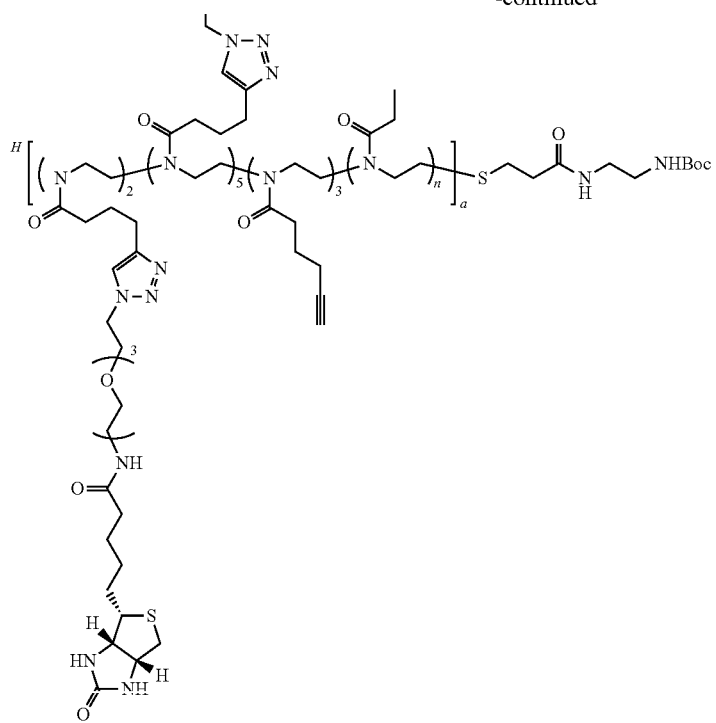
Structure of 20K Pendent
[(Biotin)₂(PEG4-VC-PABC-MMAE)₅]ₐ-EDA-Boc
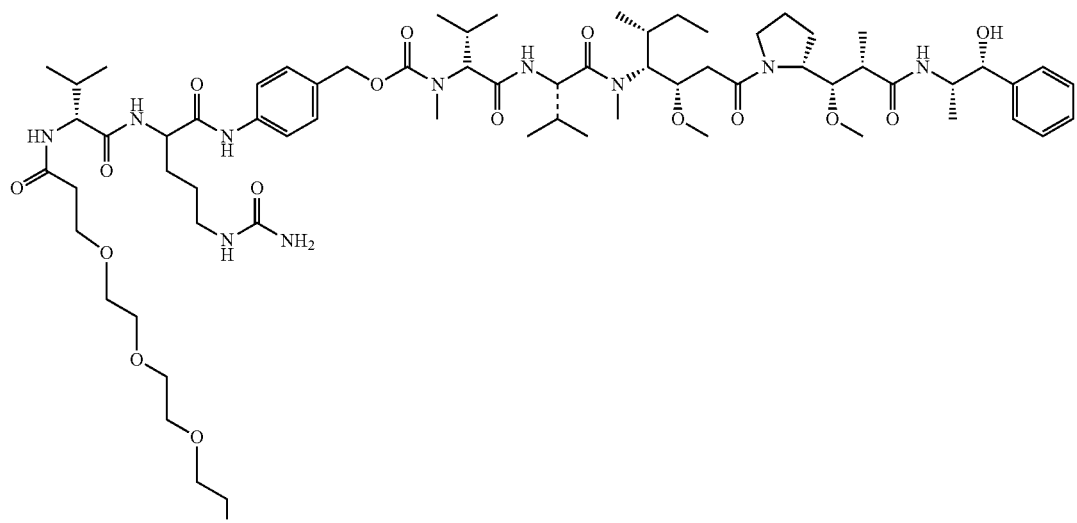
(21)

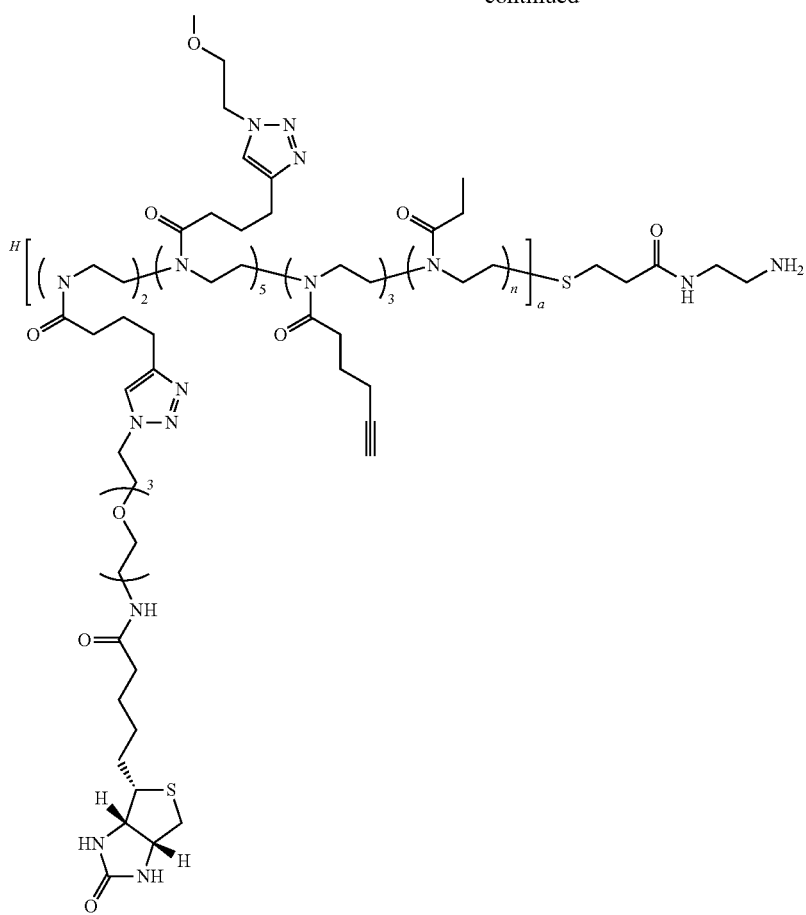
Structure of POZ 20K pendent [(Biotin)$_2$(PEG4-VC-PABC-MMAE)$_5$]$_a$-EDA
(22)
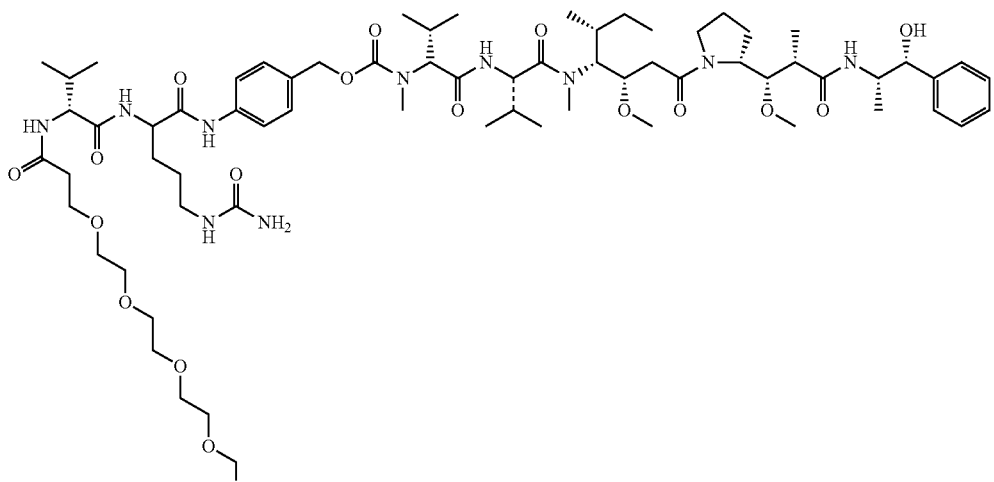

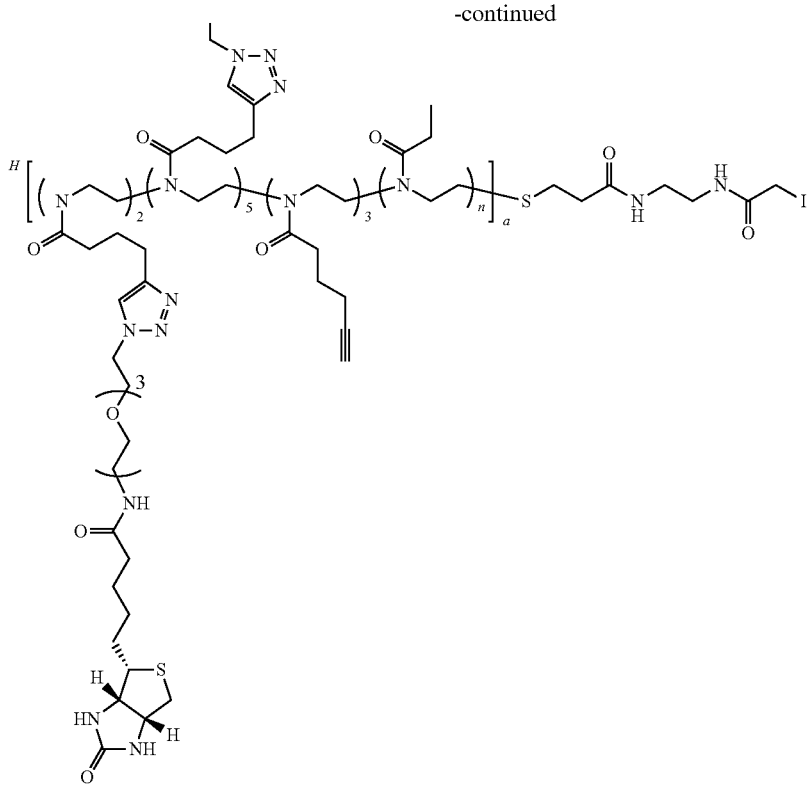

Structure of POZ 20K pendent [(Biotin)$_2$(PEG4-VC-PABC-MMAE)$_5$]$_a$-Iodoacetamide To N$_3$-PEG4-VC-PABC-MMAE (132 mg, 0.0944 mmol, 6.0 eq.) and POZ 10p-EDA-Boc 20K (7, 305 mg, 0.0157 mmol, 1 eq.) in a 50 mL round bottom flask was added Biotin-PEG3-azide (14 mg, 0.032 mmol, 2 eq., dissolved in 0.6 mL of DMF), followed by addition of 9 mL of anhydrous THF (9 mL). The solution was protected under argon and stirred at room temperature for 15 min. CuI (19 mg, 0.10 mmol, 6.8 eq.) was then added, followed by immediate addition of TEA (52 µL, 0.37 mmol, 24 eq.). The greenish solution was stirred at 50° C. overnight under argon. The solution was filtered through a 0.2 µm syringe filter, and the filtrate was evaporated to dryness. DMF was evaporated under vacuum. Methanol (10 mL) was added to the residual solid. Copper ions were removed by passing the methanol solution through a column packed with Dowex® M4195 media (5 gm). The eluent was concentrated to dryness and dissolved in DCM (6 mL). The clear solution was precipitated in diethyl ether (150 mL) with stirring. The precipitate was collected by filtration and dried in vacuum to yield 400 mg of amber colored powder (20). $^1$H NMR of compound 20 (Varian, 10 mg/mL DMSO-d6, δ) showed the usual POZ backbone peaks at 0.95 ppm (s) and 0.97 (s) (total area 3H per CH$_3$CH$_2$CO—); 2.27 ppm (large s) and 2.32 ppm (small s) (total area 2H per CH$_3$CH$_2$CO—); and 3.35 ppm (large s) and 3.47 (small s) (total area 4H per —NHCH$_2$CH$_2$NH—). POZ terminal Boc group peak appeared at 1.37 ppm (s, 9H). Some of the pendent biotin related peaks include 3.79 ppm (t, ill resolved, 2H per triazole-CH$_2$CH$_2$O—); 4.12 ppm (m, 1H per —CONHCH(CH$_2$S—)— on biotin) and 4.30 ppm (m, 1H per —CONHCH on biotin); 4.45 ppm (t, ill resolved, 2H per triazole-CH$_2$CH$_2$O—); 6.34 ppm (s)(2H per —NH—CO—NH—) and 6.40 ppm (s); 7.81 ppm (m, 1H per triazole ring =CH—N, 1H per —CONH—). Some of pendent PEG4-VC-PABC-MMAE relevant peaks (number of H below refer to per pendent PEG4-VC-PABC-MMAE) include 0.70-0.95 ppm, m, —CH$_3$; 3.50 ppm, s, —(CH$_2$CH$_2$O)$_3$—; 3.79 ppm, t, ill resolved, 2H per triazole-CH$_2$CH$_2$O—); 3.99 ppm, m, 2H; 4.23 ppm, m, 2H; 4.45 ppm (main peak, t, ill resolved, 2H per triazole-CH$_2$CH$_2$O—); 5.04 ppm, m, 2H; 5.40 ppm, s, 2H; 5.90 ppm, s, 1H; 7.16 ppm, m, 1H, Ar on MMAE; 7.27 ppm, d, 2H, Ar of PAB; 7.31 ppm, m, 4H, Ar on MMAE; 7.58 ppm, d, 2H, Ar of PAB; 7.82 ppm (m, 1H per triazole ring =CH—N); 8.13 ppm, d, 1H; 9.98 ppm, s, 1H.

Compound 20 (390 gm) was dissolved in anhydrous DCM (2 mL) followed by addition of TFA (2 mL). The solution was stirred at room temperature under argon for three hours. The mixture was then evaporated to dryness. The residual solid was dissolved in ACN (5 mL), followed by mixing with deionized water (15 mL). ACN was then evaporated by rotary evaporation. The pH of remaining solution was adjusted to 11 by 1 N NaOH, followed by dissolving sodium chloride (1.5 gm) into the solution. The aqueous solution was extracted with DCM (3×30 mL). The DCM phase was collected, dried over anhydrous MgSO$_4$ (1.5 gm) and Na$_2$SO$_4$ (20 gm). The mixture was filtered to remove the solids, and the filtrate was evaporated to dryness by rotary evaporation. The residual was dried in vacuum overnight, which afforded 289 mg of solid (21). $^1$H NMR of compound 21 (Varian, 10 mg/mL DMSO-d6, δ) indicated the complete cleavage of terminal Boc group as shown by the disappearance of singlet peak at 1.37 ppm. $^1$H NMR of compound 21 (Varian, 10 mg/mL DMSO-d6, δ) indicated the complete cleavage of terminal Boc group as shown by the disappearance of singlet peak at 1.37 ppm.

Compound 21 (150 mg, 5.86×10$^{-3}$ mmol, 1 eq.) was dissolved in chloroform (6 mL), which was then evaporated to dryness by rotary evaporation. The residual was dissolved in DCM (6 mL) and protected under argon atmosphere. Succinimidyl iodoacetate (3.4 mg, 1.2×10$^{-2}$ mmol, 2.0 eq.) was added, followed by addition of TEA (6.5 µL, 4.7×10$^{-2}$ mmol, 8 eq.). The solution was allowed to stir in the dark overnight. The solution was then slowly added into 80 mL of diethyl ether with stirring to precipitate the product. The precipitate was filtered, rinsed with diethyl ether (5 mL), and dried in vacuum to yield 140 mg of white powder. The solid was dissolved in 50 mM NaH$_2$PO$_4$ (7 mL, pH4.6). The solution was then dialyzed in a Slide-A-Lyzer (3-12 mL, 2,000 MWCO) dialysis cassette against DI water (3×1 L) overnight. The solution was evaporated to dryness by rotary evaporation. The residual was dissolved in chloroform (5 mL) and evaporated. The residual was re-dissolved in chloroform (5 mL), and evaporated to dryness. The residual was then dissolved in DCM (6 mL), and then precipitated into diethyl ether (80 mL) with stirring. The precipitate was filtered and rinsed with diethyl ether (5 mL), and dried in vacuum to yield 118 mg of white powder (22). Reversed phase HPLC analysis of 22 shows purity of >99%. Iodoacetamide substitution of 22 was 67%, as determined by ion exchange chromatography after reacting with 3-mercaptopropionic acid.

Example 12

Conjugation of POZ (Biotin)$_{10}$ Maleimide to Antibody

Figure 1B:
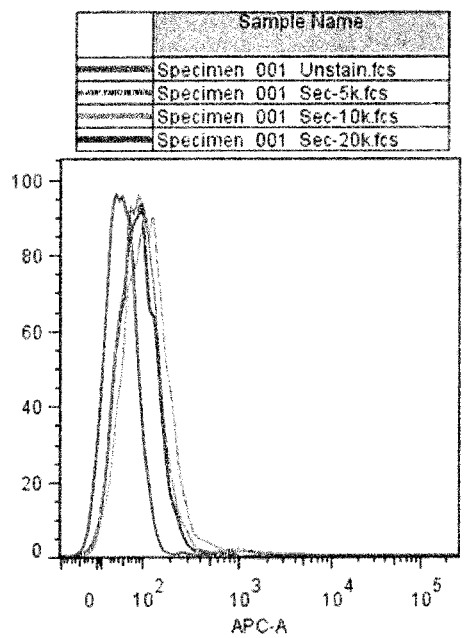
FIG. 1B shows flow cytometry plots of R11 POZ Biotin with MEC-1 cells.

POZ (Biotin)$_{10}$-Maleimide reagents of 5, 10 and 20 kDa were attached to the R11 sc-Fv-FC specific ROR1 antibody. The typical conjugation conditions were antibody 4 µM, POZ-biotin 100 µM, DTT 0.1 mM dissolved in 100 mM sodium acetate buffer (pH 5.2) and mixed at room temperature for 1 h. A protein-A separation column is then used to separate the unconjugated POZ polymer from the antibody and POZ-antibody conjugate with a washing and eluting buffer of 100 mM sodium acetate (pH 5.2). The conjugated antibodies were then separated from the unconjugated antibodies with the aid of a monomeric avidin flow-through kit, where the biotin linked to the polymer backbone has a strong affinity for avidin. The POZ conjugates of different molecular weights were then incubated with HBL-2 (ROR+) and MEC-1 (ROR−) cells. FIG. 1 shows that the size of the POZ polymer when attached to a single site on the antibody did not appear to alter its ability to bind selectively to cells that express the antigen (HBL-2); the polymer-conjugate shows little binding to cells that do not express the antigen (MEC-1).

Figure 2:
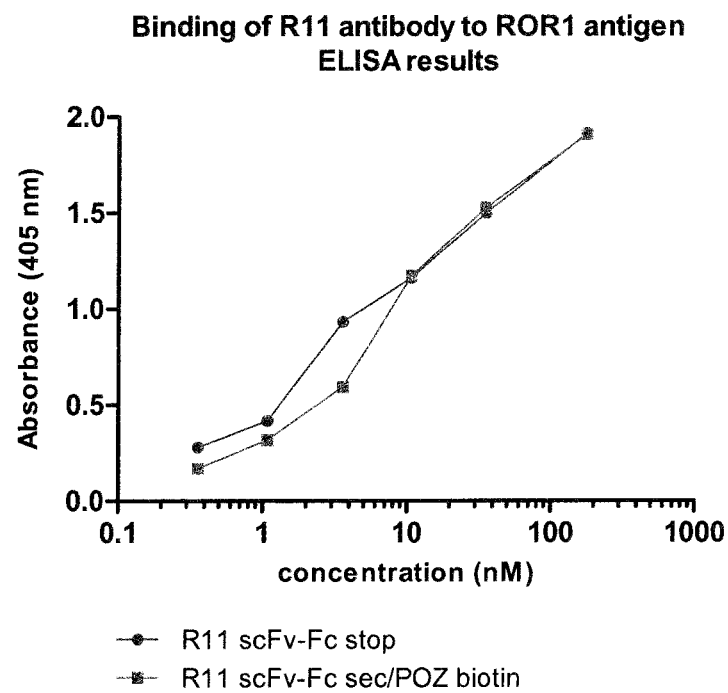
FIG. 2 shows SDS-PAGE of POZ MMAE conjugates of CD79b before, during and after purification.

POZ-ADC binding activity can also be verified by ELISA. Each well of a 96-well plate is coated with the hROR1 ECD antigen and incubated in TBS for 1 h at 37° C. After blocking with 150 µL 3% (w/v) BSA/TBS for 1 h at 37° C., the R11 sc-Fv-FC specific ROR1 antibody with or without POZ polymer attached is added and incubated for 2 h at 37° C. The POZ molecule used in this experiment is the POZ 10p maleimide polymer described above. After washing each well, dilutions of the fragment specific secondary antibody, anti-human donkey IgG Fcγ with stabilized HRP activity is added. After washing with water, colorimetric detection is performed using 2,2'-azino-bis(3-ethylbenzthiazoline)-6-sulfonic acid. The absorbance is measured at 405 nm using a microplate reader. A plot of Absorbance versus ROR1 antibody concentration (FIG. 2) is made to portray the binding efficiencies of the native versus polymer-ADC conjugated antibody. This plot revealed that the native antibody and the polymer-ADC conjugated antibody bound the hROR1 ECD antigen in a similar manner, leading to the conclusion that the POZ polymer does not interfere with antigen binding.

Example 13

Figure 3:
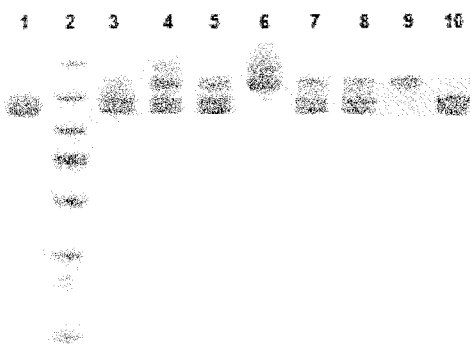
FIG. 3 shows the binding of native and polyoxazoline conjugated R11 antibody to the ROR1 antigen by an ELISA assay.

Conjugation of POZ 20K Pendent [(Biotin)$_2$(PEG4-VC-PABC-MMAE)$_1$]$_a$-Iodoacetamide and POZ 20K Pendent [(Biotin)$_2$(PEG4-VC-PABC-MMAE)$_5$]$_a$-Iodoacetamide to Antibody POZ 20K pendent [(Biotin)$_2$ (PEG4-VC-PABC-MMAE)$_1$]$_a$-iodoacetamide and POZ 20K pendent [(Biotin)$_2$ (PEG4-VC-PABC-MMAE)$_5$]$_a$-iodoacetamide were attached to the R11 sc-Fv-Fc specific ROR1 antibodies, R12 sc-Fv-Fc specific ROR2 antibodies and to CD79b antibodies. The conjugation and purification conditions are explained above. A protein-A separation column is used to separate the unconjugated POZ polymer from the native antibody and POZ-antibody conjugate with a washing and eluting buffer of 100 mM sodium acetate (pH 5.2). The POZ conjugated antibodies were then separated from the unconjugated antibodies with the aid of a monomeric avidin flow-through kit, where the biotin on the polymer backbone has a strong affinity for avidin. SDS PAGE patterns (Coomassie stain) of the CD-79b POZ val-cit-PABC-MMAE conjugates in FIG. 3 shows each step of conjugation and purification. The purified POZ antibody conjugates were then incubated with HBL-2 (ROR+), MEC-1 (ROR−) and Ramos cells. Flow cytometry showed high cell surface binding of all the POZ conjugates to Ramos cells and not to MEC-1 cells (data not shown). The lane assignments are shown below.

| Lane | Sample |
|---|---|
| 1 | CD79b-stop |
| 2 | protein MW marker |
| 3 | CD79b-Sec before conjugation |
| 4 | CD79b-POZ-(MMAE)1 after protein A separation |
| 5 | CD79b-POZ-(MMAE)1 Mono-Avidin flow-through |
| 6 | CD79b-POZ-(MMAE)1 after Mono-Avidin separation |
| 7 | CD79b-POZ-(MMAE)5 after protein A separation |
| 8 | CD79b-POZ-(MMAE)5 Mono-Avidin flow-through |
| 9 | CD79b-POZ-(MMAE)5 after Mono-Avidin separation |
| 10 | CD79b-vc-MMAE |

Example 14

Conjugation of POZ 20K Pendent [(Biotin)$_2$ (PEG4-VC-PABC-Deacetylcolchicine)$_6$]$_a$-Iodoacetamide and POZ 20K Pendent [(Biotin)$_2$ (PEG4-Phe-Lys-PABC-Deacetylcolchicine)$_5$]$_a$-Iodoacetamide to Antibody POZ (Biotin)$_2$ (Val-Cit-PAB-DC)$_6$ iodoacetamide and POZ (Biotin)$_2$ (Phe-Lys-PAB-DC)$_5$ iodoacetamide were attached to the R11, R12 sc-Fv-FC specific ROR1 and ROR2 antibodies and to CD79b antibodies. The typical conjugation and purification conditions are explained above. SDS PAGE patterns (Coomassie stain) of the CD-79b POZ (phe-lys-PAB-DC)$_5$ conjugate during each step of conjugation and purification shows that conjugation and purification occurred. The pure POZ antibody conjugates were then incubated with HBL-2 (ROR+), MEC-1 (ROR−) and Ramos cells. Flow cytometry data shows high cell surface binding of all the POZ conjugates to HBL-2 and Ramos cells and not to MEC-1 cells.

Example 15

Figure 4:
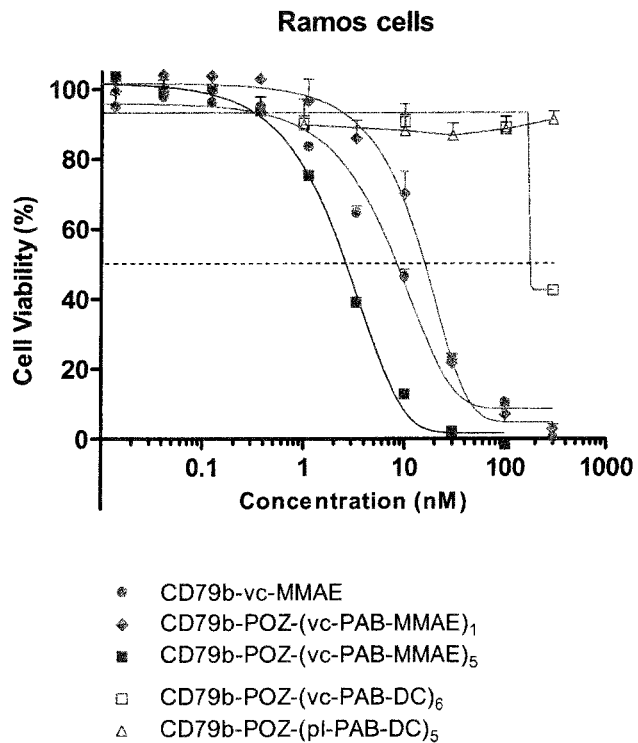
FIG. 4 show the effect of concentration of CD79b POZ drug conjugates of MMAE and deacetylcolchicine (DC) on the viability of Ramos cells.
Figure 5:
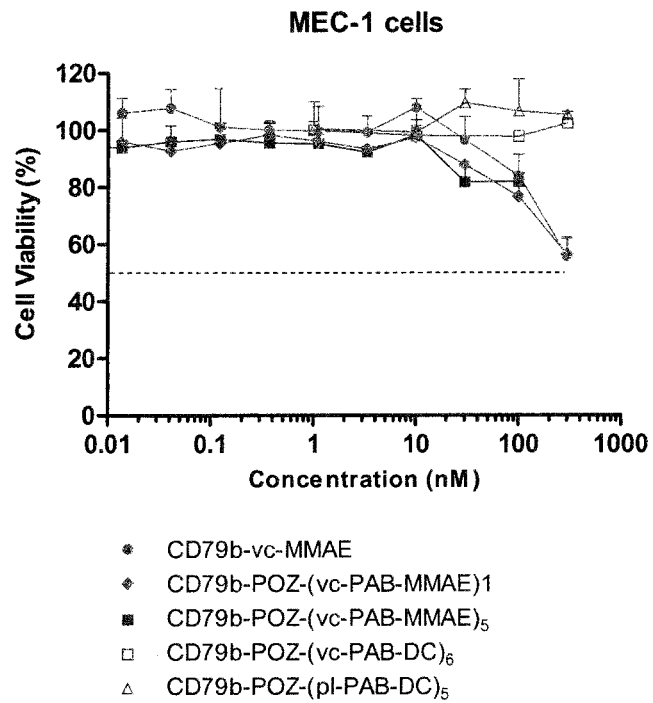
FIG. 5 shows the effect of concentration of CD79b POZ drug conjugates of MMAE and deacetylcolchicine (DC) in the viability of MEC-1 cells

Potency of CD79b Conjugates of POZ 20K Pendent (PEG4-VC-PABC-MMAE)$_1$, POZ 20K Pendent (PEG4-VC-PABC-MMAE)$_5$, POZ (PEG4-VC-PABC-Deacetylcolchicine)$_6$ and POZ 20K Pendent (PEG4-Phe-Lys-PABC-Deacetylcolchicine)$_5$ Ramos and MEC-1 cells were incubated with different concentrations of CD79b-conjugated POZ drug conjugates for 96 hours in a cytotoxicity assay. FIG. 4 shows the effect of increasing concentrations of the CD79b-POZ conjugates on the viability (%) of Ramos cells in-vitro. The data shows that POZ Val-Cit-PAB conjugates with one MMAE molecule attached had an IC$_{50}$ of about 20 nM. When compared to the conjugate with an average of five MMAE molecules the IC$_{50}$ was reduced by approximately one log to about 2 nM. This data shows that increasing the number of MMAE molecules per POZ conjugate increases the IC$_{50}$ by a factor of 10; i.e., higher drug antibody ratios (DAR) improve the activity and potency of the polymer-ADC. The POZ val-cit-PAB conjugate of DC had an IC$_{50}$ of about 200 nM and the POZ Phe-Lys-PAB conjugate of DC had reduced activity, even though both CD-79b conjugates had high cell surface binding to Ramos cells. This suggests that deacetylcolchicine (DC) is not as potent as MMAE in the Ramos cell study. In addition, the Val-Cit linker appeared to be more facile at intracellular release, which may make attractive for some applications where intracellular release is a factor. FIG. 5 shows the effect of concentration of the CD79b-POZ conjugates on the viability (%) of MEC-1 cells. The data shows that the POZ val-cit-PAB conjugates of MMAE had an IC$_{50}$ of greater than 300 nM, and the conjugates with DC as the cytotoxic agent had no activity. All these conjugates had poor cell surface binding to MEC-1 cells as expected due to the low concentration of antigen for the CD79b antibody.

Example 16

Potency of R11 Conjugates of POZ 20K Pendent (PEG4-VC-PABC-MMAE)$_5$

Figure 6:
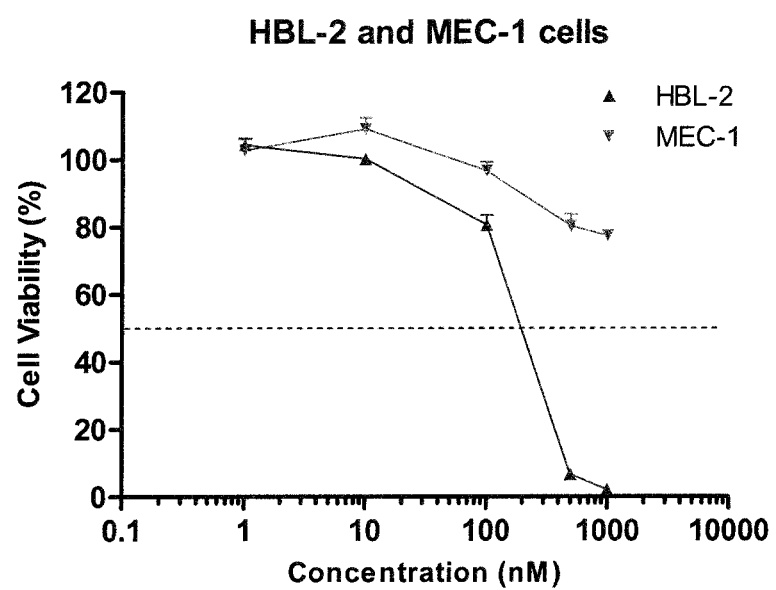
FIG. 6 shows the effect of concentration of R11 POZ drug conjugates of MMAE on the viability of HBL-2 and MEC-1 cells.

HBL-2 and MEC-1 cells were incubated with different concentrations of R11 conjugated to POZ-MMAE for 96 hours in the cytotoxicity assay. FIG. 6 shows the effect of concentration of the R11-POZ-(PEG4-VC-PABC-MMAE)$_5$ conjugate on the viability (%) of HBL-2 (ROR+) and MEC-1 (ROR−) cells in-vitro. The data shows this compound had an IC$_{50}$ of about 200 nM against HBL-2 cells and no activity against MEC-1 cells.

The invention claimed is:
1. A polymer conjugate, the polymer conjugate comprising a polyoxazoline polymer, a single chain antibody linked to the polyoxazoline polymer, an optional purification moiety and a plurality of agents linked to the polyoxazoline polymer via a releasable linkage, wherein the single chain antibody and the polyoxazoline polymer are present in a 1:1 ratio, the polymer conjugate having the structure:

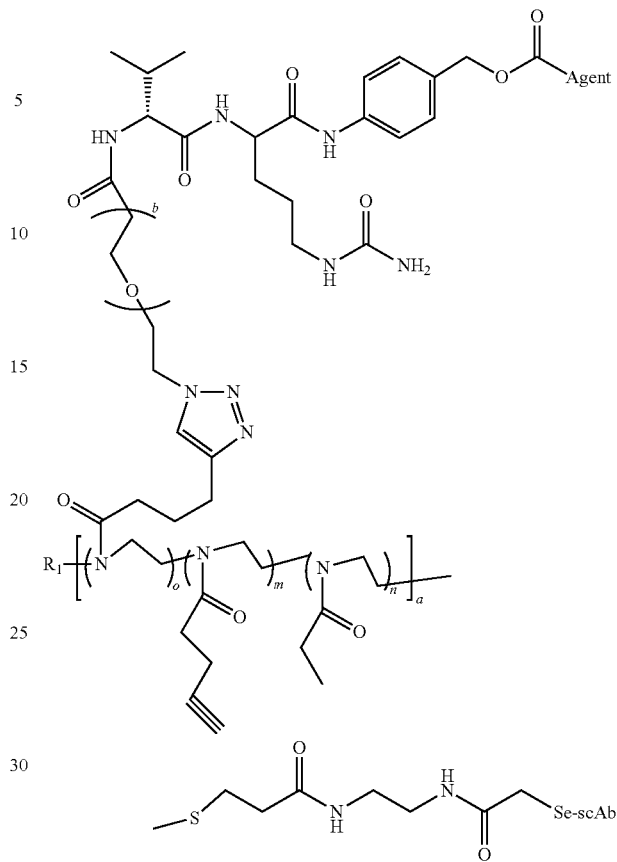

wherein
a is ran which indicates a random copolymer or block which indicates a block copolymer;
$R_1$ is H;
o is an integer from 0 to 50;
m is an integer from 0 to 50;
n is an integer from 0 to 1000;
b is an integer from 1 to 30;
scAb is a single chain antibody;
Se is a selenocysteine residue;
Agent is selected from the group consisting of monomethyl auristatin E, monomethyl auristatin F, desmethyl-auristatin F, daunorubicine, doxorubicin, epirubicin, idarubicin, valrubicin, mitoxantrone, calicheamicin, N-acetyl-γ calicheamicin 1,2-dimethyl hydrazine dichloride, DM1, DM4, ansomitocin, abbeymycin, chicamycin, DC-81, mazethramycin, neothramycins A and B, porothramycin prothracarcin, sibanomicin, sibiromycin, tomamycin, SJG-136, SG 2285, DRG-16, ELB-21, colchicine, deacetylcholchicine, dolstatin 10, dolstatin 15, dolstatin 16, tubulysin A, tubulysin B, tubulysin D, tubulysin M, maytansinol, duocarmycin A, duocarmycin B1, duocarmycin B2, duocarmycin C1, duocarmycin C2, duocarmycin D, duocarmycin SA, CC-1065, adozelesin, bizelesin, carzelesin, nemorubicin, cryptophycin 1, cryptophycin 8, cryptophycin 24, cryptophycin 52, cryptophycin 55, cryptophycin 296, cryptophycin 309, epithilone A, epithilone B, epithilone C, epithilone D, epithilone E, epithilone F, BMS 247550, BMS 310705, safracin A and safracin B; and the number of agents and optional purification moieties linked to the conjugate is less than or equal to the sum of o and m, provided that both o and m are not each 0 and the total of n, o and m is at least 30.

2. The polymer conjugate of claim 1, wherein the selenocysteine residue is part of the single chain antibody and the selenocysteine residue is conjugated to the polyoxazoline polymer.

3. The polymer conjugate of claim 1, wherein m is 0, o is an integer from 5 to 20 and the total of o and n is from 30 to 100.

4. The polymer conjugate of claim 3, wherein the conjugate has an agent to antibody ratio of 5:1 (agent to antibody).

5. The polymer conjugate of claim 1, wherein m is 0, o is 5 and the total of o and n is from 30 to 100.

6. The polymer conjugate of claim 1, wherein m is 0, o is 10 and the total of o and n is from 30 to 100.

7. The polymer conjugate of claim 6, wherein the conjugate has an agent to antibody ratio of 10:1 (agent to antibody).

8. The polymer conjugate of claim 1, wherein the optional purification moiety is absent.

9. The polymer conjugate of claim 1, wherein the optional purification moiety is present.

10. The polymer conjugate of claim 1, wherein the purification moiety is biotin.

* * * * *